United States Patent
Thosar et al.

(10) Patent No.: US 6,558,707 B1
(45) Date of Patent: *May 6, 2003

(54) IMMEDIATE RELEASE EPLERENONE COMPOSITIONS

(75) Inventors: Shilpa S. Thosar, Des Plaines, IL (US); Rajeev D. Gokhale, Waukegan, IL (US); Dwain S. Tolbert, Wadsworth, IL (US)

(73) Assignee: G. D. Searle & Co., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/100,712

(22) Filed: Mar. 19, 2002

Related U.S. Application Data

(63) Continuation of application No. 09/456,614, filed on Dec. 8, 1999, now Pat. No. 6,410,054.
(60) Provisional application No. 60/111,646, filed on Dec. 9, 1998.

(51) Int. Cl.[7] .................................................. A61K 9/14
(52) U.S. Cl. ...................... 424/489; 424/451; 424/464; 424/468; 424/175; 424/481; 514/951
(58) Field of Search ................................ 424/489, 451, 424/464, 408, 175; 514/951

(56) References Cited

U.S. PATENT DOCUMENTS

| | | | |
|---|---|---|---|
| 4,559,332 A | 12/1985 | Grob et al. ................ | 514/175 |
| 4,753,802 A | 6/1988 | Stephans et al. ............ | 424/467 |
| 4,828,836 A | 5/1989 | Elger et al. ................ | 424/419 |
| 4,847,093 A | 7/1989 | Ayer et al. ................ | 424/473 |
| 4,975,284 A | 12/1990 | Stead et al. ................ | 424/497 |
| 5,057,317 A | 10/1991 | Iida ............................ | 424/423 |
| 5,082,668 A | 1/1992 | Wong et al. ................ | 424/473 |
| 5,160,744 A | 11/1992 | Jao et al. ................... | 424/473 |
| 5,190,765 A | 3/1993 | Jao et al. ................... | 424/473 |
| 5,324,718 A | 6/1994 | Loftsson .................... | 514/58 |
| 5,354,556 A | 10/1994 | Sparks et al. ............... | 424/419 |
| 6,410,054 B1 * | 6/2002 | Thosar et al. ............... | 424/489 |

FOREIGN PATENT DOCUMENTS

| | | | |
|---|---|---|---|
| EP | 0 572 942 | 12/1993 | ............ A61K/9/28 |
| WO | WO 92/13547 | 8/1992 | .......... A61K/37/02 |
| WO | WO 92/00729 | 1/1993 | ............ A61K/9/22 |
| WO | WO 94/27582 | 12/1994 | ............ A61K/9/48 |
| WO | WO 95/15166 | 6/1995 | ......... A61K/31/585 |
| WO | WO 98/25948 | 6/1998 | |

OTHER PUBLICATIONS de Gasparo et al. (1987). Three new epoxy–spironolactone derivatives: characterization in vivo and in vitro. Journal of Pharmachology and Experimental Therapeutics 240, 650–656.

de Gasparo et al. (1989). Antialdosterones: incidence and prevention of sexual side effects. Journal of Steroid Biochemistry 32 (1B), 223–227.

Delyani, John A. (1998) Anti–aldosterone therapy in the treatment of heart failure: new thoughts on an old hormone. In Expert Opin. Invest. Drugs. 7(5), pp. 753–759.

\* cited by examiner

*Primary Examiner*—Thurman K. Page
*Assistant Examiner*—Lakshmi Channavajjala
(74) *Attorney, Agent, or Firm*—James C. Forbes

(57) ABSTRACT

The invention relates to oral pharmaceutical compositions useful as aldosterone receptor blockers comprising the active agent micronized eplerenone in an amount of about 10 mg to about 1000 mg and one or more carrier materials.

62 Claims, 2 Drawing Sheets

IMMEDIATE RELEASE EPLERENONE COMPOSITIONS

This application is a continuation of application Ser. No. 09/456,614 filed on Dec. 8, 1999, now U.S. Pat. No. 6,410,054, which claims priority of U.S. provisional application Serial No. 60/111,646 filed on Dec. 9, 1998.

DESCRIPTION

Technical Field

The present invention relates to pharmaceutical compositions comprising the compound eplerenone as an active ingredient, and more particularly to pharmaceutical compositions containing micronized eplerenone, methods of treatment comprising administering such pharmaceutical compositions to a subject in need thereof, and the use of such compositions in the manufacture of medicaments.

BACKGROUND OF THE INVENTION

The compound methyl hydrogen 9,11α-epoxy-17α-hydroxy-3-oxopregn-4-ene-7α,21-dicarboxylate, γ-lactone (also referred to herein as eplerenone) was first reported in Grob et al., U.S. Pat. No. 4,559,332 that describes and claims a class of 9,11-epoxy steroid compounds and their salts together with processes for the preparation of such compounds. These 9,11-epoxy steroid compounds are described as aldosterone antagonists that can be administered in a therapeutically effective amount to treat pathological conditions associated with hyperaldosteronism such as hypertension, cardiac insufficiency and cirrhosis of the liver. U.S. Pat. No. 4,559,332 contains general references to formulations for the administration of these 9,11-epoxy steroid compounds such as tablets and capsules.

Ng et al., WO 98/25948 later disclosed additional synthetic processes for the preparation of a similar class of 9,11-epoxy steroid compounds and their salts, including eplerenone. Both U.S. Pat. No. 4,559,332 and WO 98/25948 are incorporated by reference herein.

Eplerenone corresponds in structure to Formula I, below:

(I)

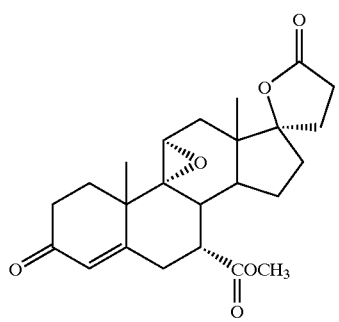

Spironolactone, another 20-spiroxane-steroid having activity as an aldosterone antagonist, is commercially available for the treatment of hypertension. Spironolactone corresponds in structure to Formula II, below:

(II)

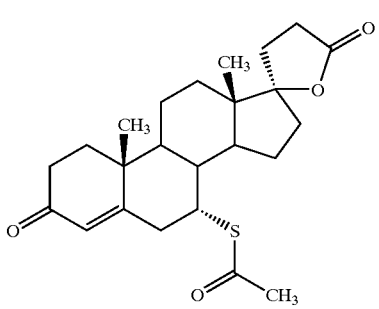

Spironolactone, however, exhibits antiandrogenic activity that can result in gynecomastia and impotence in men, and weak progestational activity that produces menstrual irregularities in women. Commercial formulations of spironolactone (sold under the name Aldactone™) contain 25, 50 or 100 mg doses of spironolactone in a matrix comprising, among other carrier materials, calcium sulfate dihydrate as a diluent, maize starch as a disintegrant, povidone K-30 as a binding agent, magnesium stearate as a lubricant, and flavor, colorant, and coating ingredients that include hydroxypropylmethylcellulose and polyethylene glycol 400.

de Gasparo et al., in Journal of Steroid Biochemistry 32 (1B), 223–227 (1989) report the use of spironolactone and epoxymexrenone in receptor binding studies. Those materials, with spironolactone in a commercial formulation with a particle size of 5 microns and the epoxymexrenone at a particle size of 20 microns in a non-formulated composition, were also used in vivo to study excretion of sodium in urine.

There is a need for the development of additional active aldosterone antagonists such as eplerenone that interact minimally with other steroid receptor systems such as glucocorticoid, progestin and androgen steroid receptor systems and/or that provide for a broader range of treatment. There is also a need for eplerenone compositions that provide a readily soluble form of eplerenone. The discussion that follows discloses eplerenone compositions that help to fulfill that need.

BRIEF SUMMARY OF THE INVENTION

The effective administration of eplerenone to a subject has been complicated by the compound's low solubility and low compressibility as well as by its other physical and chemical properties. Pharmaceutical compositions comprising micronized eplerenone and a pharmaceutically acceptable carrier material, however, have been discovered that can effectively deliver a therapeutically preferred amount of the compound to the subject. In addition, unique combinations of carrier material with the micronized eplerenone have been found that provide still better solubilization characteristics. These combinations of active compound and carrier material have been found to possess improved bioavailability, chemical stability, physical stability, dissolution profiles, disintegration times, safety, as well as other improved pharmacokinetic, chemical and/or physical properties. The present invention comprises these pharmaceutical compositions, unit dosage forms based thereon, and methods for the preparation and use of both.

BRIEF DESCRIPTION OF THE DRAWINGS

In the drawing forming a portion of this disclosure, FIG. 1, shown in two portions as FIGS. 1A and 1B, is a schematic diagram of a manufacturing process for a composition of this invention.

DETAILED DESCRIPTION OF THE INVENTION

Figure 1A:
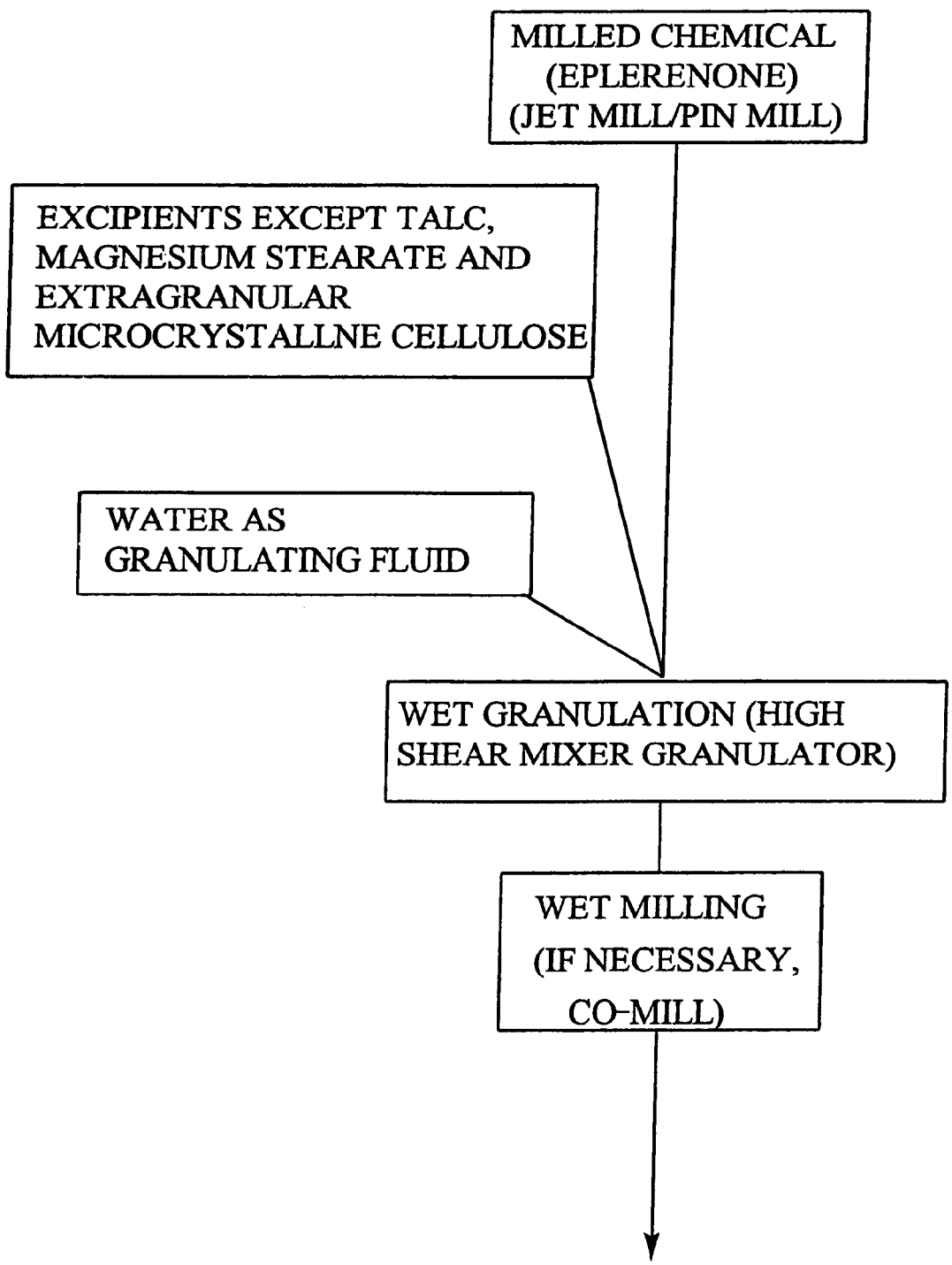

It has been discovered that pharmaceutical compositions comprising micronized eplerenone as the active ingredient in a daily dosage amount about 10 mg to about 1000 mg along with a pharmaceutically acceptable carrier material are unique compositions exhibiting superior performance as aldosterone receptor blockers. Such pharmaceutical compositions exhibit superior activity, potency, safety and therapeutic effectiveness at this dosage range. These compositions provide eplerenone to a patient at a dosage that is sufficient to provide prolonged blocking of aldosterone receptors and thus confer the desired therapeutic benefit, while maintaining a safe clearance time. Undesirable side effects such as, but not limited to, gastrointestinal irritation, antiandrogenic and progestational activity are also minimized with the pharmaceutical compositions of the present invention.

These pharmaceutical compositions are advantageously used to block aldosterone receptors and, among other pharmacological actions, can increase sodium and water excretion with a concomitant potassium-sparing effect. Such compositions can be specifically employed for the prophylaxis and treatment of cardiovascular diseases such as heart failure; hypertension (especially the management of mild to moderate hypertension); edema associated with liver insufficiency; post-myocardial infarction; cirrhosis of the liver; stroke prevention; and reduction of heart rate for subjects exhibiting an accelerated heart rate. These pharmaceutical compositions exhibit, among other features, (i) improved selectivity for aldosterone receptors, (ii) reduced binding affinity to the progesterone and androgen receptor, and (iii) reduced interference from plasma proteins.

Besides being useful for human treatment, these compositions are also useful for veterinary treatment of companion animals, exotic animals and farm animals, including mammals, rodents and the like. More preferred non-human animals include horses, dogs, and cats.

Unformulated eplerenone administered in capsule form is not well absorbed in the gastrointestinal tract. Accordingly, a need exists for suitable eplerenone dosage forms. The pharmaceutical compositions of the present invention provide these dosage forms and exhibit one or more superior properties relative to unformulated eplerenone and/or other compositions comprising eplerenone. These superior properties include, but are not limited to, one or more of the following:

(1) improved bioavailability;
(2) improved solubility of the pharmaceutical composition;
(3) decreased disintegration times for immediate release oral dosage forms;
(4) decreased dissolution times for immediate release oral dosage forms;
(5) improved dissolution profiles for controlled release oral dosage forms;
(6) decreased tablet friability;
(7) increased tablet hardness;
(8) improved safety for oral dosage forms;
(9) reduced moisture content and/or hygroscopicity for oral dosage forms;
(10) improved composition wettability;
(11) improved particle size distribution of eplerenone;
(12) improved composition compressibility;
(13) improved composition flow properties;
(14) improved chemical stability of the final oral dosage form;
(15) improved physical stability of the final oral dosage form;
(16) decreased tablet size;
(17) improved blend uniformity;
(18) improved dose uniformity;
(19) increased granule density for wet granulated compositions;
(20) reduced water requirements for wet granulation;
(21) reduced wet granulation time; and/or
(22) reduced drying time for wet granulated mixtures.

Micronized Eplerenone

Although the pharmaceutical compositions are effective for broad range of particle sizes for the initial eplerenone starting material used in the compositions, it has been discovered that reduction of the particle size to a $D_{90}$ particle size of about 25 to about 400 microns can improve eplerenone bioavailability. Eplerenone particles having a $D_{90}$ particle size of about 25 to about 400 microns are referred to herein as micronized eplerenone or micronized eplerenone particles.

Accordingly, the $D_{90}$ particle size (that is, the particle size of at least 90% of the particles) of the eplerenone used as a starting material in the composition is less than about 400 microns, preferably less than about 200 microns, more preferably less than about 150 microns, still more preferably less than about 100 microns, and still more preferably less than 90 microns. A particularly preferred $D_{90}$ particle size is about 30 to about 110 microns, and more particularly still about 30 to about 50 microns. In other preferred embodiments, a particularly preferred $D_{90}$ particle size is about 50 to about 150 microns, and more preferably about 75 to about 125 microns. Micronized eplerenone so sized also typically exhibits a $D_{10}$ particle size of less than 10 microns. For example, as illustrated in Example 30, reducing the $D_{90}$ particle size of the starting material eplerenone from about 220 microns to about 90 microns can materially improve the bioavailability of the pharmaceutical composition.

Eplerenone Dosage of Pharmaceutical Composition

The pharmaceutical compositions of the present invention comprise micronized eplerenone in an amount of about 10 mg to about 1000 mg. Preferably, the pharmaceutical compositions comprise micronized eplerenone in an amount of about 20 mg to about 400 mg, more preferably from about 25 mg to about 200 mg, and still more preferably from about 25 mg to about 150 mg.

Treatment of Specific Conditions and Disorders

The pharmaceutical compositions of the present invention are useful where administration of an aldosterone receptor blocker is indicated. It has been found that these compositions are particularly effective in the treatment of cardiovascular diseases such as heart failure; hypertension (especially the management of mild to moderate hypertension); edema associated with liver insufficiency; post-myocardial infarction; cirrhosis of the liver; stroke prevention; and reduction of heart rate for subjects exhibiting an accelerated heart rate.

For the treatment of heart failure, the pharmaceutical composition preferably provides a daily dosage of eplerenone in the amount of about 25 mg to about 200 mg, more preferably about 25 mg to about 75 mg, and still more preferably about 50 mg. A daily dose of about 0.33 to 2.67 mg/kg body weight (based upon an average body weight of about 75 kg), preferably between about 0.33 and about 1.00 mg/kg body weight and most preferably 0.67 mg/kg body weight, may be appropriate. The daily dose can be administered in one to four doses per day, preferably one dose per day.

For the treatment of hypertension, the pharmaceutical composition preferably provides a daily dosage of eplerenone in the amount of about 50 mg to about 300 mg, more preferably about 50 mg to about 150 mg, and still more preferably about 100 mg. A daily dose of about 0.67 to 4.00 mg/kg body weight, preferably between about 0.67 and about 2.00 mg/kg body weight and most preferably about 1.33 mg/kg body weight, may be appropriate. The daily dose can be administered in one to four doses per day, preferably one dose per day.

For the treatment of edema associated with liver insufficiency, the pharmaceutical composition preferably provides a daily dosage of eplerenone in the amount of about 50 mg to about 500 mg, more preferably about 100 mg to 400 about mg, and still more preferably about 300 mg. A daily dose of about 0.67 to 6.67 mg/kg body weight, preferably between about 1.33 and about 5.33 mg/kg body weight and most preferably about 4.00 mg/kg body weight, may be appropriate. The daily dose can be administered in one to four doses per day, preferably one dose per day.

It has been found that the pharmaceutical compositions of the present invention provide a therapeutic effect as aldosterone receptor blockers in humans over an interval of about 12 to 24 hours, preferably about 24 hours, after oral administration.

In general, the pharmaceutical compositions of the present invention provide a daily dosage of eplerenone sufficient to cause an increase in blood serum renin and aldosterone concentrations in humans over an interval of about 12 to 24 hours, preferably about 24 hours, after oral administration. Specifically, these compositions provide a daily dosage of eplerenone sufficient to cause an average increase in blood serum renin concentration over an interval of about 12 to 24 hours, preferably about 24 hours, after ingestion of the composition of at least about 10%. Similarly, these compositions provide a daily dosage of eplerenone sufficient to cause an average increase in blood serum aldosterone concentrations over an interval of about 12 to 24 hours, preferably about 24 hours, after ingestion of the composition of at least about 50%.

It also has been found that the pharmaceutical compositions of the present invention provide a daily dosage of eplerenone sufficient to cause an average increase in the urinary $\log_{10}$ (sodium/potassium) ratio in humans over an interval of about 12 to 24 hours, preferably about 24 hours, after ingestion of the composition.

It also has been found that the pharmaceutical compositions of the present invention provide a daily dosage of eplerenone sufficient to cause an average decrease in diasystolic blood pressure in humans over an interval of about 12 to 24 hours, preferably about 24 hours, after ingestion of the composition of at least about 5%.

Unit Dosages

Dosage unit forms of the pharmaceutical compositions can typically contain, for example, 10, 20, 25, 37.5, 50, 75, 100, 125, 150, 175, 200, 250, 300, 350 or 400 mg of eplerenone. Preferred dosage unit forms contain about 25, 50, 100, or 150 mg of micronized eplerenone. The dosage unit form can be selected to accommodate the desired frequency of administration used to achieve the specified daily dosage. The amount of the unit dosage form of the pharmaceutical composition that is administered and the dosage regimen for treating the condition or disorder depends on a variety of factors, including the age, weight, sex and medical condition of the subject, the severity of the condition or disorder, the route and frequency of administration, and thus can vary widely, as is well known.

It has been discovered, however, that the efficacy of the required daily dosage of the pharmaceutical compositions of the present invention does not appear to materially differ for once-a-day is administration relative to twice-a-day administration with respect to the compositions described in this application. While not wishing to be bound by theory, it is hypothesized that the compositions of the present invention deliver an amount of eplerenone sufficient to inhibit a protracted genomic response caused by aldosterone binding to the aldosterone receptor site. Interruption of aldosterone binding by eplerenone prevents aldosterone-induced gene product synthesis resulting in an extended period of functional aldosterone receptor blockade that does not require a sustained plasma eplerenone concentration. Accordingly, once-a-day administration is preferred for such tablets for convenience of administration.

Preparation of Eplerenone

The eplerenone of the novel pharmaceutical compositions of the present invention can be prepared using the methods set forth in Grob et al., U.S. Pat. No. 4,559,332 and Ng et al., WO 98/25948, particularly scheme 1 set forth in Ng. et al., WO 98/25948, both of whose disclosures are incorporated by reference.

Form of Pharmaceutical Compositions

The pharmaceutical compositions of the present invention comprise micronized eplerenone in association with one or more non-toxic, pharmaceutically-acceptable carriers, excipients and/or adjuvants (collectively referred to herein as "carrier materials"). The carrier materials are acceptable in the sense of being compatible with the other ingredients of the composition and are not deleterious to the recipient. The pharmaceutical compositions of the present invention can be adapted for administration by any suitable route by selection of appropriate carrier materials and a dosage of eplerenone effective for the treatment intended. For example, these compositions can be prepared in a form suitable for administration orally, intravascularly, intraperitoneally, subcutaneously, intramuscularly (IM) or rectally. Accordingly, the carrier material employed can be a solid or a liquid, or both, and is preferably formulated with the compound as a unit-dose composition, for example, a tablet, which can contain from about 1% to about 95%, preferably about 10% to about 75%, more preferably about 20% to about 60%, and still more preferably about 20% to about 40%, by weight of micronized eplerenone. Such pharmaceutical compositions of the invention can be prepared by any of the well known techniques of pharmacy, consisting essentially of admixing the components.

Oral Administration

For oral administration, the pharmaceutical composition can contain a desired amount of micronized eplerenone and be in the form of, for example, a tablet, a hard or soft capsule, a lozenge, a cachet, a dispensable powder, granules, a suspension, an elixir, a liquid, or any other form reasonably adapted for oral administration. Such a pharmaceutical composition is preferably made in the form of a discrete dosage unit containing a predetermined amount of eplerenone, such as tablets or capsules. Such oral dosage forms can further comprise, for example, buffering agents. Tablets, pills and the like additionally can be prepared with enteric coatings. Unit dosage tablets or capsules are preferred.

Pharmaceutical compositions suitable for buccal (sublingual) administration include, for example, lozenges comprising eplerenone in a flavored base, such as sucrose, and acacia or tragacanth, and pastilles comprising eplerenone in an inert base such as gelatin and glycerin or sucrose and acacia.

Liquid dosage forms for oral administration an include pharmaceutically acceptable emulsions, solutions, suspensions, syrups, and elixirs containing inert diluents commonly used in the art, such as water. Such compositions can also comprise, for example, wetting agents, emulsifying and suspending agents, and sweetening, flavoring, and perfuming agents.

Examples of suitable liquid dosage forms include, but are not limited, aqueous solutions comprising eplerenone and β-cyclodextrin or a water soluble derivative of β-cyclodextrin such as sulfobutyl ether β-cyclodextrin; heptakis-2,6-di-O-methyl-β-cyclodextrin; hydroxypropyl-β-cyclodextrin; and dimethyl-β-cyclodextrin.

Administration By Injection

The pharmaceutical compositions of the present invention can also be administered by injection (intravenous, intramuscular, subcutaneous or jet). Such injectable compositions can employ, for example, saline, dextrose, or water as a suitable carrier material. The pH value of the composition can be adjusted, if necessary, with suitable acid, base, or buffer. Suitable bulking, dispersing, wetting or suspending agents, including mannitol and polyethylene glycol (such as PEG 400), can also be included in the composition. A suitable parenteral composition can also include eplerenone in injection vials. Aqueous solutions can be added to dissolve the composition prior to injection.

Rectal Administration

The pharmaceutical compositions can be administered in the form of a suppository or the like. Such rectal formulations preferably contain micronized eplerenone in a total amount of, for example, 0.075 to 30% w/w, preferably 0.2 to 20% w/w and most preferably 0.4 to 15% w/w. Carrier materials such as cocoa butter, theobroma oil, and other oil and polyethylene glycol suppository bases can be used in such compositions. Other carrier materials such as coatings (for example, hydroxypropyl methylcellulose film coating) and disintegrants (for example, croscarmellose sodium and cross-linked povidone) can also be employed if desired.

As indicated above, these pharmaceutical compositions can be prepared by any suitable method of pharmacy which includes the step of bringing into association eplerenone and the carrier material or carriers materials. In general, the compositions are prepared by uniformly and intimately admixing the active compound with a liquid or finely divided solid carrier, or both, and then, if necessary, shaping the product. For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binding agent, lubricant, inert diluent and/or surface active/dispersing agent(s). Molded tablets can be made by molding, in a suitable machine, the powdered compound moistened with an inert liquid diluent.

Carrier Materials

As noted above, for therapeutic purposes, the pharmaceutical compositions of the present invention comprise micronized eplerenone in a desired amount in combination with one or more pharmaceutically-acceptable carrier materials appropriate to the indicated route of administration. Oral dosage forms of the pharmaceutical compositions of the present invention preferably comprise micronized eplerenone in a desired amount admixed with one or more carrier materials selected from the group consisting of diluents, disintegrants, binding agents and adhesives, wetting agents, lubricants, anti-adherent agents and/or other carrier materials. More preferably, such compositions are tableted or encapsulated for convenient administration. Such capsules or tablets can be in the form of immediate release capsules or tablets, or can contain a controlled-release formulation as can be provided, for example, in a dispersion of eplerenone in hydroxypropyl methylcellulose.

Injectable dosage forms preferably are adapted for parenteral injection. Preferably, these dosage forms comprise micronized eplerenone in aqueous or non-aqueous isotonic sterile injection solutions or suspensions, such as eplerenone suspended or dissolved in water, polyethylene glycol, propylene glycol, ethanol, corn oil, cottonseed oil, peanut oil, sesame oil, benzyl alcohol, sodium chloride, and/or various buffers. These solutions and suspensions can be prepared from sterile powders or granules having one or more of the carriers or diluents mentioned for use in the formulations for oral administration.

The selection and combination of carrier materials used in the pharmaceutical compositions of the present invention provides compositions exhibiting improved performance with respect to, among other properties, efficacy, bioavailability, clearance times, stability, compatibility of eplerenone and carrier materials, safety, dissolution profile, disintegration profile and/or other pharmacokinetic, chemical and/or physical properties. The carrier materials preferably are water soluble or water dispersible and have wetting properties to offset the low aqueous solubility and hydrophobicity of eplerenone. Where the composition is formulated as a tablet, the combination of carrier materials selected provides tablets that can exhibit, among other properties, improved dissolution and disintegration profiles, hardness, crushing strength, and/or friability.

Diluents

The pharmaceutical compositions of the present invention optionally can comprise one or more diluents as a carrier material. Suitable diluents can include, either individually or in combination, such diluents as lactose USP; lactose USP, anhydrous; lactose USP, spray dried; starch USP; directly compressible starch; mannitol USP; sorbitol; dextrose monohydrate; microcrystalline cellulose NF; dibasic calcium phosphate dihydrate NF; sucrose-based diluents; confectioner's sugar; monobasic calcium sulfate monohydrate; calcium sulfate dihydrate NF; calcium lactate trihydrate granular NF; dextrates NF (e.g., Emdex™); Celutab™; dextrose (e.g., Cerelose™); inositol; hydrolyzed cereal solids such as the Maltrons™ and Mor-Rex™; amylose; Rexcel™; powdered cellulose (e.g., Elcema™); calcium carbonate; glycine; bentonite; polyvinylpyrrolidone; and the like. The present pharmaceutical compositions comprise one or more diluents in the range of about 5% to about 99%, preferably about 25% to about 90%, and more preferably about 40% to about 80%, of the total weight of the composition. The diluent or diluents selected preferably exhibit suitable compressibility and pre-compression flow properties.

Microcrystalline cellulose (e.g. Avicel® PH 101) and lactose, either individually or in combination (both diluents are present), are preferred diluents. Both diluents are chemically compatible with micronized eplerenone. The use of extragranular microcrystalline cellulose (that is, microcrystalline cellulose added to a wet granulated composition after the drying step) in addition to intragranular microcrystalline cellulose (that is, microcrystalline cellulose added to the composition during or before the wet granulation step) can be used to improve tablet hardness and/or disintegration time. Lactose, especially lactose monohydrate, is particularly preferred. Lactose typically provides pharmaceutical compositions having suitable eplerenone release rates, stability, pre-compression flowability, and drying properties at a relatively low diluent cost.

Disintegrants

The pharmaceutical compositions of the present invention optionally can comprise one or more disintegrants as a carrier material, particularly for tablet formulations. Suitable disintegrants can include, either individually or in combination, such disintegrants as starches; sodium starch glycolate; clays (such as Veegum™ HV); celluloses (such as purified cellulose, methylcellulose and sodium carboxymethylcellulose, and carboxymethylcellulose); alginates; pregelatinized corn starches (such as National™ 1551 and National™ 1550); crospovidone USP NF; gums (such as agar, guar, locust bean, Karaya™, pectin, and tragacanth). Disintegrants can be added at any suitable step during the preparation of the pharmaceutical composition, particularly prior to granulation or during the lubrication step prior to compression. The present pharmaceutical compositions comprise one or more disintegrants in the range of about 0.5% to about 30%, preferably about 1% to about 10%, and more preferably about 2% to about 6%, of the total weight of the composition.

Croscarmellose sodium is a preferred disintegrant for tablet formulations, preferably in the range of about 1% to about 10%, preferably about 2% to about 6%, and more preferably about 5%, by weight of the composition.

Binding Agents and Adhesives

The pharmaceutical compositions of the present invention optionally can comprise one or more binding agents or adhesives as a carrier material. Such binding agents and adhesives preferably impart sufficient cohesion to the powders to permit normal processing such as sizing, lubrication, compression and packaging, but still permit the tablet to disintegrate and the composition to dissolve upon ingestion. Suitable binding agents and adhesives include, either individually or in combination, such binding agents and adhesives as acacia; tragacanth; sucrose; gelatin; glucose; starch; cellulose materials such as, but not limited to, methylcellulose and sodium carboxymethylcellulose (e.g., Tylose™); alginic acid and salts of alginic acid; magnesium aluminum silicate; polyethylene glycol; guar gum; polysaccharide acids; bentonites; polyvinylpyrrolidone (povidone); polymethacrylates; hydroxypropyl methylcellulose (HPMC); hydroxypropyl cellulose (Klucel™); ethyl cellulose (Ethocel™); pregelatinized starch (such as National™ 1511 and Starch 1500). The present pharmaceutical compositions comprise one or more binding agents and/or adhesives in the range of about 0.5% to about 25%, preferably about 0.75% to about 15%, and more preferably about 1% to about 10%, of the total weight of the composition.

Hydroxypropyl methylcellulose is a preferred binding agent used impart cohesive properties to the powder blend of the eplerenone formulation. The compositions preferably comprise hydroxypropyl methylcellulose as a binding agent in a range of about 0.5% to about 10%, more preferably about 1% to about 8%, and still more preferably about 2% to about 4%, of the total weight of the composition. Low molecular weight hydroxypropyl methylcellulose having a viscosity of about 2 cps to about 8 cps typically can be used, although viscosities of about 2 cps to about 6 cps are preferred, particularly viscosities of about 2 cps to about 4 cps. Viscosities are measured as a 2 percent solution in water at 20° C. Methoxy content of the hydroxypropyl methylcellulose typically is about 15% to about 35%, whereas hydroxypropyl content is typically up to about 15%, preferably about 2% to about 12%.

Wetting Agents

Eplerenone, even micronized eplerenone, is largely insoluble in aqueous solution. Accordingly, the pharmaceutical compositions of the present invention optionally can comprise one or more wetting agents as a carrier material, particularly for tablet formulations. Such wetting agents preferably maintain eplerenone in solution and improve the bioavailability of the pharmaceutical composition. Suitable wetting agents include, either individually or in combination, such wetting agents as oleic acid; glyceryl monostearate; sorbitan monooleate; sorbitan monolaurate; triethanolamine oleate; polyoxyethylene sorbitan monooleate; polyoxyethylene sorbitan monolaurate; sodium oleate; and sodium lauryl sulfate. Wetting agents that are anionic surfactants are preferred. The present pharmaceutical compositions comprise one or more wetting agents present at about 0.1% to about 15%, preferably about 0.25% to about 10%, and more preferably about 0.5% to about 5%, of the total weight of the composition.

Sodium lauryl sulfate is a preferred wetting agent for tablet formulations. The compositions of the present invention preferably comprise sodium lauryl sulfate as the wetting agent at about 0.25% to about 7%, more preferably about 0.4% to about 4%, and still more preferably about 0.5 to about 2%, of the total weight of the composition.

Lubricants

The pharmaceutical compositions of the present invention optionally comprises one or more lubricants and/or glidants as a carrier material. Suitable lubricants and/or glidants include, either individually or in combination, such lubricants and/or glidants as glyceryl behenate (Compritol™ 888); metalllic stearates (e.g., magnesium, calcium and sodium stearates); stearic acid; hydrogenated vegetable oils (e.g., Sterotex™); talc; waxes; Stearowet™; boric acid; sodium benzoate and sodium acetate; sodium chloride; DL-Leucine; polyethylene glycols (e.g., Carbowax™ 4000 and Carbowax™ 6000); sodium oleate; sodium benzoate; sodium acetate; sodium lauryl sulfate; sodium stearyl fumarate (Pruv™); and magnesium lauryl sulfate. The present pharmaceutical compositions comprise one or more lubricants at about 0.1% to about 10%, preferably about 0.2% to about 8%, and more preferably about 0.25% to about 5%, of the total weight of the composition.

Magnesium stearate is a preferred lubricant used to reduce friction between the equipment and granulation during compression.

Anti-Adherent Agents or Glidants

The pharmaceutical compositions of the present invention optionally can comprise one or more anti-adherent agents or glidants as a carrier material. Suitable anti-adherents or glidants include, either individually or in combination, such anti-adherents as talc, cornstarch, Cab-O-Sil™, Syloid™, DL-Leucine, sodium lauryl sulfate, and metallic stearates. The present pharmaceutical compositions comprise one or more anti-adherents or glidants at about 0.1% to about 15%, preferably about 0.25% to about 10%, and more preferably about 0.5% to about 5%, of the total weight of the composition.

Talc is a preferred anti-adherent or glidant agent used to reduce formulation sticking to equipment surfaces and also to reduce static in the blend. The compositions preferably comprise talc at about 0.1% to about 10%, more preferably about 0.25% to about 5%, and still more preferably about 0.5% to about 2%, of the total weight of the composition.

Other carrier materials (such as colorants, flavors and sweeteners) and modes of administration are known in the pharmaceutical art and can be used in the preparation of the pharmaceutical compositions of the present invention. Tablets can be coated or uncoated.

In one embodiment of the present invention, the pharmaceutical compositions comprise micronized eplerenone in a desired amount and one or more cellulosic carrier materials. The term "cellulosic carrier materials" embraces carrier materials comprising cellulose or a cellulose derivative such as purified cellulose; microcrystalline cellulose; and alkyl celluloses and their derivatives and salts (e.g., methylcellulose, sodium carboxymethyl-cellulose, carboxymethylcellulose, croscarmellose sodium, hydroxypropyl cellulose, hydroxypropyl methylcellulose and the like). Preferably, at least one carrier material is a cellulosic material selected from the group consisting of $C_1$–$C_6$-alkyl celluloses and their derivatives and salts. Still more preferably, this cellulosic material is selected from the group consisting of hydroxyalkyl alkylcelluloses and their derivatives and salts. Still more preferably, this cellulosic material is selected from the group consisting of hydroxy($C_2$–$C_4$-alkyl) ($C_1$–$C_4$-alkyl)celluloses and their derivatives and salts.

These pharmaceutical compositions comprising micronized eplerenone in a desired amount and one or more cellulosic carrier materials preferably further comprise one or more carrier materials selected from the group consisting of diluents, disintegrants, binding agents, wetting agents, lubricants and anti-adherent agents. More preferably, these pharmaceutical compositions comprise one or more carrier materials selected from the group consisting of lactose, microcrystalline cellulose, croscarmellose sodium, hydroxypropyl methylcellulose, sodium lauryl sulfate, magnesium stearate, and talc. Still more preferably, these pharmaceutical compositions comprise lactose monohydrate, microcrystalline cellulose, croscarmellose sodium, and hydroxypropyl methylcellulose. Still more preferably, these pharmaceutical compositions further comprise one or more of the carrier materials sodium lauryl sulfate, magnesium stearate, and talc.

The individual pharmaceutically acceptable carrier materials described in the above embodiment optionally can be replaced with other suitable carrier materials if desired. Acceptable substitute carrier materials are chemically compatible both with eplerenone and with the other carrier materials. Although other diluents, disintegrants, binding agents and adhesives, wetting agents, lubricants and/or anti-adherent or glidant agents can be employed, it has been discovered, however, that the pharmaceutical compositions comprising micronized eplerenone, lactose, microcrystalline cellulose, croscarmellose sodium, and hydroxypropyl methylcellulose, and, optionally, sodium lauryl sulfate, magnesium stearate, and/or talc possess a superior combination of pharmacokinetic, chemical and/or physical properties relative to such other compositions.

In another embodiment, the pharmaceutical composition comprises:
  about 1 to about 95 weight percent of micronized eplerenone;
  about 5 to about 99 weight percent of a pharmaceutically acceptably diluent;
  about 0.5 to about 30 weight percent of a pharmaceutically acceptably disintegrant; and
  about 0.5 to about 25 weight percent of a pharmaceutically acceptably binding agent.
These pharmaceutical compositions optionally can additionally comprise about 0.25 to about 15 weight percent of a pharmaceutically acceptably wetting agent; about 0.1 to about 10 weight percent of a pharmaceutically acceptably lubricant; about 0.1 to about 15 weight percent of a pharmaceutically acceptably anti-adherent agent.

The term "weight percent" as used herein means the weight percent of a specified ingredient based upon the total weight of all ingredients of the composition.

In still another embodiment, the pharmaceutical composition comprises micronized eplerenone and a cellulosic carrier material wherein the compositions are in oral dosage form, preferably tablets or capsules. Preferably, the composition further comprises one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the composition be present in the amounts or the weight fractions set forth below.

In still another embodiment, the pharmaceutical compositions are in the form of unit dosage tablets or capsules.

In still another embodiment, the pharmaceutical compositions comprise micronized eplerenone and one or more carrier materials in the form of an oral unit dosage suitable for once-a-day or twice-a-day oral administration. Still more preferably, these pharmaceutical compositions comprise micronized eplerenone and one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the composition be present in the amounts or the weight fractions set forth below.

In still another embodiment, the pharmaceutical compositions comprise micronized eplerenone and one or more carrier materials that when orally administered to a human patient in need thereof provide a therapeutic effect as an aldosterone receptor blocker over an interval of about 12 to about 24 hours, preferably at least about 24 hours, after oral administration. Still more preferably, these pharmaceutical compositions comprise micronized eplerenone and one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the composition be present in the amounts or the weight fractions set forth below.

In still another embodiment, the pharmaceutical compositions comprise micronized eplerenone and one or more carrier materials that when orally administered to a human patient in need thereof cause an average increase in blood serum renin concentration over an interval of about 12 to 24 hours, preferably about 24 hours, after ingestion of the composition of at least about 10%. Still more preferably, these pharmaceutical compositions comprise micronized eplerenone and one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the composition be present in the amounts or the weight fractions set forth below.

In still another embodiment, the pharmaceutical compositions comprise micronized eplerenone and one or more carrier materials that when orally administered to a human patient in need thereof cause an average increase in blood serum aldosterone concentration over an interval of about 12 to 24 hours, preferably about 24 hours, after ingestion of the composition of at least about 50%. Still more preferably, these pharmaceutical compositions comprise micronized eplerenone and one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the composition be present in the amounts or the weight fractions set forth below.

In yet another embodiment, the pharmaceutical compositions comprise micronized eplerenone and one or more carrier materials that when orally administered to a human patient in need thereof cause an average decrease in diastolic blood pressure over an interval of about 12 to 24 hours, preferably about 24 hours, after ingestion of the composition of at least about 5%. Still more preferably, these pharmaceutical compositions comprise micronized eplerenone and one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the composition be present in the amounts or the weight fractions set forth below.

In still another embodiment, the pharmaceutical compositions comprise micronized eplerenone and one or more carrier materials that when orally administered to a human patient in need thereof cause an average increase in the urinary $\log_{10}$ (sodium/potassium) ratio over an interval of about 12 to 24 hours, preferably about 24 hours, after ingestion of the composition. Still more preferably, these pharmaceutical compositions comprise micronized eplerenone and one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the composition be present in the amounts or the weight fractions set forth below.

Immediate Release Formulations

Oral delivery of the pharmaceutical compositions of the present invention can include immediate release compositions as well as controlled release compositions. Preferably, the pharmaceutical compositions are in the form of immediate release tablets or capsules. The immediate release compositions comprise micronized eplerenone in an amount sufficient to provide the desired daily dosage of eplerenone, that is, an amount of about 10 mg to about 1000 mg, more preferably an amount of about 20 mg to 400 mg, still more preferably an amount of about 25 mg to 200 mg, still more preferably an amount of about 25 mg to 150 mg, and still more preferably an amount of about 50 mg to 100 mg. A once-a-day immediate release tablet or capsule contains eplerenone in an amount, for example, of about 50 mg to about 100 mg. Preferably, the same batch can be used to prepare tablets (or capsules) of different strengths by compressing the formulation in different tablet sizes (or encapsulating the formulation in different capsule sizes or using different capsule fill weights). Although the amount of eplerenone in such novel compositions preferably is within the ranges previously discussed, the formulations also can be useful for the administration of an amount of eplerenone falling outside of the disclosed dosage ranges.

Dissolution Profile

The compositions of the present invention preferably are immediate release compositions from which about 50% of the micronized eplerenone is dissolved in vitro within about 15 minutes, more preferably at least about 80% of the eplerenone eplerenone is dissolved in vitro within about 30 minutes, and still more preferably at least about 90% of the eplerenone is dissolved in vitro within about 45 minutes using 1% sodium dodecyl sulfate (SDS) in water as the dissolution medium at 37° C. in the dissolution assay discussed hereinafter. More preferably, 0.1 N HCl in water at 37° C. is the in vitro dissolution medium in that assay, and about 50% of the micronized eplerenone is dissolved in about 20 minutes, about 80% is dissolved at about 45 minutes and greater than about 90% is dissolved in about 90 minutes. More preferably, about 50% of the micronized eplerenone is dissolved in about 15 minutes, about 80% is dissolved at about 30 minutes and about 90% or more is dissolved in about 45 minutes.

Disintegration Profile

Carrier materials for immediate release compositions preferably are selected to provide a disintegration time less than about 30 minutes, preferably about 20 minutes or less, more preferably about 18 minutes or less, and still more preferably about 14 minutes or less.

Granulation Particle Size and Flow Properties

Although the pharmaceutical compositions of the present invention can be prepared, for example, by direct encapsulation or direct compression, they preferably are wet granulated prior to encapsulation or compression. Wet granulation, among other matters, densifies the compositions resulting in improved flow properties, improved compression characteristics and easier metering or weight dispensing of the final compositions. The average particle size of the granulation preferably permits for convenient handling and processing and, for tablets, permits the formation of a directly compressible mixture that forms pharmaceutically acceptable tablets. The desired tap and bulk densities of the granulation are normally about 0.3 g/ml to about 1.0 g/ml, preferably about 0.4 g/ml to about 0.8 g/ml.

Hardness

For tablet formulations, the pharmaceutical composition in an amount sufficient to make a uniform batch of tablets is subjected to tableting in a conventional production scale tableting machine at normal compression pressure (for example, about 1 kN to about 50 kN). Any tablet hardness convenient with respect to handling, manufacture, storage and ingestion may be employed. Hardness in the range of about 3.5 kP to about 22 kP is typically acceptable, with about 3.5 kP to about 9 kP preferred for 25 mg tablets, about 5 kP to about 13 kP preferred for 50 mg tablets, and about 8 kP to about 22 kP preferred for 100 mg tablets. The mixture, however, is not be compressed to such a degree that there is subsequent difficulty in achieving hydration when exposed to gastric fluid.

Friability

For tablet formulations, tablet friability preferably is less than about 0.8%, more preferably less than 0.4%.

Preferred Compositions

Preferably, the pharmaceutical compositions of this embodiment comprise:

about 1 to about 90 weight percent of micronized eplerenone;

about 5 to about 90 weight percent of lactose;

about 5 to about 90 weight percent of microcrystalline cellulose; and about 0.5 to about 10 weight percent of hydroxypropyl methylcellulose.

These pharmaceutical compositions optionally can additionally comprise about 1 to about 10 weight percent of croscarmellose sodium; about 0.1 to about 7 weight percent of sodium lauryl sulfate; about 0.1 to about 10 weight percent of talc; and/or about 0.1 to about 10 weight percent of magnesium stearate.

More preferably, the pharmaceutical compositions of this embodiment comprise:
- about 19 to about 40 weight percent of micronized eplerenone;
- about 32 to about 52 weight percent of lactose;
- about 8 to about 28 weight percent of microcrystalline cellulose;
- about 1 to about 10 weight percent of croscarmellose sodium; and
- about 1 to about 8 weight percent of hydroxypropyl methylcellulose.

These pharmaceutical compositions optionally can additionally comprise about 0.1 to about 7 weight percent of sodium lauryl sulfate; about 0.1 to about 10 weight percent of talc; and about 0.1 to about 10 weight percent of magnesium stearate. Preferably, the hydroxypropyl methylcellulose has a viscosity of from about 2 cps to about 8 cps, more preferably about 2 cps to about 6 cps, as noted before. The compositions are preferably in the form of unit dosage tablets.

Still more preferably, the pharmaceutical compositions of this embodiment comprise:
- about 24 to about 35 weight percent of micronized eplerenone;
- about 37 to about 47 weight percent of lactose;
- about 13 to about 23 weight percent of microcrystalline cellulose;
- about 2 to about 6 weight percent of croscarmellose sodium; and
- about 2 to about 4 weight percent of hydroxypropyl methylcellulose.

These pharmaceutical compositions optionally can additionally comprise about 0.25 to about 4 weight percent of sodium lauryl sulfate; about 0.1 to about 5 weight percent of talc; and about 0.25 to about 5 weight percent of magnesium stearate. Preferably, the hydroxypropyl methylcellulose has a viscosity of from about 2 cps to about 6 cps, as before.

Still more preferably, the pharmaceutical compositions of this embodiment comprise:
- about 28 to about 31 weight percent of micronized eplerenone;
- about 41 to about 43 weight percent of lactose monohydrate;
- about 17 to about 19 weight percent of microcrystalline cellulose;
- about 4.5 to about 5.5 weight percent of croscarmellose sodium; and
- about 2.5 to about 3.5 weight percent of hydroxypropyl methylcellulose.

These pharmaceutical compositions optionally can additionally comprise about 0.5 to about 1.5 weight percent of sodium lauryl sulfate; about 0.5 to about 1.5 weight percent of talc; and about 0.25 to about 0.75 weight percent of magnesium stearate. Preferably, the hydroxypropyl methylcellulose has a viscosity of from about 2 cps to about 4 cps, as before.

Still more preferably, the pharmaceutical compositions of this embodiment are in the form of a coated or uncoated unit dosage tablet wherein the uncoated tablet or the coated tablet prior to coating comprise:

- about 29.4 weight percent of micronized eplerenone;
- about 42 weight percent of lactose;
- about 18.1 weight percent of microcrystalline cellulose;
- about 5 weight percent of croscarmellose sodium;
- about 3 weight percent of hydroxypropyl methylcellulose;
- about 1 weight percent of sodium lauryl sulfate;
- about 1 weight percent of talc; and
- about 0.5 weight percent of magnesium stearate.

In another embodiment, the pharmaceutical compositions of this embodiment comprise:
- about 20 mg to about 110 mg of micronized eplerenone;
- about 30 mg to about 150 mg of lactose;
- about 10 mg to about 70 mg of microcrystalline cellulose; and
- about 1 mg to about 15 mg of hydroxypropyl methylcellulose.

These pharmaceutical compositions optionally can additionally comprise about 1 mg to about 25 mg of croscarmellose sodium; about 0.25 mg to about 5 mg of sodium lauryl sulfate; about 0.5 mg to about 5 mg of talc; and about 0.5 mg to about 3 mg of magnesium stearate. Preferably, the hydroxypropyl methylcellulose has a viscosity of from about 2 cps to about 8 cps, more preferably about 2 cps to about 6 cps, as discussed before.

In another embodiment, the pharmaceutical compositions of this embodiment comprise:
- about 23 to about 27 mg of micronized eplerenone;
- about 34 mg to about 38 mg of lactose;
- about 14 mg to about 17 mg of microcrystalline cellulose;
- about 3 mg to about 6 mg of croscarmellose sodium; and
- about 1 mg to about 4 mg of hydroxypropyl methylcellulose.

These pharmaceutical compositions optionally can additionally comprise about 0.25 mg to about 1.5 mg of sodium lauryl sulfate; about 0.25 mg to about 1.5 mg of talc; and about 0.1 mg to about 1 mg of magnesium stearate. Preferably, the hydroxypropyl methylcellulose has a viscosity of from about 2 cps to about 6 cps, as before. The compositions are preferably in the form of unit dosage tablets.

In another embodiment, the pharmaceutical compositions of this embodiment comprise:
- about 48 mg to about 52 mg of micronized eplerenone;
- about 70 mg to about 73 mg of lactose;
- about 29 mg to about 33 mg of microcrystalline cellulose;
- about 6 mg to about 10 mg of croscarmellose sodium; and
- about 4 mg to about 6 mg of hydroxypropyl methylcellulose.

These pharmaceutical compositions optionally can additionally comprise about 1 to about 2.5 mg of sodium lauryl sulfate; about 1 to about 2.5 mg of talc; and about 0.5 mg to about 1.5 mg of magnesium stearate. Preferably, the hydroxypropyl methylcellulose has a viscosity of from about 2 cps to about 6 cps, as before. The compositions are preferably in the form of unit dosage tablets.

In another embodiment, the pharmaceutical compositions of this embodiment comprise:
- about 98 mg to about 102 mg of micronized eplerenone;
- about 141 mg to about 145 mg of lactose;
- about 60 mg to about 64 mg of microcrystalline cellulose;
- about 16 mg to about 18 mg of croscarmellose sodium; and about 9 mg to about 11 mg of hydroxypropyl methylcellulose.

These pharmaceutical compositions optionally can additionally comprise about 3 mg to about 4 mg of sodium lauryl sulfate; about 3 mg to about 4 mg of talc; and about 1 mg to about 2 mg of magnesium stearate. Preferably, the hydroxypropyl methylcellulose has a viscosity of from about 2 cps to about 6 cps, as before. The compositions are preferably in the form of unit dosage tablets.

In another embodiment, the pharmaceutical compositions of this embodiment comprise lactose, microcrystalline cellulose, croscarmellose sodium, hydroxypropyl methylcellulose, sodium lauryl sulfate, talc, and magnesium stearate.

In still another embodiment, the pharmaceutical compositions release in vitro at least 50% of the eplerenone contained in the composition within about 15 minutes in the SDS-containing medium. More preferably, about 50% of the micronized eplerenone is dissolved in about 20 minutes, about 80% is dissolved in about 45 minutes and greater than about 90% is dissolved in about 90 minutes using the 0.1 N HCl solution assay. More preferably still, about 50% of the micronized eplerenone is dissolved in about 15 minutes, about 80% is dissolved at about 30 minutes and about 90% or more is dissolved in about 45 minutes.

In still another embodiment, the pharmaceutical compositions comprise micronized eplerenone and one or more carrier materials in an oral unit dosage form suitable for once-a-day or twice-a-day oral administration and capable of releasing in vitro at least 50% of the eplerenone contained in the composition within about 15 minutes in the SDS-containing medium. More preferably, about 50% of the micronized eplerenone is dissolved in about 20 minutes using the 0.1 N HCl solution assay. More preferably still, about 50% of the micronized eplerenone is dissolved in about 15 minutes, about 80% is dissolved at about 30 minutes and about 90% or more is dissolved in about 45 minutes. Still more preferably, these pharmaceutical compositions comprise eplerenone and one or more carrier materials selected from the group consisting of lactose monohydrate, microcrystalline cellulose, croscarmellose sodium, hydroxypropyl methylcellulose, sodium lauryl sulfate, talc, and magnesium stearate. It is particularly preferred that the various components of the compositions be present in the amounts or the weight fractions set forth above.

In another embodiment, the pharmaceutical compositions of this embodiment comprise:
  about 15 to about 35 weight percent of micronized eplerenone;
  about 48 to about 68 weight percent of lactose;
  about 2 to about 22 weight percent of microcrystalline cellulose; and
  about 0.1 to about 10 weight percent of croscarmellose sodium.

These pharmaceutical compositions optionally can additionally comprise about 0.1 to about 7 weight percent of sodium lauryl sulfate; about 0.1 to about 10 weight percent of talc; about 0.1 to about 10 weight percent of magnesium stearate; and about 0.1 to about 10 weight percent colloidal silicon dioxide. The compositions are preferably in the form of unit dosage capsules.

Still more preferably, the pharmaceutical compositions of this embodiment comprise:
  about 20 to about 30 weight percent of micronized eplerenone;
  about 53 to about 63 weight percent of lactose;
  about 6.5 to about 16.5 weight percent of microcrystalline cellulose; and
  about 0.5 to about 6 weight percent of croscarmellose sodium.

These pharmaceutical compositions optionally can additionally comprise about 0.25 to about 4 weight percent of sodium lauryl sulfate; about 0.5 to about 5 weight percent of talc; and about 0.25 to about 5 weight percent of magnesium stearate; and about 0.1 to about 5 weight percent colloidal silicon dioxide.

Still more preferably, the pharmaceutical compositions of this embodiment comprise:
  about 23 to about 27 weight percent of micronized eplerenone;
  about 56 to about 60 weight percent of lactose monohydrate;
  about 9.5 to about 13.5 weight percent of microcrystalline cellulose; and
  about 0.5 to about 3.5 weight percent of croscarmellose sodium.

These pharmaceutical compositions optionally can additionally comprise about 0.25 to about 1.5 weight percent of sodium lauryl sulfate; about 1 to about 4 weight percent of talc; and about 0.1 to about 1 weight percent of magnesium stearate; and about 0.1 to about 1.5 weight percent colloidal silicon dioxide.

Still more preferably, the pharmaceutical compositions of this embodiment are in the form of a capsule comprising:
  about 25.0 weight percent of micronized eplerenone;
  about 57.9 weight percent of lactose;
  about 11.3 weight percent of microcrystalline cellulose;
  about 2 weight percent of croscarmellose sodium;
  about 0.5 weight percent of sodium lauryl sulfate;
  about 2.5 weight percent of talc;
  about 0.3 weight percent of magnesium stearate; and
  about 0.5 weight percent colloidal silicon dioxide.

In another embodiment, the pharmaceutical compositions of this embodiment comprise:
  about 20 mg to about 110 mg of micronized eplerenone;
  about 48 mg to about 242 mg of lactose; and
  about 2 mg to about 56 mg of microcrystalline cellulose.

These pharmaceutical compositions optionally can additionally comprise about 0.25 mg to about 18 mg of croscarmellose sodium; about 0.1 mg to about 5 mg of sodium lauryl sulfate; about 0.5 mg to about 8 mg of talc; about 0.1 mg to about 5 mg of magnesium stearate; and about 0.1 mg to about 5 mg colloidal silicon dioxide.

In another embodiment, the pharmaceuticals composition of this embodiment comprise:
  about 23 to about 27 mg of micronized eplerenone;
  about 56 mg to about 60 mg of lactose;
  about 9.5 mg to about 13.5 mg of microcrystalline cellulose; and
  about 0.5 mg to about 3.5 mg of croscarmellose sodium.

These pharmaceutical compositions optionally can additionally comprise about 0.1 mg to about 1.5 mg of sodium lauryl sulfate; about 0.25 mg to about 4.5 mg of talc; about 0.1 mg to about 1.5 mg of magnesium stearate; and about 0.1 to about 2.5 weight percent colloidal silicon dioxide. The compositions are preferably in the form of unit dosage capsules.

In another embodiment, the pharmaceutical compositions of this embodiment comprise:

about 48 mg to about 52 mg of micronized eplerenone;
about 114 mg to about 118 mg of lactose;
about 21 mg to about 25 mg of microcrystalline cellulose; and
about 2 mg to about 6 mg of croscarmellose sodium.

These pharmaceutical compositions optionally can additionally comprise about 1 to about 2.5 mg of sodium lauryl sulfate; about 2 to about 8 mg of talc; about 0.25 mg to about 1.5 mg of magnesium stearate; and about 0.1 to about 3 weight percent colloidal silicon dioxide. The compositions are preferably in the form of unit dosage capsules.

In another embodiment, the pharmaceutical compositions of this embodiment comprise:
about 98 mg to about 102 mg of micronized eplerenone;
about 229 mg to about 234 mg of lactose;
about 43 mg to about 48 mg of microcrystalline cellulose; and
about 6 mg to about 10 mg of croscarmellose sodium.

These pharmaceutical compositions optionally can additionally comprise about 0.5 mg to about 4 mg of sodium lauryl sulfate; about 8 to about 12 mg of talc; about 0.5 mg to about 3 mg of magnesium stearate; and about 0.5 mg to about 4 mg colloidal silicon dioxide. The compositions are preferably in the form of unit dosage capsules.

Controlled Release Oral Formulations

Oral delivery of the pharmaceutical compositions of the present invention can include controlled release formulations, including controlled release formulations well known in the art, providing prolonged or sustained delivery of the drug to the gastrointestinal tract by any number of mechanisms. Such prolonged or sustained release mechanisms can include, but are not limited to, pH sensitive release from the dosage form based on the changing pH of the small intestine; slow erosion of a tablet or capsule; retention in the stomach based on the physical properties of the formulation; bioadhesion of the dosage form to the mucosal lining of the intestinal tract; or enzymatic release of eplerenone from the dosage form. The intended effect is to extend the time period over which eplerenone is delivered to the site of action by manipulation of the dosage form. Thus, enteric-coated and enteric-coated controlled release formulations are within the scope of the present invention.

The controlled release compositions comprise micronized eplerenone in a desired amount, preferably in a range as previously discussed above, that is, in an amount of about 10 mg to about 1000 mg, more preferably about 20 mg to 400 mg, still more preferably about 25 mg to 200 mg, and still more preferably about 25 mg to 150 mg. Preferred controlled release compositions are in the form of tablets or capsules, particularly tablets or capsules comprising micronized eplerenone in an amount of 25 mg, 50 mg, 100 mg or 150 mg. The controlled release compositions may or may not be in a single dosage form. Such controlled release compositions, however, preferably are in a unit dose oral form. A once-a-day controlled release tablet or capsule typically comprises eplerenone in a range of about 25 mg to about 150 mg.

A controlled-release dosage form as defined in US Pharmacopeia XXII includes extended release dosage forms that permit at least a two-fold reduction in dosing frequency as compared to the drug presented as a conventional dosage form and delayed release dosage forms which release the drug at a time other than promptly after administration. The controlled release composition can be, and preferably is, a sustained release or delayed/modified release form.

One type of controlled release composition, for example, achieves controlled release by use of a matrix tablet composition. Suitable matrix forming materials are waxes (e.g., carnauba, bees wax, paraffin wax, ceresine, shellac wax, fatty acids, and fatty alcohols); oils, hardened oils or fats (e.g., hardened rapeseed oil, castor oil, beef tallow, palm oil, and soya bean oil); polymers (e.g., hydroxypropyl cellulose, polyvinylpyrrolidone, hydroxypropyl methyl cellulose, polyethylene glycol, methacrylates (PMMA), and carbomer); alginates; xanthum gums; and other carrier materials known to those of ordinary skill in the art. Other suitable matrix tableting materials include, but are not limited to, microcrystalline cellulose, powdered cellulose, hydroxypropyl cellulose, and ethyl cellulose. Other types of controlled release compositions may achieve controlled release by use of granulates, coated powders, pellets, or the like, by use of multi-layering, and/or by used of suitable coatings. Still other controlled release compositions include an osmotic pump (such as described in GB 2207052 published Jan. 25, 1989), or combinations of the above.

Suitable coating materials for use in the preparation of controlled release compositions include, but are not limited to, any pharmaceutically acceptable polymer such as ethyl cellulose, cellulose acetate butyrate, cellulose acetates, polymethacrylates containing quaternary ammonium groups or other pharmaceutically acceptable polymers, polyethylene glycol, hydroxypropyl cellulose, hydroxypropyl methylcellulose, polyvinylpyrrolidone, and polyvinyl alcohol; monomeric materials such as sugars including lactose, sucrose, fructose and mannitol; salts including sodium chloride, potassium chloride and derivatives; organic acids including furmaric acid, succinic acid, lactic acid and tartaric acid and mixtures thereof; enteric polymers including polyvinyl acetate phthalate, cellulose acetate phthalate, cellulose acetate trimellitate, shellac, zein, and polymethacrylates containing carboxyl groups. These polymers can be applied as solutions or latexes. Other barriers may be used such as waxes.

The coating composition can be plasticized according to the properties of the coating blend such as the glass transition temperature of the main component or mixture of components or the solvent used for applying the coating compositions. Suitable plasticizers can be added from about 0% to about 50% by weight of the coating composition. Such plasticizers include, for example, the group consisting of diethyl phthalate, citrate esters, polyethylene glycol, glycerol, acetylated glycerides, and castor oil.

Tablets or capsules containing micronized eplerenone can be coated directly to produce a controlled release dose, or can comprise a plurality of coated cores containing eplerenone. As used herein, the term "core" refers to an element of the composition containing eplerenone and various carrier. Each core can contain an amount of micronized eplerenone in the range of about 0.1% to 95%, preferably about 10% to 80%, by weight based on the total weight of the core. The core typically can be about 200 μm to 1700 μm in diameter. A pellet is a coated core with the coating being any suitable coating.

These controlled release compositions can be made by prilling, spray drying, pan coating, melt granulation, granulation, wurster coating, tangential coating, top spraying, tableting, extruding, coacervation and the like. The particle size of the controlled release components other than micronized eplerenone in the dosage form depends on the technology used. The particle sizes can range from submicron to 500 μm for powder technologies (mixtures, spray drying, dispersions, and the like); 5 μm to 1700 μm for coating technologies (wurster, top spray, bottom spray, spray drying, extrusion, layering, and the like); and 1 mm to 20 mm for tableting technologies. The controlled release forms of micronized eplerenone are then combined into a single dosage such that the amount of eplerenone in the composition of the invention provides the desired dosage. Standard coating procedures, such as those described, for example, in *Remington's Pharmaceutical Sciences*, 18$^{th}$ Edition (1990), can conveniently be used.

The compositions can include micronized eplerenone in an immediate release form in association with micronized eplerenone in a controlled release form. The immediate release form of such compositions can include an amount of micronized eplerenone that is about 0.5% to about 90% of the total amount of eplerenone of the composition, with the controlled release form containing the remainder of the micronized eplerenone. As a result, the final composition provides an amount of micronized eplerenone for immediate release following administration and an additional amount of micronized eplerenone for controlled release.

The following non-limiting example illustrates the uses of the components listed above in producing a composition in accordance with the invention.

Where the composition of the invention is in the form of a pellet product, the pellets can be presented in a sachet, capsule or tablet. The non-limiting example below describes pellets (particle sizes 200 μm to 1700 μm) in a capsule. All the quoted ranges are % w/w.

A plurality of elements containing micronized eplerenone, or cores, are prepared by extrusion/spheronization, or by layering eplerenone (or a blend of eplerenone with other carrier materials) onto inert carriers by various processes. The cores themselves can be immediate release or controlled release depending on the materials and method of manufacture. The cores can contain the micronized drug at the required potency according to the particular eplerenone dose, required size, required presentation, and subsequent processes (coating and the like). The cores can contain micronized eplerenone in the range of about 0.1% to about 100%, depending on the required dose, potency, manufacturing method, and other properties.

An extruded core typically includes micronized eplerenone and, for example, a diluent/disintegrant such microcrystalline cellulose (in the range about 0.5% to about 99.9%), a binding agent such as hydroxypropyl cellulose (in the range about 0.5% to about 50%); a filler such as lactose (in the range of about 0.5% to about 90%); and other carrier materials. An extruded core can, where desired, only contain drug and binding agent.

An extruded core with controlled release properties typically contains micronized eplerenone and a swelling/gelling polymer such as hydroxypropyl cellulose (in the range about 0.5% to about 50%), or a hydrophobic material such as cetyl alcohol (in the range of about 10% to about 90%). A layered core can contain micronized eplerenone and an inert carrier such as a sugar sphere (in the range about 10% to about 90%) with a binding agent (in the range about 0.1% to about 50%). The core can contain diluents, wetting agents and other additives. The binding agent can be chosen to achieve immediate release (such as hydroxypropyl cellulose, hydroxypropyl methylcellulose and the like), controlled release (such as ethyl cellulose, cellulose acetate butyrate and the like), or delayed/modified release (for example, enteric binding materials such as hydroxypropyl methylcellulose phthalate, polyvinyl acetate phthalate and the like).

A portion of the final dosage form can be immediate release cores made by the above described processes. Alternatively, the immediate release cores can be coated with a rapidly disintegrating or dissolving coat for aesthetic, handling, or stability purposes. Suitable materials include polyvinylpyrrolidone, hydroxypropyl cellulose, hydroxypropyl methylcellulose, polyethylene glycol, and polymethacrylates containing free amino groups. Such materials can include plasticizers, antitack agents and/or diluents. An addition of about 3% of the weight of the core as coating material is generally regarded as providing a continuous coat for this size range.

The controlled release portion of the dose can be provided by a controlled release core as described above, a controlled release core that is further modified by overcoating, or an immediate release core that is modified by overcoating.

A typical coating composition for making the controlled release component can contain an insoluble matrix polymer in an amount of about 15% to about 85% by weight of the coating composition, and a water soluble material in an amount of about 15% to about 85% by weight of the coating composition. Optionally, an enteric polymer in an amount of about 0.1% to about 100% by weight of the coating composition may be used or included. Suitable insoluble matrix polymers include ethyl cellulose, cellulose acetate butyrate, cellulose acetates, and polymethacrylates containing quaternary ammonium groups or other pharmaceutically acceptable polymers. Suitable water soluble materials include polymers such as polyethylene glycol, hydroxypropyl cellulose, hydroxypropyl methylcellulose, polyvinylpyrrolidone, polyvinyl alcohol; monomeric materials such as sugars (e.g., lactose, sucrose, fructose, mannitol and the like); salts (e.g., sodium chloride, potassium chloride and the like); organic acids (e.g., fumaric acid, succinic acid, lactic acid, tartaric acid and the like); and mixtures thereof. Suitable enteric polymers include hydroxypropyl methylcellulose acetate succinate (HPMCAS), hydroxypropyl methylcellulose phthalate (HPMCP), polyvinyl acetate phthalate, cellulose acetate phthalate, cellulose acetate trimellitate, shellac, zein, polymethacrylates containing carboxyl groups, and the like.

The coating composition can be plasticized according to the properties of the coating blend such as the glass transition temperature of the main component or mixture of components or the solvent used for applying the coating compositions. Suitable plasticizers can be added from about 0.1% to about 50% by weight of the coating composition. Such plasticizers can be selected from, for example, the group consisting of diethyl phthalate, citrate esters, polyethylene glycol, glycerol, acetylated glycerides, acetylated citrate esters, dibutyl sebacate, castor oil and the like.

The coating composition can include a filler. The filler can comprise about 0.1% to about 100% by weight based on the total weight of the coating composition. The filler can be an insoluble material such as silicon dioxide, titanium dioxide, talc, kaolin, alumina, starch, powdered cellulose, microcrystalline cellulose, polacrilin potassium, and the like.

The coating composition can be applied as a solution or latex in organic solvents or aqueous solvents of mixtures thereof. Where solutions are applied, the solvent is present in an amount of about 25% to about 99%, preferably about 85% to about 97%, by weight based on the total weight of dissolved solids. Suitable solvents are water, lower alcohol, lower chlorinated hydrocarbons, ketones or mixtures thereof. Where latexes are applied, the solvent is present in an amount of about 25% to about 97%, preferably about 60% to about 97%, by weight based on the quantity of polymeric material in the latex. The solvent can be predominantly water.

A suitable tablet formulation can include micronized eplerenone together with a swelling/gelling polymer such as L-hydroxypropyl cellulose admixed with a filler such as microcrystalline cellulose. The tablet carrier materials can be processed (i.e., spray dried) together, prior to compression. Matrix tablets of this type often exhibit a rapid initial release until the polymers swell and gel, which induces controlled release for the remainder of the drug.

The quantity of immediate release and duration of controlled release can be varied by altering the quantities of the carrier materials used. If the immediate release component is not large enough, a quantity of micronized eplerenone can be included in a rapidly dissolving outer coat of polymers such as polyethylene glycol or hydroxypropyl methylcellulose.

A typical matrix tablet can contain the swelling/gelling polymer in an amount of about 5% to about 70% by weight based on the total weight of the tablet, and a diluent in an amount of about 15% to about 90% by weight based on the total weight of the tablet. Additional diluents can be included in amounts from approximately 0.1% to about 65% by weight based on the total weight of the tablet. These can be soluble materials such as lactose, mannitol, sorbitol and the like, or insoluble materials such as tribasic calcium phosphate powdered cellulose or any of the various starches (corn, wheat, potato and the like).

Additionally, the tablets can contain a lubricant in an amount of about 0.1% to about 8% by weight based on the total weight of the tablet. Lubricants can be selected from metal stearates, stearic acid, hydrogenated oils, such as soya bean oil or castor oil, sodium stearyl furnate, polytetrafluoroethylene, talc and the like.

The tablets can be coated for aesthetic, handling or stability purposes, or to increase the quantity of the immediate release portion of eplerenone. In this latter case, micronized eplerenone is dissolved or suspended in the coating solution and sprayed onto the tablets until the desired quantity of eplerenone has been added. Suitable coating materials include polyethylene glycol, hydroxypropyl methylcellulose, hydroxypropyl cellulose, polyvinyl alcohol, polyvinylpyrrolidone, sugar, waxes, or mixtures of these.

The coating material can be added to any desired thickness but weight gains in the range about 1% to about 20% are typical, preferably about 2% to about 10%, and more preferably about 2% to about 5%. The coat can be plasticized. A plasticizer can be present in an amount of about 0.1% to about 50% by weight based on the total weight of the tablet of the coating material. Examples of plasticizers are diethyl phthalate, citrate esters, acetylated citrate esters, polyethylene glycol, glycerol, dibutyl sebacate, acetylated monoglycerides, castor oil and the like).

The coating composition can include an antitack agent such as talc, kaolin, titanium dioxide, silicon dioxide, alumina, starch, polacrilin potassium, microcrystalline cellulose or the like).

The coating materials can be applied to the eplerenone particles, processed eplerenone particles (i.e. cores, granules), finished tablets, or finished capsules.

The coating composition can also include a filler. The filler can comprise about 0.1% to about 100% by weight based on the total weight of the coating composition and can be an insoluble material such as silicon dioxide, titanium dioxide, talc, kaolin, alumina, starch, powdered cellulose, microcrystalline cellulose, polacrillin potassium. The coating composition can contain other ingredients such as dyes and waxes.

The coat can be applied as a solution or suspension from aqueous or organic solvents using solution concentrations and equipment familiar to these skilled in the art. The coating composition can be applied as a solution or latex in organic solvents or aqueous solvents or mixtures thereof. Where solutions are applied the solvent is present in an amount of about 25% to about 99%, preferably about 85% to about 97%, by weight based on the total weight of dissolved solids. Suitable solvents are water, lower alcohols such as ethanol and iso-propanol, lower chlorinated hydrocarbons such as chloroform and dichloromethane, ketones such as acetone and methyl ethyl ketone, or mixtures thereof. Where latexes are applied, the solvent is present in an amount of about 25% to about 97%, preferably about 60% to about 97%, by weight based on the quantity of polymeric material in the latex. The solvent can be predominantly water.

Alternatively, the controlled release component of a tablet can be provided in the form of controlled release pellets and the immediate release component can be included in the body of the tablet. Such a tablet disintegrates to release the immediate release drug and the controlled release pellets. Pellets can be present in an amount of about 1% to about 60%, preferably about 5% to about 50%, and more preferably about 5% to about 40%, by weight of the tablet. Suitable matrix materials for tablets of this type are microcrystalline cellulose, starches and the like.

The immediate release form of the micronized eplerenone can be presented in a fast dissolving dosage form. The immediate release form can be in the form of a solid or molecular dispersion of the active within a polymer matrix. The polymer matrix can be selected from biologically acceptable polymers such as a cellulose ether, for example ethyl cellulose, or cellulose ester, for example cellulose acetate butyrate and the like. The immediate release form can simply be particles of eplerenone deposited on a core containing eplerenone.

The composition of the invention, where it is in a tablet or like form, can include the two forms of the micronized eplerenone as separate components, for example, in a multilayer tablet, wherein one or more layers include the micronized eplerenone in a controlled release form. Alternatively, the composition of the invention can be in the form of a tablet wherein the immediate release form is present in the shell and the controlled release form constitutes the core. Alternatively, the two forms of the micronized eplerenone can be dispersed throughout the tablet.

The composition of the invention can be produced by providing a core containing the micronized eplerenone controlled release component coated with an enteric or delayed release coating. The core can be in the form of beads compressed to a tablet. The coated core can then be compressed into tablets along with a powder mixture containing additional eplerenone, or filled in combination with uncoated eplerenone into a capsule shell. As a result, the final composition provides an amount of eplerenone for immediate release following administration and an additional amount of eplerenone for controlled release.

The controlled release form of the micronized eplerenone is such as to provide sustained release of eplerenone. Preferably, the controlled or sustained release form provides a therapeutic effect over a period greater than about 12 hours, with a sustained therapeutic effect period of 12 to 24 hours being especially preferred.

The controlled release form can be in the form of coated beads or granules of micronized eplerenone. The coated micronized eplerenone can be combined with uncoated or lightly coated micronized eplerenone to provide a controlled release composition of the present invention. The term "lightly coated" as used in the description means a rapidly disintegrating coating for aesthetic, handling or stability purposes. These then can be filled into capsules or formed into tablets. Microencapsulation can also be used to produce the controlled release form of the micronized eplerenone.

The coating or matrix material can be any suitable material. The coating or matrix material can be a polymer or a wax. The wax can be selected from any suitable wax or wax-like material including natural oil and fat and hardened oils such as hardened rapeseed oil, hardened castor oil, hardened beef tallow, palm oils and the like; waxes such as carnauba wax, bees wax, paraffin wax, ceresine wax, shellac wax or a fatty acid.

Additional controlled release formulations can be prepared by appropriate modification of the formulations and methods disclosed in, for example, Jao et al., U.S. Pat. No. 5,190,765; Jao et al., U.S. Pat. No. 5,160,744; Wong et al., U.S. Pat. No. 5,082,668; Ayer et al., U.S. Pat. No. 4,847,093; EP 572942 A2 published Dec. 8, 1993; EP 284039 A2 published Sep. 28, 1988; EP 238189 A1 published Sep. 23, 1987; WO94/27582 published Dec. 8, 1994; WO92/13547 published Aug. 20, 1992; and WO92/00729 published Jan. 23, 1992, whose disclosures are incorporated by reference.

In one embodiment of the invention, the pharmaceutical composition is a controlled release oral dosage form, preferably a tablet or capsule, wherein the release of eplerenone is controlled by the utilization of a hydrophilic matrix that releases micronized eplerenone at a relatively constant rate over a period of several hours. This hydrophilic matrix can be prepared, for example, by incorporating hydroxypropyl methylcellulose into the formulation in combination with the other carrier materials. The amount of hydroxypropyl methylcellulose required depends upon the release rate desired. Illustrative compositions having various in vitro dissolution rates are described in the examples below.

In a typical formulation, the hydroxypropyl methylcellulose is combined with micronized eplerenone and other carrier materials, and then high shear wet granulated, fluid bed dried, blended and compressed into a tablet dosage form. Where hydroxypropyl methylcellulose is incorporated into the hydrophilic matrix to provide a controlled release dosage form, the hydroxypropyl methylcellulose used preferably is a high molecular weight (or high viscosity) hydroxypropyl methylcellulose. The term "high molecular weight (or high viscosity) hydroxypropyl methylcellulose" refers to those hydroxypropyl methylcelluloses having a 2% viscosity (that is, the viscosity of a 2% solution of hydroxypropyl methylcellulose in water at 20° C.) in the range of about 3,500 cps to about 5,600 cps.

When the tablet is exposed to aqueous media, such as in the gastrointestinal tract, the tablet surface wets and the polymer begins to partially hydrate forming an outer gel layer. This outer gel layer becomes fully hydrated and begins to erode into the aqueous fluids. Water continues to permeate toward the core of the tablet permitting another gel layer to form beneath the dissolving outer gel layer. These successive concentric gel layers sustain uniform release of eplerenone by diffusion from the gel layer and exposure through tablet erosion.

In general, increasing the concentration of the polymer in the matrix increases the viscosity of the gel that forms on the tablet surface and causes a decrease in diffusion and release of eplerenone. Typical two hour controlled release formulations (that is, formulations releasing about 50% of the eplerenone in vitro during the two hour period after ingestion) comprise about 2% to about 20%, preferably about 3% to about 17%, and more preferably about 4% to about 14%, high molecular weight hydroxypropyl methylcellulose by weight of the composition. Typical four hour controlled release formulations (that is, formulations releasing about 50% of the eplerenone in vitro during the four hour period after ingestion) comprise about 5% to about 45%, preferably about 7% to about 35%, and more preferably about 8% to about 28%, high molecular weight hydroxypropyl methylcellulose by weight of the composition. Typical six hour controlled release formulations (that is, formulations releasing about 50% of the eplerenone in vitro during the six hour period after ingestion) comprise about 10% to about 45%, preferably about 12% to about 35%, and more preferably about 14% to about 35%, high molecular weight hydroxypropyl methylcellulose by weight of the composition.

Changes in the tablet size and shape can affect the surface to volume ratio of the tablet and therefore the drug release kinetics from the hydrophilic matrix of the tablet. In general, it has been discovered that release of micronized eplerenone from the pharmaceutical compositions of the present invention is enhanced when tablet size is decreased and/or tablet shape is changed from round to caplet. It also has been discovered that particle size of the polymer influences the rate at which micronized eplerenone is released from the tablet. It is believed that as the polymer particle size decreases, hydration of the polymer occurs more rapidly on the tablet surface resulting in slower drug release. Further, because tablet coating can alter eplerenone release kinetics, the effect of the coating on drug release should be considered for coated tablets. Testing of the controlled release tablets of the present invention indicated that release of eplerenone from the tablet is substantially independent of tablet compression force for compression forces between about 10 kN to about 40 kN.

In another embodiment, the pharmaceutical compositions comprise:
  about 24 to about 35 weight percent of micronized eplerenone;
  about 25 to about 45 weight percent of lactose monohydrate;
  about 10 to about 25 weight percent of microcrystalline cellulose; and
  about 5 to about 50 weight percent of hydroxypropyl methylcellulose.

These pharmaceutical compositions optionally can additionally comprise about 0.1 to about 2 weight percent of talc; and/or about 0.25 to about 0.75 weight percent of magnesium stearate.

More preferably, the pharmaceutical compositions of this embodiment comprise about 25 to about 35 weight percent of micronized eplerenone; about 35 to about 45 weight percent of lactose; about 14.5 to about 24.5 weight percent of microcrystalline cellulose; about 1 to about 11 weight percent of high molecular weight hydroxypropyl methylcellulose; and about 0.5 to about 8 weight percent of low molecular weight hydroxypropyl methylcellulose. These pharmaceutical compositions optionally can additionally comprise about 0.1 to about 6 weight percent of talc; and about 0.1 to about 5.5 weight percent of magnesium stearate.

In one embodiment, the pharmaceutical compositions are controlled release compositions comprising:
  about 20 to about 40 weight percent of micronized eplerenone;
  about 30 to about 50 weight percent of lactose;
  about 9.5 to about 29.5 weight percent of microcrystalline cellulose;

about 1 to about 16 weight percent of high molecular weight hydroxypropyl methylcellulose; and about 0.5 to about 13 weight percent of low molecular weight hydroxypropyl methylcellulose.

These pharmaceutical compositions optionally can additionally comprise about 0.1 to about 10 weight percent of talc; and about 0.1 to about 10 weight percent of magnesium stearate. Preferably, the low molecular weight hydroxypropyl methylcellulose has a viscosity of from about 2 cps to about 8 cps, more preferably about 2 cps to about 6 cps, as discussed before. Preferably, the high molecular weight hydroxypropyl methylcellulose has a 2% viscosity value of from about 3500 cps to about 5,600 cps, as also discussed before. The compositions preferably are in the form of unit dosage tablets.

More preferably, the pharmaceutical compositions of this embodiment comprise about 25 to about 35 weight percent of micronized eplerenone; about 35 to about 45 weight percent of lactose; about 14.5 to about 24.5 weight percent of microcrystalline cellulose; about 1 to about 11 weight percent of high molecular weight hydroxypropyl methylcellulose; and about 0.5 to about 8 weight percent of low molecular weight hydroxypropyl methylcellulose. These pharmaceutical compositions optionally can additionally comprise about 0.1 to about 6 weight percent of talc; and about 0.1 to about 5.5 weight percent of magnesium stearate.

Still more preferably, the pharmaceutical compositions of this embodiment comprise about 28 to about 32 weight percent of micronized eplerenone; about 38 to about 42 weight percent of lactose; about 17.5 to about 21.5 weight percent of microcrystalline cellulose; about 4 to about 8 weight percent of high molecular weight hydroxypropyl methylcellulose; and about 2 to about 5 weight percent of low molecular weight hydroxypropyl methylcellulose. These pharmaceutical compositions optionally can additionally comprise about 0.1 to about 3 weight percent of talc; and about 0.1 to about 2.5 weight percent of magnesium stearate.

In another embodiment, the pharmaceutical compositions are controlled release compositions comprising:

about 20 to about 40 weight percent of micronized eplerenone;

about 15 to about 47 weight percent of lactose;

about 3.5 to about 28.5 weight percent of microcrystalline cellulose;

about 1 to about 45 weight percent of high molecular weight hydroxypropyl methylcellulose; and about 0.5 to about 13 weight percent of low molecular weight hydroxypropyl methylcellulose.

These pharmaceutical compositions optionally may additionally comprise about 0.1 to about 10 weight percent of talc; and about 0.1 to about 10 weight percent of magnesium stearate. Preferably, the low molecular weight hydroxypropyl methylcellulose has a viscosity of from about 2 cps to about 8 cps, more preferably about 2 cps to about 6 cps, whereas the high molecular weight hydroxypropyl methylcellulose has a 2% viscosity value of from about 3500 cps to about 5,600 cps, as discussed before. The compositions preferably are in the form of unit dosage tablets.

More preferably, the pharmaceutical compositions of this embodiment comprise about 25 to about 35 weight percent of micronized eplerenone; about 22 to about 42 weight percent of lactose; about 8.5 to about 23.5 weight percent of microcrystalline cellulose; about 5 to about 35 weight percent of high molecular weight hydroxypropyl methylcellulose; and about 0.5 to about 8 weight percent of low molecular weight hydroxypropyl methylcellulose. These pharmaceutical compositions optionally can additionally comprise about 0.1 to about 6 weight percent of talc; and about 0.1 to about 5.5 weight percent of magnesium stearate.

Still more preferably, the pharmaceutical compositions of this embodiment comprise about 28 to about 32 weight percent of micronized eplerenone; about 25 to about 39 weight percent of lactose; about 11.5 to about 20.5 weight percent of microcrystalline cellulose; about 10 to about 35 weight percent of high molecular weight hydroxypropyl methylcellulose; and about 2 to about 5 weight percent of low molecular weight hydroxypropyl methylcellulose. These pharmaceutical compositions optionally can additionally comprise about 0.1 to about 3 weight percent of talc; and about 0.1 to about 2.5 weight percent of magnesium stearate.

In another embodiment, the pharmaceutical compositions are controlled release compositions comprising:

about 20 to about 40 weight percent of micronized eplerenone;

about 20.5 to about 40.5 weight percent of lactose;

about 5 to about 25 weight percent of microcrystalline cellulose;

about 10 to about 30 weight percent of high molecular weight hydroxypropyl methylcellulose; and about 0.5 to about 13 weight percent of low molecular weight hydroxypropyl methylcellulose.

These pharmaceutical compositions optionally may additionally comprise about 0.1 to about 10 weight percent of talc; and about 0.1 to about 10 weight percent of magnesium stearate. Preferably, the low molecular weight hydroxypropyl methylcellulose has a viscosity of from about 2 cps to about 8 cps, more preferably about 2 cps to about 6 cps, whereas the high molecular weight hydroxypropyl methylcellulose has a 2% viscosity value of from about 3500 cps to about 5,600 cps, as before. The compositions preferably are in the form of unit dosage tablets.

Still more preferably, the pharmaceutical compositions of this embodiment comprise about 28 to about 32 weight percent of micronized eplerenone; about 28.5 to about 32.5 weight percent of lactose; about 13 to about 17 weight percent of microcrystalline cellulose; about 18 to about 22 weight percent of high molecular weight hydroxypropyl methylcellulose; and about 2 to about 5 weight percent of low molecular weight hydroxypropyl methylcellulose. These pharmaceutical compositions optionally can additionally comprise about 0.1 to about 3 weight percent of talc; and about 0.1 to about 2.5 weight percent of magnesium stearate.

In another embodiment, the pharmaceutical compositions of this embodiment comprise:

about 25 mg to about 150 mg of micronized eplerenone;

about 12.5 mg to about 190 mg of lactose;

about 2 mg to about 100 mg of microcrystalline cellulose;

about 10 mg to about 80 mg of high molecular weight hydroxypropyl methylcellulose; and about 1 mg to about 25 mg of low molecular weight hydroxypropyl methylcellulose.

These pharmaceutical compositions optionally can additionally comprise about 0.5 mg to about 15 mg of talc; and about 0.1 mg to about 10 mg of magnesium stearate. Preferably, the low molecular weight hydroxypropyl methylcellulose has a viscosity of from about 2 cps to about 8 cps, more preferably about 2 cps to about 6 cps, whereas the high molecular weight hydroxypropyl methylcellulose has a 2% viscosity value of from about 3500 cps to about 5,600 cps, as before.

In another embodiment, the pharmaceutical compositions of this embodiment comprise:

about 95 mg to about 105 mg of micronized eplerenone;
about 128 mg to about 139 mg of lactose;
about 60 mg to about 70 mg of microcrystalline cellulose;
about 10 mg to about 25 mg of high molecular weight hydroxypropyl methylcellulose; and
about 5 mg to about 15 mg of low molecular weight hydroxypropyl methylcellulose.

These pharmaceutical compositions optionally can additionally comprise about 0.5 mg to about 8 mg of talc; and about 0.1 mg to about 7 mg of magnesium stearate. The compositions preferably are in the form of unit dosage tablets.

More preferably, the pharmaceutical compositions of this embodiment comprise about 98 mg to about 102 mg of micronized eplerenone; about 131 mg to about 136 mg of lactose; about 63 mg to about 67 mg of microcrystalline cellulose; about 18 mg to about 22 mg of high molecular weight hydroxypropyl methylcellulose; and about 8 mg to 12 mg of low molecular weight hydroxypropyl methylcellulose. These pharmaceutical compositions optionally can additionally comprise about 2 mg to about 5 mg of talc; and about 0.5 to about 3 weight percent of magnesium stearate.

In another embodiment, the pharmaceutical compositions of this embodiment comprise:
about 45 mg to about 55 mg of micronized eplerenone;
about 35 mg to about 55 mg of lactose;
about 17.5 mg to about 27.5 mg of microcrystalline cellulose;
about 37 mg to about 47 mg of high molecular weight hydroxypropyl methylcellulose; and
about 1 mg to about 10 mg of low molecular weight hydroxypropyl methylcellulose.

These pharmaceutical compositions optionally can additionally comprise about 0.5 mg to about 7 mg of talc; and about 0.1 mg to about 6 mg of magnesium stearate. The compositions preferably are in the form of unit dosage tablets.

More preferably, the pharmaceutical compositions of this embodiment comprise about 48 mg to about 52 mg of micronized eplerenone; about 43 mg to about 47 mg of lactose; about 20.5 mg to about 24.5 mg of microcrystalline cellulose; about 40 mg to about 44 mg of high molecular weight hydroxypropyl methylcellulose; and about 3 mg to 7 mg of low molecular weight hydroxypropyl methylcellulose. These pharmaceutical compositions optionally can additionally comprise about 0.5 mg to about 3 mg of talc; and about 0.1 to about 3 weight percent of magnesium stearate.

In another embodiment, the pharmaceutical compositions of this embodiment comprise:
about 95 mg to about 105 mg of micronized eplerenone;
about 110 mg to about 195 mg of lactose;
about 50 mg to about 70 mg of microcrystalline cellulose;
about 30 mg to about 50 mg of high molecular weight hydroxypropyl methylcellulose; and
about 5 mg to about 15 mg of low molecular weight hydroxypropyl methylcellulose.

These pharmaceutical compositions optionally can additionally comprise about 0.5 mg to about 8 mg of talc; and about 0.1 mg to about 7 mg of magnesium stearate. The compositions preferably are in the form of unit dosage tablets.

More preferably, the pharmaceutical compositions of this embodiment comprise about 98 mg to about 102 mg of micronized eplerenone; about 118 mg to about 122 mg of lactose; about 58 mg to about 62 mg of microcrystalline cellulose; about 38 mg to about 42 mg of high molecular weight hydroxypropyl methylcellulose; and about 8 mg to 12 mg of low molecular weight hydroxypropyl methylcellulose. These pharmaceutical compositions optionally can additionally comprise about 2 mg to about 5 mg of talc; and about 0.5 to about 3 weight percent of magnesium stearate.

In another embodiment, the pharmaceutical compositions of this embodiment comprise:
about 145 mg to about 155 mg of micronized eplerenone;
about 175 mg to about 195 mg of lactose;
about 87.5 mg to about 97.5 mg of microcrystalline cellulose;
about 45 mg to about 55 mg of high molecular weight hydroxypropyl methylcellulose; and
about 10 mg to about 20 mg of low molecular weight hydroxypropyl methylcellulose.

These pharmaceutical compositions optionally can additionally comprise about 0.5 mg to about 10 mg of talc; and about 0.1 mg to about 8 mg of magnesium stearate. The compositions preferably are in the form of unit dosage tablets.

More preferably, the pharmaceutical compositions of this embodiment comprise about 148 mg to about 152 mg of micronized eplerenone; about 183 mg to about 187 mg of lactose; about 90.5 mg to about 94.5 mg of microcrystalline cellulose; about 48 mg to about 52 mg of high molecular weight hydroxypropyl methylcellulose; and about 13 mg to 17 mg of low molecular weight hydroxypropyl methylcellulose. These pharmaceutical compositions optionally may additionally comprise about 3 mg to about 7 mg of talc; and about 0.5 to about 4.5 weight percent of magnesium stearate.

In another embodiment, the pharmaceutical compositions of this embodiment comprise:
about 95 mg to about 105 mg of micronized eplerenone;
about 96.5 mg to about 106.5 mg of lactose;
about 45 mg to about 55 mg of microcrystalline cellulose;
about 61.5 mg to about 71.5 mg of high molecular weight hydroxypropyl methylcellulose; and
about 5 mg to about 15 mg of low molecular weight hydroxypropyl methylcellulose.

These pharmaceutical compositions optionally can additionally comprise about 0.5 mg to about 8 mg of talc; and about 0.1 mg to about 7 mg of magnesium stearate. The compositions preferably are in the form of unit dosage tablets.

More preferably, the pharmaceutical compositions of this embodiment comprise about 98 mg to about 102 mg of micronized eplerenone; about 99.5 mg to about 103.5 mg of lactose; about 48 mg to about 52 mg of microcrystalline cellulose; about 64.5 mg to about 68.5 mg of high molecular weight hydroxypropyl methylcellulose; and about 8 mg to 12 mg of low molecular weight hydroxypropyl methylcellulose. These pharmaceutical compositions optionally can additionally comprise about 2 mg to about 5 mg of talc; and about 0.5 to about 3 weight percent of magnesium stearate.

In another embodiment, the pharmaceutical compositions of this embodiment comprise lactose, microcrystalline cellulose, hydroxypropyl methylcellulose, talc, and magnesium stearate.

In still another embodiment, the pharmaceutical compositions release in vitro at least about 50% of the eplerenone contained in the composition in at least about 1.5 hours, preferably in at least about 1.75 hours, and more preferably in about 2 hours.

In still another embodiment, the pharmaceutical compositions release in vitro at least about 50% of the eplerenone contained in the composition at least about 3.5 hours, preferably at least about 3.75 hours, and more preferably about 4 hours.

In still another embodiment, the pharmaceutical compositions release in vitro at least about 50% of the eplerenone contained in the composition at least about 5.5 hours, preferably at least about 5.75 hours, and more preferably about 6 hours.

In still another embodiment, the pharmaceutical compositions comprise micronized eplerenone and one or more carrier materials, are in oral unit dosage form suitable for once-a-day or twice-a-day oral administration, and release in vitro about 50% or more of the eplerenone contained in the composition at least about 1.5 hours after ingestion of the composition. Still more preferably, these pharmaceutical compositions comprise eplerenone and one or more carrier materials selected from the group consisting of lactose monohydrate, microcrystalline cellulose, hydroxypropyl methylcellulose, talc, and magnesium stearate. It is particularly preferred that the various components of the controlled release matrix be present in the amounts or the weight fractions set forth above.

Other Active Ingredients

The pharmaceutical compositions of the present invention are also useful for the administration of other 9,11-epoxy-20-spiroxane compounds, particularly those 9,11-epoxy-20-spiroxane compounds that are aldosterone antagonists. These pharmaceutical compositions can be prepared as set forth in this application by replacing eplerenone with a comparable weight fraction of the desired 9,11-epoxy-20-spiroxane. The 9,11-epoxy-20-spiroxane compounds used in the preparation of such pharmaceutical compositions can be prepared, for example, as set forth in Grob et al., U.S. Pat. No. 4,559,332. Such 9,11-epoxy-spiroxanes include, but are not limited to, the following compounds:

9α,11α-epoxy-7α-methoxycarbonyl-15β,16β-methylene-20-spirox-4-ene-3,21-dione;

9α,11α-epoxy-7α-isopropoxycarbonyl-20-spirox-4-ene-3,21-dione;

9α,11α-epoxy-7α-ethoxycarbonyl-20-spirox-4-ene-3,21-dione;

9α,11α-epoxy-6β,7β-methylene-20-spirox-4-ene-3,21-dione;

9α,11α-epoxy-6β,7β; 15β,16β-bis-methylene-20-spirox-4-ene-3,21-dione;

9α,11α-epoxy-17β-hydroxy-6β,7β-methylene-3-oxo-17α-pregn-4-ene-21-carboxylic acid;

9α,11α-epoxy-17β-hydroxy-6β,7β-methylene-3-oxo-17α-pregn-4-ene-21-carboxylic acid methyl ester;

9α,11α-epoxy-17β-hydroxy-6β,7β; 15β,16β-bis-methylene-3-oxo-17α-pregn-4-ene-21-carboxylic acid methyl ester;

9α,11α-epoxy-6β,7β-methylene-20-spiroxa-1,4-diene-3,21-dione;

9α,11α-epoxy-17β-hydroxy-7α-methoxycarbonyl-3-oxo-17α-pregn-4-ene-21-carboxylic acid;

9α,11α-epoxy-17β-hydroxy-3-oxo-17β-pregn-4-ene-7α,21-dicarboxylic acid dimethyl ester;

9α,11α-epoxy-17β-hydroxy-7α-isopropoxycarbonyl-3-oxo-17α-pregn-4-ene-21-carboxylic acid;

9α,11α-epoxy-17β-hydroxy-7α-ethoxycarbonyl-3-oxo-17α-pregn-4-ene-21-carboxylic acid;

9α,11α-epoxy-6α,7α-methylene-20-spirox-4-ene-3,21-dione;

9α,11α-epoxy-17β-hydroxy-3-oxo-17α-pregn-4-ene-7α,21-dicarboxylic acid dimethyl ester; and 9α,11α-epoxy-17β-hydroxy-15β,16β-methylene-3-oxo-17α-pregn-4-ene-7α,21-dicarboxylic acid dimethyl ester; and the pharmaceutically acceptable salts thereof.

Methods of Treatment

The present invention also is directed to therapeutic methods of treating a condition or disorder where treatment with an aldosterone receptor blocker is indicated, the methods comprising the oral administration of one or more of the pharmaceutical compositions previously described above to a patient in need thereof. The dosage regimen to prevent, give relief from, or ameliorate the condition or disorder preferably corresponds to once-a-day or twice-a-day oral dosages, and more preferably to the 25 mg, 50 mg, 100 mg or 150 mg eplerenone oral unit dosages discussed above, but can be modified in accordance with a variety of factors. These factors include the type, age, weight, sex, diet, and medical condition of the patient and the severity of the disease. Thus, the dosage regimen actually employed can vary widely and therefore deviate from the preferred dosage regimen set forth above.

Initial treatment of a patient suffering from a condition or disorder where treatment with an aldosterone receptor blocker is indicated can begin with the dosages indicated above. Treatment is generally continued as necessary over a period of several weeks to several months or years until the condition or disorder has been controlled or eliminated. Patients undergoing treatment with the compositions disclosed herein can be routinely monitored by any of the methods well known in the art to determine the effectiveness of therapy. Continuous analysis of such data permits modification of the treatment regimen during therapy so that optimal effective amounts of compounds of the present invention are administered at any point in time, and so that the duration of treatment can be determined as well. In this way, the treatment regimen/dosing schedule can be rationally modified over the course of therapy so that the lowest amount of eplerenone exhibiting satisfactory effectiveness is administered, and so that administration is continued only so long as is necessary to successfully treat the condition or disorder.

The present invention further encompasses the use of micronized eplerenone and a cellulosic carrier material in the manufacture of a medicament for the treatment or prophylaxis of aldosterone-mediated conditions or disorders.

Method for Preparation of Formulation

The present invention also is directed to methods for the preparation of pharmaceutical compositions comprising micronized eplerenone. Where tablets or capsules are desired, methods such as wet granulation, dry granulation or direct compression or encapsulation methods can be employed.

Wet granulation is a preferred method of preparing tablets from the pharmaceutical compositions of the present invention. In the wet granulation process, the micronized eplerenone (and, if desired, any of the carrier materials) is initially milled or micronized to the desired particle size using a conventional mill or grinder. Such milling or grinding techniques are well known in the art, as are methods for ascertaining the resulting particle size and distribution.

As previously discussed, reduction of the $D_{90}$ eplerenone particle size (that is, the size of at least 90% of the eplerenone particles) in the composition is less than about 400 microns and more than 25 microns, preferably less than about 200 microns, more preferably less than about 150 microns, still more preferably less than about 100 microns, and yet more preferably less than 90 microns. A particularly preferred $D_{90}$ particle size is about 30 to about 110 microns, and more particularly still about 30 to about 50 microns. In other preferred embodiments, a particularly preferred $D_{90}$ particle size is about 50 to about 150 microns, and more preferably about 75 to about 125 microns. Micronized eplerenone so sized can materially increase the bioavailability of the eplerenone.

Micronized eplerenone used illustratively herein typically had a $D_{90}$ value of about 30 to about 110 microns. Exemplary particle distributions are provided hereinafter for some of the specific examples.

Particle size distributions are determined using the following procedure.

Equipment and Reagents
1. Sympatec™ HELOS System Laser Light Diffraction Particle Size Apparatus in a dry powder mode, model H0790 equipped with VIBRI™ feeder and RODOS™ dispersing system.
2. 200–500 mm focal length lens.
3. Corn Starch, NF (reference standard illustratively; $D_{90}$=31.54, $D_{75}$=20.50, $D_{50}$=15.15 and $D_{10}$=7.44 microns).
4. Control Sample of micronized eplerenone (illustratively; $D_{90}$=22.01, $D_{75}$=13.35, $D_{50}$=7.57 and $D_{10}$10.8 microns).

Distribution Points 5,10,50,75,90 and 95%

For Data Collection

Analysis Procedure:
1. Verify or install the lens.
2. Using corn starch, NF (reference standard), perform an instrument function verification, according to established equipment procedure.
3. Run a control sample of micronized eplerenone in singlet and ensure that the particle size distribution is similar to previous runs.
4. Weigh approximately 500 mg of sample and determine the particle size distribution in triplicate.
5. Calculate the mean, standard deviation, and percent relative standard deviation at each distribution point.
6. Report the mean particle size, standard deviation, and n at the 5, 10, 50, 75, 90 and $95^{th}$ percentile to an integer.

The milled or micronized eplerenone is then blended, for example in a high shear mixer granulator, planetary mixer, a twin-shell blender or sigma mixer, with one or more of the carrier materials. Typically, the drug is blended with the diluent(s), disintegrant(s), binding agent(s) and, optionally, wetting agent(s) in this step although it is possible to add all or a portion of one or more of the carrier materials in a later step.

For example, where microcrystalline cellulose is employed as a diluent, it has been discovered that addition of a portion of the microcrystalline cellulose during this blending step and the addition of the remaining portion after the drying step discussed below increases the hardness and/or decreases the friability of the tablets produced. In this situation, preferably about 40% to about 50% of the microcrystalline cellulose is added intragranularly and about 50% to about 60% of the microcrystalline cellulose is added extragranularly. In addition, this step of the process preferably comprises the blending of eplerenone, lactose, microcrystalline cellulose, hydroxypropyl methylcellulose and, optionally, sodium lauryl sulfate. It has been discovered that blending times as short as three minutes can provide a dry powder mixture having a sufficiently uniform distribution of eplerenone.

Water is then added to the dry powder mixture and the mixture is blended for an additional period of time. The water can be added to the mixture at once, gradually over a period of time, or in several portions over a period of time. The water preferably is added gradually over a period of time, preferably at least about three to about five minutes. An additional period of mixing, generally at least about one to about three minutes, after the water addition is complete, appears to ensure the uniform distribution of the water in the mixture and results in a suitable wet granulated mixture.

It is generally preferred that the wet granulated mixture comprise about 25% to about 45% water by weight. Although a higher or lower water content can be acceptable for certain formulations, a lower water content generally reduces the effectiveness of the step in producing granules having the desired compressibility and flowability properties, whereas a higher water content generally causes an increase in granule size.

The wet granulated mixture is then dried, for example, in an oven or a fluidized bed dryer, preferably a fluidized bed drier. If desired, the wet granulated mixture can be wet milled, extruded or spheronized prior to drying, although wet milling is preferred. For the drying process, conditions such as inlet air temperature and drying time are adjusted to achieve the desired moisture content for the dried mixture. Increasing moisture content from about 2% to about 4% was observed to decrease initial tablet hardness.

To the extent necessary, the dry granules are then reduced in size in preparation for compression. Conventional particle size reduction equipment such as oscillators or fitz mills can be employed.

The dry granules are then placed in a suitable blender such as a twin-shell blender and the lubricant, anti-adherent agent and any additional carrier materials are added. Although blending times depend in part upon the process equipment used, it has been discovered that blending times of at least about 5 to 25 minutes are generally preferred. In a preferred embodiment of this step of the invention, talc and the remaining portion of microcrystalline cellulose are added to the granules and the mixture blended for an additional period of time, preferably a period of time sufficient to achieve a blend uniformity relative standard deviation value of about 6% or less.

Magnesium stearate is then added to the mixture and the mixture is blended for an additional period of time. As noted above, where the diluents include microcrystalline cellulose, the addition of a portion of the microcrystalline cellulose during this step has been found to materially increase tablet hardness. In addition, increasing the amount of magnesium stearate was observed to decrease tablet hardness and increase friability and disintegration time.

This blended mixture is then compressed into tablets (or encapsulated if capsules are to be prepared) to the desired weight and hardness using appropriate size tooling. Conventional compression and encapsulation techniques known to those of ordinary skill in the art can be employed. Where coated tablets are desired, conventional coating techniques known to those of ordinary skill in the art can be employed.

The following examples illustrate aspects of the present invention but should not be construed as limitations. The experimental procedures used to generate the data shown are discussed in more detail below. The symbols and conventions used in these examples are consistent with those used in the contemporary pharmaceutical literature. Unless otherwise stated, (i) all percentages recited in these examples are weight percents based on total composition weight, (ii) total composition weight for capsules is the total capsule fill weight and does not include the weight of the actual capsule employed, and (iii) coated tablets are coated with a conventional coating material such as Opadry® White YS-1-18027A (or another color) and the weight fraction of the coating is about 3% of the total weight of the coated tablet.

EXAMPLE 1

25 Mg Dose Immediate Release Tablet

A 25 mg dose immediate release tablet (tablet diameter of 7/32") was prepared having the following composition:

TABLE 1

| INGREDIENT | WEIGHT % OF TABLET | Amount (mg) |
|---|---|---|
| Eplerenone | 29.41 | 25.00 |
| Lactose Monohydrate (#310, NF) | 42.00 | 35.70 |
| Microcrystalline Cellulose (NF, Avicel® PH101) | 18.09 (7.50% intragranular plus 10.59% extragranular) | 15.38 |
| Croscarmellose Sodium (NF, Ac-Di-Sol ™) | 5.00 | 4.25 |
| Hydroxypropyl Methylcellulose (#2910, USP, Pharmacoat ™ 603) | 3.00 | 2.55 |
| Sodium Lauryl Sulfate (NF) | 1.00 | 0.85 |
| Talc (USP) | 1.00 | 0.85 |
| Magnesium Stearate (NF) | 0.50 | 0.42 |
| Total | 100 | 85 |
| Opadry ® White YS-1-18027A | 3.00 | 2.55 |
| (Alternatively: Opadry ® Yellow YS-1-12524-A) | (4.50) | (3.825) |

The lactose monohydrate used in each of the examples of the application is commercially available from Formost Farms, Baraboo, Wisconsin. The Avicel® brand of microcrystalline cellulose and the Ac-Di-Sol™ brand of croscarmellose sodium were used in each of the examples of the application. Both compounds are commercially available from FMC Corporation, Chicago, Ill. The Pharmacoat™ 603 brand of hydroxypropyl methylcellulose was used in each of the examples of the application. This compound is commercially available from Shin-Etsu Chemical Co. Ltd. The sodium lauryl sulfate used in each of the examples of the application is commercially available from Henkel Corporation, Cincinnati, Ohio. The talc used in each of the examples of the application is commercially available from Cyprus Foote Mineral Co., Kings Mountain, N.C., or Luzenac America, Inc., Englewood, Colo. The magnesium stearate used in each of the examples of the application is commercially available from Mallinckrodt Inc., St. Louis, Mo. The Opadry® White YS-1-18027A (and other coatings) used to prepare the coated tablets disclosed in the examples of this application is a ready to coat coating formulation commercially available from Colorcon, West Point, Pa.

EXAMPLE 2

50 Mg Dose Immediate Release Tablet

A 50 mg dose immediate release tablet (tablet diameter of 9/32") was prepared having the following composition:

TABLE 2

| INGREDIENT | WEIGHT % OF TABLET | Amount (mg) |
|---|---|---|
| Eplerenone | 29.41 | 50.00 |
| Lactose Monohydrate (#310, NF) | 42.00 | 71.40 |
| Microcrystalline Cellulose (NF, Avicel ® PH101) | 18.09 (7.50% intragranular plus 10.59% extragranular) | 30.75 |
| Croscarmellose Sodium (NF, Ac-Di-Sol ™) | 5.00 | 8.50 |
| Hydroxypropyl Methylcellulose (#2910, USP, Pharmacoat ™ 603) | 3.00 | 5.10 |
| Sodium Lauryl Sulfate (NF) | 1.00 | 1.70 |
| Talc (USP) | 1.00 | 1.70 |
| Magnesium Stearate (NF) | 0.50 | 0.85 |
| Total | 100 | 170 |
| Opadry ® White YS-1-18027A | 3.00 | 5.10 |
| (Alternatively: Opadry ® Pink YS-1-14762-A) | (3.00) | (5.10) |

EXAMPLE 3

100 Mg Dose Immediate Release Tablet

A 100 mg dose immediate release tablet formulation (tablet diameter of 12/32") was prepared having the following composition:

TABLE 3

| INGREDIENT | WEIGHT % OF TABLET | Amount (mg) |
|---|---|---|
| Eplerenone | 29.41 | 100.00 |
| Lactose Monohydrate (#310, NF) | 42.00 | 142.80 |
| Microcrystalline Cellulose (NF, Avicel ® PH101) | 18.09 (7.50% intragranular plus 10.59% extragranular) | 61.50 |
| Croscarmellose Sodium (NF, Ac-Di-Sol ™) | 5.00 | 17.00 |
| Hydroxypropyl Methylcellulose (#2910, USP, Pharmacoat ™ 603) | 3.00 | 10.20 |
| Sodium Lauryl Sulfate (NF) | 1.00 | 3.40 |
| Talc (USP) | 1.00 | 3.40 |
| Magnesium Stearate (NF) | 0.50 | 1.70 |
| Total | 100 | 340 |
| Opadry ® White YS-1-18027A | 3.00 | 10.20 |
| (Alternatively: Opadry ® Red YS-1-15585-A) | (3.00) | (10.20) |

EXAMPLE 4

10 mg Dose Immediate Release Capsule

A 10 mg dose immediate release capsule formulation was prepared having the following composition:

TABLE 4

| INGREDIENT | AMOUNT (mg) | REPRESENTATIVE BATCH AMOUNT (kg) |
|---|---|---|
| Eplerenone | 10.0 | 1.00 |
| Lactose, Hydrous NF | 306.8 | 30.68 |
| Microcrystalline Cellulose, NF | 60.0 | 6.00 |
| Talc, USP | 10.0 | 1.00 |
| Croscarmellose Sodium, NF | 8.0 | 0.80 |
| Sodium Lauryl Sulfate, NF | 2.0 | 0.20 |
| Colloidal Silicon Dioxide, NF | 2.0 | 0.20 |
| Magnesium Stearate, NF | 1.2 | 0.12 |
| Total Capsule Fill Weight | 400.0 | 40.00 |
| Hard Gelatin Capsule, Size #0, White Opaque | 1 Capsule | 100,000 Capsules |

EXAMPLE 5

25 mg Dose Immediate Release Capsule

A 25 mg dose immediate release capsule formulation was prepared having the following composition:

TABLE 5

| INGREDIENT | AMOUNT (mg) | REPRESENTATIVE BATCH AMOUNT (kg) |
|---|---|---|
| Eplerenone | 25.0 | 2.50 |
| Lactose, Hydrous NF | 294.1 | 29.41 |
| Microcrystalline Cellulose, NF | 57.7 | 5.77 |
| Talc, USP | 10.0 | 1.00 |
| Croscarmellose Sodium, NF | 8.0 | 0.80 |
| Sodium Lauryl Sulfate, NF | 2.0 | 0.20 |
| Colloidal Silicon Dioxide, NF | 2.0 | 0.20 |
| Magnesium Stearate, NF | 1.2 | 0.12 |
| Total Capsule Fill Weight | 400.0 | 40.00 |
| Hard Gelatin Capsule, Size #0, White Opaque | 1 Capsule | 100,000 Capsules |

EXAMPLE 6

50 mg Dose Immediate Release Capsule

A 50 mg dose immediate release capsule formulation was prepared having the following composition:

TABLE 6

| INGREDIENT | AMOUNT (mg) | REPRESENTATIVE BATCH AMOUNT (kg) |
|---|---|---|
| Eplerenone | 50.0 | 5.00 |
| Lactose, Hydrous NF | 273.2 | 27.32 |

TABLE 6-continued

| INGREDIENT | AMOUNT (mg) | REPRESENTATIVE BATCH AMOUNT (kg) |
|---|---|---|
| Microcrystalline Cellulose, NF | 53.6 | 5.36 |
| Talc, USP | 10.0 | 1.00 |
| Croscarmellose Sodium, NF | 8.0 | 0.80 |
| Sodium Lauryl Sulfate, NF | 2.0 | 0.20 |
| Colloidal Silicon Dioxide, NF | 2.0 | 0.20 |
| Magnesium Stearate, NF | 1.2 | 0.12 |
| Total Capsule Fill Weight | 400.0 | 40.00 |
| Hard Gelatin Capsule, Size #0, White Opaque | 1 Capsule | 100,000 Capsules |

EXAMPLE 7

100 mg Dose Immediate Release Capsule

A 100 mg dose immediate release capsule formulation was prepared having the following composition:

TABLE 7

| INGREDIENT | AMOUNT (mg) | REPRESENTATIVE BATCH AMOUNT (kg) |
|---|---|---|
| Eplerenone | 100.0 | 10.00 |
| Lactose, Hydrous NF | 231.4 | 23.14 |
| Microcrystalline Cellulose, NF | 45.4 | 4.54 |
| Talc, USP | 10.0 | 1.00 |
| Croscarmellose Sodium, NF | 8.0 | 0.80 |
| Sodium Lauryl Sulfate, NF | 2.0 | 0.20 |
| Colloidal Silicon Dioxide, NF | 2.0 | 0.20 |
| Magnesium Stearate, NF | 1.2 | 0.12 |
| Total Capsule Fill Weight | 400.0 | 40.00 |
| Hard Gelatin Capsule, Size #0, White Opaque | 1 Capsule | 100,000 Capsules |

EXAMPLE 8

200 mg Dose Immediate Release Capsule

A 200 mg dose immediate release capsule formulation was prepared having the following composition:

TABLE 8

| INGREDIENT | AMOUNT (mg) | REPRESENTATIVE BATCH AMOUNT (kg) |
|---|---|---|
| Eplerenone | 200.0 | 20.00 |
| Lactose, Hydrous NF | 147.8 | 14.78 |
| Microcrystalline Cellulose, NF | 29.0 | 2.90 |

TABLE 8-continued

| INGREDIENT | AMOUNT (mg) | REPRESENTATIVE BATCH AMOUNT (kg) |
|---|---|---|
| Talc, USP | 10.0 | 1.00 |
| Croscarmellose Sodium, NF | 8.0 | 0.80 |
| Sodium Lauryl Sulfate, NF | 2.0 | 0.20 |
| Colloidal Silicon Dioxide, NF | 2.0 | 0.20 |
| Magnesium Stearate, NF | 1.2 | 0.12 |
| Total Capsule Fill Weight | 400.0 | 40.00 |
| Hard Gelatin Capsule, Size #0, White Opaque | 1 Capsule | 100,000 Capsules |

EXAMPLE 9

Oral Solution

A series of oral solutions is prepared containing 2.5 mg/L of eplerenone and having the following composition: up to 20% ethanol v/v; up to 10% propylene glycol v/v; about 10% to 70% glycerol v/v; and about 30% to 70% water v/v.

Another series of oral solutions is prepared containing 2.5 mg/L of eplerenone and further comprising ethanol, propylene glycol, polyethylene glycol 400, glycerin and 70% w/w sorbitol.

Another oral solution is prepared in the following manner. A 15% hydroxypropyl-β-cyclodextrin solution (20 mL) is added to a bottle containing eplerenone (100 mg). The bottle containing the mixture is placed in a temperature controlled water bath/shaker at 65° C. and shaken for 20 minutes. The bottle is removed from the water bath and permitted to cool at room temperature for about five minutes. Apple juice (60 mL, commercially available) is added to the mixture in the bottle and the contents of the bottle are gently swirled.

The oral solutions of this example are particularly useful in the treatment of, for example, non-ambulatory patients, pediatric patients and patients that have difficulty taking solid dosage forms such as tablets and capsules.

EXAMPLE 10

Tablets

Tablets containing a 100 mg dose of eplerenone and having the composition set forth in Table 10A were prepared by wet granulation (total batch size of 70 g). These 100 mg dose tablets had an average disintegration time of about 16 minutes and an average tablet hardness of about 16 kP to 17 kP.

TABLE 10A

| INGREDIENT | WEIGHT FRACTION (%) |
|---|---|
| Eplerenone | 30.0 |
| Lactose, Hydrous | 25.0 |
| Avicel ®, PH 101 | 37.5 |
| Ac-Di-Sol ™ | 2.0 |
| Pharmacoat ™ 603 | 3.0 |
| Sodium Lauryl Sulfate, NF | 1.0 |

TABLE 10A-continued

| INGREDIENT | WEIGHT FRACTION (%) |
|---|---|
| Talc | 1.0 |
| Magnesium Stearate | 0.5 |
| Total | 100 |

The composition set forth in Table 10A was then modified by adjusting the Ac-Di-Sol™ weight fraction of the composition to values from 2% to 5%, while maintaining the weight fraction ratio of lactose/Avicel® at 25/37.5. Tablets containing a 100 mg dose of eplerenone and having these modified compositions were prepared by wet granulation (total batch size of 70 g). The mean disintegration results for these 100 mg dose tablets are reported in Table 10B below. An increase of the Ac-Di-Sol™ weight fraction to 5% resulted in a reduction in disintegration time to less than 10 minutes where no other change was made to the composition.

TABLE 10B

| AC-DI-SOL ™ WEIGHT FRACTION (%) | DISINTEGRATION TIME (MINUTES) |
|---|---|
| 2 | 14.11 ± 0.74 |
| 3 | 13.90 ± 0.34 |
| 4 | 13.84 ± 0.62 |
| 5 | 6.88 ± 0.48 |

The composition was then further modified as set forth in Table 10C to evaluate the effect on disintegration time of adding the disintegrant extragranularly (that is, the ingredient is added after the wet granulated mixture had been dried) as well as intragranularly (that is, the ingredient is present in the mixture during the wet granulation step). The weight fraction ratio of lactose/Avicel® for these compositions also was adjusted about 43/17.5 to about 45/17.5 to increase the compressibility of the compositions. Tablets containing a 100 mg dose of eplerenone and having these modified compositions were prepared by wet granulation (total batch size of 70 g). The mean disintegration results for these 100 mg dose tablets are reported in Table 10C below. The addition of 5% Ac-Di-Sol™ or the addition of 1.5% Ac-Di-Sol™ intragranular/1.5% Ac-Di-Sol™ extragranular/10% Avicel® improved disintegration time up to about seven to nine minutes. The Explotab™ brand of sodium starch glycolate used in the compositions is commercially available from Mendel.

TABLE 10C

| DISINTEGRANT WEIGHT FRACTION (%) | DISINTEGRATION TIME (MINUTES) |
|---|---|
| 2% Ac-Di-Sol ™ intra* | 12.6 ± 0.49 |
| 2% Ac-Di-Sol ™ intra/ 1% Ac-Di-Sol ™ extra* | 9.98 ± 1.15 |
| 1.5% Ac-Di-Sol ™ intra/ 1.5% Ac-Di-Sol ™ extra | 11.98 ± 0.54 |
| 2% Ac-Di-Sol ™ intra/ 2% Ac-Di-Sol ™ extra | 9.96 ± 0.31 |
| 4 Ac-Di-Sol ™ intra/ 1% Ac-Di-Sol ™ extra | 8.36 ± 0.64 |
| 4% Ac-Di-Sol ™ intra/ 1% Ac-Di-Sol ™ extra in | 8.48 ± 0.53 |

TABLE 10C-continued

| DISINTEGRANT WEIGHT FRACTION (%) | DISINTEGRATION TIME (MINUTES) |
|---|---|
| 1% sodium lauryl sulfate solution | |
| 2% Explotab ™ intra | 17.32 ± 0.71 |
| 1.5% Ac-Di-Sol ™ intra/ 1.5% Explotab ™ extra | 12.38 ± 0.41 |
| 1.5% Ac-Di-Sol ™ intra/ 1.5% Ac-Di-Sol ™ extra/ 10% Avicel ® extra | 7.90 ± 0.53 |

*intra = intagranularly; extra = extragranularly.

The batch sizes for the 2% Ac-Di-Sol™ intragranular/1% Ac-Di-Sol™ extragranular composition and the 5% Ac-Di-Sol™ intragranular composition discussed above were scaled up from 70 g to 2 kg. Tablets containing a 100 mg dose of eplerenone and having these compositions were prepared by wet granulation. The results for these 100 mg dose tablets are reported in Table 10D below. The term "Granulation Time" as used in this example and throughout the other examples of this application means the total time for water addition and post-addition mixing.

TABLE 10D

| PARAMETER MEASURED | 70 g BATCH (2% Ac-Di-Sol ™ intra*/ 1% Ac-Di-Sol ™ extra*) | 2 kg BATCH (2% Ac-Di-Sol ™ intra*/ 1% Ac-Di-Sol ™ extra*) | 2 kg BATCH (5% Ac-Di-Sol ™ intra*) |
|---|---|---|---|
| % Water Added | 35 | 27.48 | 40.82 |
| Granulation Time (minutes) | 5.16 | 5.16 | 5.00 |
| Drying Time (minutes) | 32 | 23 | 30 |
| Moisture Content (%) | 2.0 | 2.15 | 2.2 |
| Granule Density (g/cc) | 0.55 | 0.632 | 0.62 |
| Tablet Hardness (kp) | 16.57 | 9.41 | 10.27 |
| Tablet Thickness (mm) | 4.38 | 4.39 | 4.33 |
| % Friability | 0.357 | 0.264 | — |
| Disintegration Time (minutes) | — | 12.86 | 9.15 |

*See Table 10C.

A decrease in tablet hardness was observed for the tablets prepared from the 2 kg batches relative to the tablets prepared from the 70 kg batch. In view of this decrease in tablet hardness, the 5% Ac-Di-Sol™ intragranular composition was modified by removing 10% intragranular Avicel® and replacing it with 10% extragranular Avicel®. Tablets containing a 100 mg dose of eplerenone and having the 5% Ac-Di-Solυ intragranular composition or the 5% Ac-Di-Sol™ intragranular/7.5% intragranular Avicel® 10% extragranular Avicel composition were prepared by wet granulation (total batch sizes of 2 kg). The experimental results for these 100 mg dose tablets are reported in Table 10E below. Removing 10% intragranular microcrystalline cellulose and replacing it with 10% extragranular microcrystalline cellulose resulted in (i) decreased density, (ii) increased tablet hardness, (iii) decreased disintegration time, and (iv) decreased water requirements for the wet granulation step.

TABLE 10E

| PARAMETER MEASURED | 2 kg BATCH (5% Ac-Di-Sol ™ intra*) | 2 kg BATCH (5% Ac-Di-Sol ™ intra/10% Avicel ® extra*) |
|---|---|---|
| % Water Added | 40.82 | 36.59 |
| Granulation Time (minutes) | 5 | 4.5 |
| Bulk Density (g/cc) | 0.62 | 0.535 |
| Tablet Hardness (kp) | 11 (low compression force), 11 (high compression force) | 14.5 (low compression force), 18 (high compression force) |
| Disintegration Time (minutes) | 9.15 | 6.31 |

* See Table 10C.

The 5% Ac-Di-Sol™ intragranular/7.5% intragranular Avicel® 10% extragranular Avicel® composition was prepared as set forth in Table 10F. Tablets containing a 100 mg dose of eplerenone and having this composition were prepared by wet granulation (total batch sizes of 2 kg and 10 kg).

TABLE 10F

| INGREDIENT | WEIGHT FRACTION (%) |
|---|---|
| Eplerenone | 30 |
| Lactose, Hydrous | 42 |
| Avicel ®, PH 101 | 7.5 intra/10 extra |
| Ac-Di-Sol ™ | 5 |
| Pharmacoat ™ 603 | 3 |
| Sodium Lauryl Sulfate, NF | 1 |
| Talc | 1 |
| Magnesium Stearate | 0.5 |
| Total | 100 |

* See Table 10C.

The experimental results for these 100 mg dose tablets are reported in Table 10G below. Scale-up of this formulation was achieved without a drop in tablet hardness, while maintaining disintegration time at about seven minutes.

TABLE 10G

| PARAMETER MEASURED | 2 kg BATCH | 10 kg BATCH |
|---|---|---|
| % Water Added | 36.59 | 30.52 |
| Granulation Time (minutes) | 4.5 | 5.25 |
| Drying Time (minutes) | 27 | 11 |
| Granule Density (g/cc) | 0.535 | 0.549 |
| Tablet Hardness (kp) | 11.71 | 12.84 |
| Tablet Thickness (mm) | 4.47 | 4.37 |
| % Friability | 0.223 | 0.38 |
| Disintegration Time (minutes) | 6.31 | 7.00 |

EXAMPLE 11

Two Hour Controlled Release Tablet

A controlled release tablet (tablet weight 333.3 mg; round, standard, concave, 12/32") containing a 100 mg dose of eplerenone was prepared. The tablet had the following composition:

TABLE 11

| INGREDIENT | WEIGHT % OF TABLET |
|---|---|
| Eplerenone | 30.0 |
| Lactose Monohydrate | 40.0 |
| Microcrystalline Cellulose (Avicel ® PH 101) | 19.5 |
| Hydroxypropyl methylcellulose (Methocel ® K4M Premium) | 6.0 |
| Hydroxypropyl methylcellulose (Pharmacoat ™ 603) | 3.0 |
| Talc | 1.0 |
| Magnesium Stearate | 0.5 |
| Total | 100 |

EXAMPLE 12

Four Hour Controlled Release Tablet

Controlled release tablets (round standard concave) containing 50 mg (9/32"), 100 mg (12/32") and 150 mg (14/32") doses of eplerenone were prepared. The tablets had the following compositions:

TABLE 12

| | WEIGHT % OF TABLET | | |
|---|---|---|---|
| INGREDIENT | 50 mg | 100 mg | 150 mg |
| Eplerenone | 30.0 | 30.0 | 30.0 |
| Lactose Monohydrate | 27.0 | 35.7 | 37.0 |
| Microcrystalline Cellulose (Avicel ® PH 101) | 13.5 | 17.8 | 18.5 |
| Hydroxypropyl methylcellulose (Methocel ® K4M Premium) | 25.0 | 12.0 | 10.0 |
| Hydroxypropyl methylcellulose (Pharmacoat ™ 603) | 3.0 | 3.0 | 3.0 |
| Talc | 1.0 | 1.0 | 1.0 |
| Magnesium Stearate | 0.5 | 0.5 | 0.5 |
| Total | 100 | 100 | 100 |

EXAMPLE 13

Six Hour Controlled Release Tablet

A controlled release tablet (tablet weight 333.3 mg; round, standard, concave, 12/32") containing a 100 mg dose of eplerenone was prepared. The tablet had the following composition:

TABLE 13

| INGREDIENT | WEIGHT % OF TABLET |
|---|---|
| Eplerenone | 30.0 |
| Lactose Monohydrate | 30.5 |
| Microcrystalline Cellulose (Avicel ® PH 101) | 15.0 |
| Hydroxypropyl methylcellulose (Methocel ® K4M Premium) | 20.0 |
| Hydroxypropyl methylcellulose (Pharmacoat ™ 603) | 3.0 |
| Talc | 1.0 |
| Magnesium Stearate | 0.5 |
| Total | 100 |

EXAMPLE 14

Tablets

Tablets containing a 100 mg dose or a 200 mg dose of eplerenone and having one of the compositions set forth in Table 14A below were prepared by wet granulation (total batch size of 1 kg). In addition, tablets containing a 100 mg dose or a 200 mg dose of eplerenone and having formulation C set forth in Table 14A were prepared by wet granulation (total batch size of 2 kg).

TABLE 14A

| | WEIGHT FRACTION OF TABLET (%) | | | | | |
|---|---|---|---|---|---|---|
| INGREDIENT | A | B | C | D | E | F |
| Eplerenone | 30 | 30 | 30 | 30 | 30 | 30 |
| Lactose Monohydrate | 10 | 40 | 10 | 40 | 25 | 25 |
| Microcrystalline Cellulose (Avicel ® PH 101) | 50.5 | 20.5 | 35.5 | 5.5 | 28 | 28 |
| Hydroxypropyl methylcellulose (Methocel ® K4M Premium) | 5 | 5 | 20 | 20 | 12.5 | 12.5 |
| Hydroxypropyl methylcellulose (Pharmacoat ™ 603) | 3 | 3 | 3 | 3 | 3 | 3 |
| Talc | 1 | 1 | 1 | 1 | 1 | 1 |
| Magnesium Stearate | 0.5 | 0.5 | 0.5 | 0.5 | 0.5 | 0.5 |
| Total | 100 | 100 | 100 | 100 | 100 | 100 |

Tablets prepared from the 2 kg batch (Formulation C) exhibited a loss of tablet hardness and compressibility relative to tablets prepared from the 1 kg batch (Formulation C). Average tablet hardness for the 100 mg dose tablets prepared from the 2 kg batch was about 7 kP. Average tablet hardness for the 200 mg dose tablets prepared from the 1 kg batch was about 9 kP. In comparative tests it was noted that placebo granulations with a high microcrystalline cellulose weight fraction (for example, about 65.5%) did not compress into tablets. With respect to the 2 kg batch, it also was observed that the granulation time of about 10 to 12 minutes resulted in an increased loss of water due to evaporation during granulation relative to the 1 kg batch.

Tablets were then prepared containing a 100 mg dose of eplerenone and having the composition of Formulation C above or the composition of Formulation C above wherein the lactose and Avicel® weight fractions were reversed. The tablets were prepared by wet granulation (total batch size of 70 g) using different granulation times. Tablet compression was carried out on an F3 single punch press. As shown in Table 14B below, the combination of longer granulation times and higher microcrystalline cellulose content resulted in a loss of hardness. Sensitivity to granulation conditions decreased when the lactose/microcrystalline cellulose ratio was adjusted from 10/35.5 to 30.5/15.

TABLE 14B

| LACTOSE/ AVICEL ® RATIO | MOISTURE CONTENT (%) | HARD- NESS (kP) | FRIABILITY (%) | GRANULATION TIME* (minutes) |
|---|---|---|---|---|
| 10/35.5 | 1.37 | 17.84 | 0.1783 | 5 (single-step water addition) |
| 10/35.5 | 2.65 | 10.65 | 0.846 | 6.5 (multi-step water addition) |
| 10/35.5 | 3.2 | 18.75 | 0.230 | 4.6 (single-step water addition) |
| 30.5/15 | 1 | 16.18 | 0.1047 | 4.1 (single-step water addition) |
| 30.5/15 | 2.01 | 15.90 | 0.0824 | 3.85 (single-step water addition) |
| 30.5/15 | 3.95 | 15.77 | 0.2947 | 4.46 (single-step water addition) |
| 30.5/15 | 1.12 | 14.86 | 0.365 | 4.13 (single-step water addition) |
| 30.5/15 | 2.57 | 14.41 | 0.263 | 6.91 (single-step water addition) |
| 30.5/15 | 1.99 | 14.28 | 0.243 | 6.91 (multi-step water addition) |

*Granulation Time = water addition + post-mixing times.

Controlled release ("CR") tablets containing a 100 mg dose of eplerenone and having one of the compositions set forth in Table 14C below were prepared by wet granulation (total batch size of 70 g). The average in vitro dissolution times in 1% SDS in water for each composition were then measured. The 2 hour 100 mg dose CR tablet was 37% dissolved at two hours. The 4 hour 100 mg dose CR tablet was 42% dissolved at four hours. The 6 hour 100 mg dose CR tablet was 54% dissolved at six hours.

TABLE 14C

| | WEIGHT % OF TABLET | | |
|---|---|---|---|
| INGREDIENT | 2 Hour CR | 4 Hour CR | 6 Hour CR |
| Eplerenone | 30 | 30 | 30 |
| Lactose Monohydrate | 40 | 36 | 30.5 |
| Microcrystalline Cellulose (Avicel ® PH 101) | 17.5 | 15.5 | 15 |
| Hydroxypropyl methylcellulose (Methocel ® K4M Premium) | 8 | 14 | 20 |
| Hydroxypropyl methylcellulose (Pharmacoat ™ 603) | 3 | 3 | 3 |
| Talc | 1 | 1 | 1 |
| Magnesium Stearate | 0.5 | 0.5 | 0.5 |
| Total | 100 | 100 | 100 |

Two hour CR, 4 hour CR, and 6 hour CR tablets containing a 100 mg dose of eplerenone were prepared by wet granulation in a scaled-up process (total batch sizes of 2 kg and 10 kg). The tablets had the same compositions as set forth in Table 14C above except that the 2 hour CR and 4 hour CR tablet compositions had high molecular weight hydroxypropyl methylcellulose (Methocel® K4M Premium) weight fractions of 6% and 12%, respectively, and microcrystalline cellulose weight fractions of 19.5% and 17.5%, respectively. Tables 14D, 14E and 14F report the experimental results. Dissolution profiles can be further adjusted by appropriate selection of high molecular weight hydroxypropyl methylcellulose concentrations. In addition, dissolution time decreases as hydroxypropyl methylcellulose particle size increases. This is likely due to poor hydration of the hydroxypropyl methylcellulose matrix as particle size increases. Smaller particle size, on the other hand, appears to cause rapid hydration of the matrix and therefore slower drug release rate.

TABLE 14D

| PARAMETER MEASURED | 2 Hour CR Tablet (100 mg Dose) | | |
|---|---|---|---|
| | 70 g BATCH[1] | 2 kg BATCH | 10 kg BATCH |
| % Water Added | 38.57 | 30.71 | 29.71 |
| Granulation Time (minutes) | 4.00 | 4.07 | 4.00 |
| Drying Time (minutes) | 60 | 30 | 11 |
| Moisture Content (%) | 2.0 | 1.28 | 1.62 |
| Granule Density (g/cc) | 0.55 | 0.58 | 0.63 |
| Tablet Hardness (kp) | 14.05 | 13.79 | 11.37 |
| Tablet Thickness (mm) | 4.58 | 4.40 | 4.4 |
| % Friability | 0.351 | 0.263 | 0.39 |

[1]Tablets prepared from the 70 g batch had the composition set forth in Table 14C.

TABLE 14E

| PARAMETER MEASURED | 4 Hour CR Tablet (100 mg Dose) | | |
|---|---|---|---|
| | 70 g BATCH[1] | 2 kg BATCH | 10 kg BATCH |
| % Water Added | 41.42 | 29.67 | 31.26 |
| Granulation time (minutes) | 4.00 | 4.25 | 6.25 |
| Drying Time (minutes) | 45 | 27 | 11 |
| Moisture Content (%) | 1.2 | 2.21 | 1.18 |
| Granule Density (g/cc) | 0.536 | 0.513 | 0.60 |
| Tablet Hardness (kp) | 14.8 | 11.5 | 12.4 |
| Tablet Thickness (mm) | 4.59 | 4.43 | 4.58 |
| % Friability | 0.219 | 0.323 | 0.213 |

[1]Tablets prepared from the 70 g batch had the composition set forth in Table 14C.

TABLE 14F

| PARAMETER MEASURED | 6 Hour CR Tablet (100 mg Dose) | | |
|---|---|---|---|
| | 70 g BATCH[1] | 2 kg BATCH | 10 kg BATCH |
| % Water Added | 45.71 | 37.73 | 35.35 |
| Granulation Time (minutes) | 4.13 | 4.00 | 5.5 |
| Drying Time (minutes) | 45 | 35 | 12 |
| Moisture Content (%) | 1.12 | 1.4 | 0.68 |
| Granule Density (g/cc) | 0.523 | 0.536 | 0.561 |
| Tablet Hardness (kp) | 14.9 | 13.7 | 12.4 |
| Tablet Thickness (mm) | 4.64 | 4.56 | 4.58 |
| % Friability | 0.365 | 0.141 | 0.12 |

Compositions containing varying amounts of hydroxypropyl methylcellulose (HPMC) were prepared, compressed into different tablet sizes, and evaluated for dissolution time. The hydroxypropyl methylcellulose weight fraction of each composition is set forth in Tables 14G and 14H below. The eplerenone, Pharmacoat™ 603, talc and magnesium stearate weight fractions were fixed at 30%, 3%, 1% and 0.5%, respectively. The ratio of lactose/microcrystalline cellulose was fixed at 2:1 and the amount of lactose and microcrystalline cellulose adjusted accordingly to accommodate the change in hydroxypropyl methylcellulose (HPMC) concentration. Tables 14G and 14H below report mean dissolution results in 1% SDS for the compositions. Table 14G reports the approximate times at which the tablets had achieved an in vitro dissolution of 50%, whereas Table 14H reports the in vitro dissolution in 1% SDS achieved at 24 hours. In general, dissolution rate increased as tablet size decreased and/or when tablet shape was changed from standard round shape to a caplet shape.

TABLE 14G

| DOSE (PUNCH SIZE) | APPROXIMATE TIME OF 50% IN VITRO DISSOLUTION (HOURS) | | | | |
|---|---|---|---|---|---|
| | 6% HPMC | 15% HPMC | 25% HPMC | 35% HPMC | 45% HPMC |
| 25 mg (7/32") | — | — | 3.12 | 4.35 | 5.78 |
| 62 mg (10/32") | — | 4.00 | — | — | 7.54 |
| 100 mg (12/32") | 2.41 | — | 5.88 | — | 4.24 |
| 125 mg (13/32") | — | 5.5 | — | 21.33 | — |
| 150 mg (14/32") | 4.11 | 3.00 | 16.62 | — | — |

TABLE 14H

| DOSE (PUNCH SIZE) | DISSOLUTION AT 24 (HOURS) (%) | | | | |
|---|---|---|---|---|---|
| | 6% HPMC | 15% HPMC | 25% HPMC | 35% HPMC | 45% HPMC |
| 25 mg (7/32") | — | — | 107 | 102 | 83 |
| 62 mg (10/32") | — | 98 | — | 86 | 69 |
| 100 mg (12/32") | 104 | — | 68 | — | 80 |
| 125 mg (13/32") | — | 83 | — | 52 | — |
| 150 mg (14/32") | 101 | 131 | 56 | — | — |

Table 14I further summarizes the results of Table 14G above with respect to 4 hour CR compositions. Based on the experimental data, hydroxypropyl methylcellulose (HPMC) concentrations of 35%, 25%, 12%, and 10% can be used with eplerenone dosages of 25 mg, 50 mg, 100 mg and 150 mg to achieve 50% in vitro dissolution in 1% SDS times ($DT_{50}$) of about 4 hours.

TABLE 14I

| EPLERENONE DOSE (mg) | HPMC WEIGHT FRACTION (%) | PUNCH SIZE (ROUND, SC) | TABLET WEIGHT (mg) | RELEASE MATCHED TO $DT_{50} = 4$ HOURS |
|---|---|---|---|---|
| 25 | 30 | 7/32" | 83.3 | no |
| 25 | 35 | 7/32" | 83.3 | yes |
| 50 | 20 | 9/32" | 166.6 | no |
| 50 | 25 | 9/32" | 166.6 | yes |
| 100 | 12 | 12/32" | 333.3 | yes |
| 150 | 6 | 14/32" | 500 | no |
| 150 | 10 | 14/32" | 500 | yes |

EXAMPLE 15

Disintegration Tests

Six identical tablets were separately placed into one of six tubes having a wire mesh screen bottom in a disintegration basket. A water bath was preheated to 37° C.±2° C. and maintained at that temperature for the duration of the disintegration test. A 1000 mL beaker was placed in the water bath. The beaker was filled with a sufficient amount of water to ensure that the wire mesh screen of the tubes remained at least 2.5 cm below the water surface during the test. The disintegration basket was inserted in the water at time=0 minutes and repeatedly raised and lowered until the test was complete, while maintaining the wire mesh screen of the tubes at least 2.5 cm below the water surface. Disintegration time for each tablet was the time at which the very last portion of the tablet passed through the screen at the bottom of the tube. The mean results for each type of tablet tested are reported in Table 15.

TABLE 15

| TABLET | DISINTEGRATION TIME |
|---|---|
| Example 1: 25 mg Dose Tablet (Coated) | 8 minutes, 6 seconds |
| Example 1: 25 mg Dose Tablet (Uncoated) | 6 minutes, 16 seconds |
| Example 2: 50 mg Dose Tablet (Coated) | 9 minutes, 17 seconds |
| Example 2: 50 mg Dose Tablet (Uncoated) | 7 minutes, 39 seconds |
| Example 3: 100 mg Dose | 10 minutes, |

TABLE 15-continued

| TABLET | DISINTEGRATION TIME |
|---|---|
| Tablet (Coated) | 30 seconds |
| Example 3: 100 mg Dose Tablet (Uncoated) | 8 minutes, 24 seconds |

EXAMPLE 16

Immediate Release Dissolution Tests

The apparatus of U.S.P. II (with paddles) was used to determine the dissolution rate in 1% SDS of the tablets of Examples 1, 2 and 3 for both coated and uncoated immediate release tablets. A 1000 ML 1% sodium lauryl sulfate (SDS)/99% water solution was used as the dissolution fluid. The solution was maintained at a temperature of 37° C.±0.5° C. and stirred at 50 rpm during the test. Twelve identical tablets were tested. The 12 tablets were each separately placed in one of 12 standard dissolution vessels at time=0 minutes. At time=15, 30, 45 and 60 minutes, a 5 mL aliquot of solution was removed from each vessel. The sample from each vessel was filtered and the absorbance of the sample measured (UV spectrophotometer; 2 mm path length quartz cell; 243 nm or wavelength of UV maxima; blank: dissolution medium). Percent dissolution was calculated based on the measured absorbances. The results of the dissolution tests are reported in Table 16A.

TABLE 16A

| TABLET | DISSOLUTION (%) AT VARIOUS TIMES (MINUTES) | | | |
|---|---|---|---|---|
|  | 15 | 30 | 45 | 60 |
| Example 1: 25 mg Dose Tablet (Coated) | 92 | 99 | 100 | 101 |
| Example 1: 25 mg Dose Tablet (Uncoated) | 92 | 98 | 99 | 99 |
| Example 2: 50 mg Dose Tablet (Coated) | 90 | 100 | 102 | 103 |
| Example 2: 50 mg Dose Tablet (Uncoated) | 89 | 97 | 98 | 98 |
| Example 3: 100 mg Dose Tablet (Coated) | 82 | 95 | 97 | 98 |
| Example 3: 100 mg Dose Tablet (Uncoated) | 84 | 94 | 96 | 96 |

A similar study was carried out using 100 mg coated tablets prepared as discussed in Example 3 in which the eplerenone had a $D_{90}$ particle size of 45 microns, as in Example 3, 165 microns and 227 microns. Six tablets were used for each study rather than twelve as above. The results of that study are shown in Table 16B, below. The particle size distribution of those three samples is shown in Table 16C, hereinafter.

TABLE 16B

| TABLET | DISSOLUTION (%) AT VARIOUS TIMES (MINUTES) | | | | |
|---|---|---|---|---|---|
|  | 15 | 30 | 45 | 60 | 90 |
| Example 3: $D_{90}$ = 45 microns | 69 | 87 | 93 | 95 | 97 |

TABLE 16B-continued

| TABLET | DISSOLUTION (%) AT VARIOUS TIMES (MINUTES) | | | | |
|---|---|---|---|---|---|
|  | 15 | 30 | 45 | 60 | 90 |
| Example 3: $D_{90}$ = 165 microns | 57 | 80 | 90 | 95 | 102 |
| Example 3: $D_{90}$ = 227 microns | 47 | 69 | 80 | 87 | 100 |

TABLE 16C

| | Micronized Eplerenone Particle Size Distribution in Microns | | |
|---|---|---|---|
| $D_{value}$ | $D_{90}$ = 45 | $D_{90}$ = 165 | $D_{90}$ = 227 |
| $D_5$ | 1.7 | 4 | 6.5 |
| $D_{10}$ | 2.7 | 9 | 18 |
| $D_{50}$ | 13.3 | 75 | 102 |
| $D_{75}$ | 27 | 119 | 164 |
| $D_{90}$ | 44.7 | 165 | 227 |
| $D_{95}$ | 58.3 | 196 | 265 |

EXAMPLE 17

Controlled Release Dissolution Tests

The procedure of Example 16 using 1% SDS was followed to test the 100 mg dose controlled release tablets of Examples 11 and 13 and the 50 mg, 100 g and 150 mg dose controlled release tablets of Example 12. The mean results of the dissolution tests are reported in Table 17.

TABLE 17

| | Dissolution (%) | | | | |
|---|---|---|---|---|---|
| | 2 Hour CR Tablet (Example | 4 Hour CR Tablet (Example 12) | | | 6 Hour CR Tablet (Example |
| Time (Hours) | 11: 100 mg Dose) | 50 mg Dose | 100 mg Dose | 150 mg Dose | 13: 100 mg Dose) |
| 0.5 | 5 | 6 | 7 | 7 | 4 |
| 1 | 8 | 12 | 13 | 13 | 7 |
| 2 | 18 | 25 | 27 | 26 | 15 |
| 3 | 29 | 38 | 40 | 39 | 24 |
| 4 | 48 | 51 | 53 | 51 | 33 |
| 6 | 86 | 74 | 74 | 71 | 49 |
| 8 | 100 | 87 | 91 | 87 | 64 |
| 9 | — | 97 | 101 | 100 | — |
| 24 | 104 | — | — | — | 105 |

EXAMPLE 18

Particle Size Analysis

Table 18 shows the results of a particle size sieve analysis of small scale wet granulated batches of the pharmaceutical compositions of Examples 1, 11, 12 and 13 prior to compression into the tablets. "Cumulative Percent of Batch" reports the percent of the total batch having a particle size larger than the indicated sieve size.

TABLE 18

| | CUMULATIVE PERCENT OF BATCH | | | |
|---|---|---|---|---|
| SIEVE SIZE (MICRONS) | IR* (Ex. 1 Comp.) | 2 Hour CR (Ex. 11 Comp.) | 4 Hour CR (Ex. 12 Comp. - 100 mg Dose) | 6 Hour CR (Ex. 13 Comp.) |
| Fines | 100.00 | 100.00 | 100.00 | 100.00 |
| 63 (230 mesh screen) | 91.13 | 88.68 | 88.37 | 84.11 |
| 106 (140 mesh screen) | 79.97 | 76.53 | 70.92 | 68.26 |
| 180 (80 mesh screen) | 57.10 | 65.71 | 52.88 | 51.12 |
| 250 (60 mesh screen) | 35.19 | 57.81 | 42.62 | 41.58 |
| 300 (50 mesh screen) | 22.54 | 51.64 | 36.34 | 35.07 |
| 425 (40 mesh screen) | 8.85 | 40.60 | 27.31 | 26.21 |

*IR = immediate release; CR = controlled release; Ex. = example; Comp. = composition.

EXAMPLE 19

Bulk Density Analysis

Table 19 shows the mean results of a bulk density analysis of several small scale wet granulated batches of the pharmaceutical compositions of Examples 1, 11, 12 and 13 prior to compression into the tablets:

TABLE 19

| COMPOSITION | BULK DENSITY (g/mL$^3$) |
|---|---|
| Example 1: Immediate Release | 0.568 |
| Example 11: 2 Hour Controlled Release | 0.622 |
| Example 11: 4 Hour Controlled Release | 0.565 |
| Example 1: 4 Hour Controlled Release | 0.473 |
| Example 1: 4 Hour Controlled Release | 0.487 |
| Example 1: 4 Hour Controlled Release | 0.468 |
| Example 1: 6 Hour Controlled Release | 0.528 |

EXAMPLE 20

Tablet Analysis Program

Table 20 shows the results of the tablet analysis program ("TAP analysis") for a sampling of tablets of having the composition of the tablets of Examples 1, 2, 3, 11, 12 and 13.

TABLE 20

| TABLETS TESTED (N = 10) | AVERAGE WEIGHT (mg) | AVERAGE THICKNESS (mm) | HARDNESS (kP) |
|---|---|---|---|
| Example 1: 25 mg Dose (IR*, Film Coated) | 88.5 | 3.3157 | 7.64 |
| Example 1: 25 mg Dose (IR, Uncoated) | 85.5 | 3.2845 | 4.55 |
| Example 2: 50 mg Dose (IR, Uncoated) | 170.5 | 4.0297 | 7.31 |
| Example 2: 50 mg Dose (IR, Film Coated) | 176.0 | 4.093 | 10.95 |
| Example 3: 100 mg Dose (IR, Uncoated) | 340.7 | 4.4902 | 9.92 |
| Example 3: 100 mg Dose (IR, Film Coated) | 349.6 | 4.546 | 13.91 |
| Example 11: 100 mg Dose (2 Hour CR*) | 329.7 | 4.412 | 11.53 |
| Example 12: 50 mg Dose (4 Hour CR) | 160.0 | 4.1723 | 10.55 |
| Example 12: 100 mg Dose (4 Hour CR) | 331.4 | 4.6672 | 14.62 |
| Example 12: 150 mg Dose (4 Hour CR) | 498.7 | 5.4440 | 11.63 |
| Example 13: 100 mg Dose (6 Hour CR) | 335.1 | 4.8242 | 11.05 |

See Table 19 notes.

EXAMPLE 21

Friability Test

Twenty tablets were weighed and placed in a rotating drum. Extraneous dust was first removed from the drum and the tablets. The drum was started and rotation continued for ten minutes at a minimum of 25 rotations per minute. The rotation of the drum was stopped and the tablets removed. Loose dust on the tablets as well as any broken tablets were removed and the intact tablets were weighed. The percent loss of the test samples from Examples 1, 2, 3, 11, 12 and 13 was calculated and is reported below in Table 21.

TABLE 21

| TABLETS | PERCENT LOSS |
|---|---|
| Example 1: 100 mg Dose (IR*) | 0.177 |
| Example 2: 50 mg Dose (IR) | 0.236 |
| Example 3: 25 mg Dose (IR) | 0.000 |
| Example 11: 100 mg Dose (2 Hour CR*) | 0.42 |
| Example 12: 100 mg Dose (4 Hour CR) | 0.33 |
| Example 13: 100 mg Dose (6 Hour CR) | 0.12 |

See Table 19 notes.

EXAMPLE 22

Preparation of Immediate Release Tablet

Figure 1B:
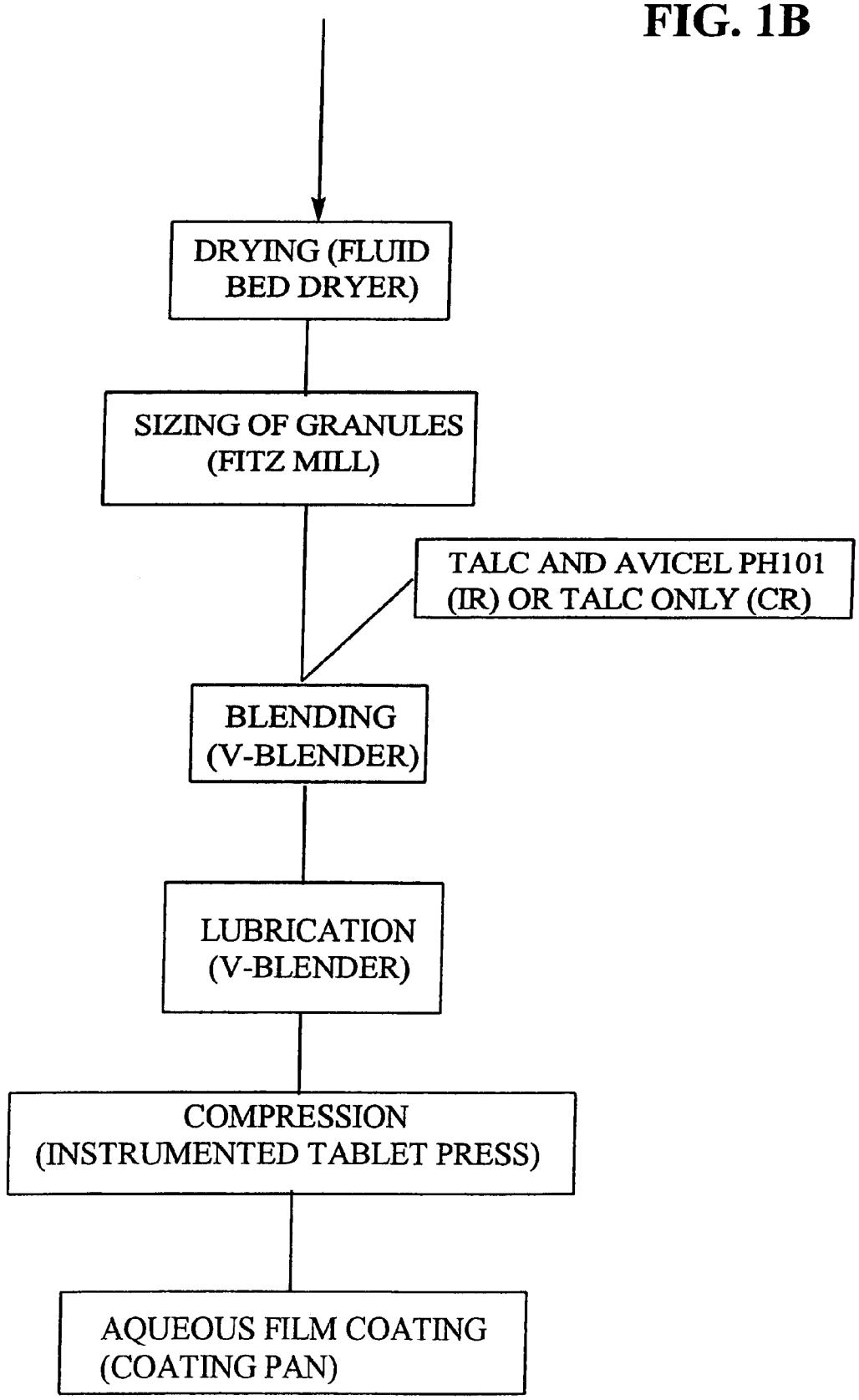

The ingredients of the pharmaceutical compositions of the present invention can be prepared in accordance with acceptable pharmaceutical manufacturing practices in the manner illustrated by the flow of FIGS. 1A and 1B for small scale preparations.

An illustrative formulation process using the starting materials of Table 22 is set forth below. The process can be operated as a single batch reaction or as two or more parallel batch reactions.

TABLE 22

| INGREDIENT | WEIGHT % OF TABLET | AMOUNT OF STARTING MATERIAL (KG/BATCH) |
|---|---|---|
| Eplerenone | 29.41 | 4.412 |
| Lactose Monohydrate (#310, NF) | 42.00 | 6.3 |
| Microcrystalline Cellulose (intragranular) (NF, Avicel ® PH101) | 7.50 | 1.125 |
| Croscarmellose Sodium (NF, Ac-Di-Sol ™) | 5.00 | 0.75 |
| Hydroxypropyl Methylcellulose (#2910, USP, Pharmacoat ™ 603) | 3.00 | 0.45 |
| Sodium Lauryl Sulfate (NF) | 1.00 | 0.15 |
| Sterile water for irrigation | | |
| Talc (USP) | 1.00 | 0.15 |
| Microcrystalline Cellulose (extragranular) (NF, Avicel ® PH101) | 10.59 | 1.588 |
| Magnesium Stearate (NF) | 0.50 | 0.075 |
| Total | 100.00 | 15.00 |

Milling: The eplerenone was milled in a jet mill. The resulting milled eplerenone had $D_{10}$, $D_{50}$ and $D_{90}$ values of 2.65 microns, 23.3 microns and 99.93 microns, respectively. In other words, 10%, 50% and 90% of the eplerenone particles were less than 2.65 microns, 23.3 microns and 99.93 microns, respectively, in size. A pin mill is preferred for preparation on a manufacturing scale.

Dry Mixing: A 65 L Niro™ Fielder granulator was loaded with the lactose, eplerenone, Avicel®, Ac-Di-Sol™, Pharmacoat™ 603 and sodium lauryl sulfate in this order. These materials were mixed to homogeneity (about three minutes) with the main blade on the slow main blade setting and the chopper blade on the slow chopper blade setting. For manufacturing scale, a machine such as a Bukler Perkins™ 1000L granulator can be used.

Wet Granulation: The dry powder mixture was wet granulated using USP water. The main blade and chopper blade of the granulator were placed on the fast speed setting. Five kilograms of water were added to the mixture over a period of about three minutes using a Masterflex™ water pump, model 7524-00 (24" tubing). The rate of water addition was about 1.66 kg/minute. The wet mixture was blended for an additional minute to ensure the uniform distribution of the water in the granulation. The wet granulated mixture was about 38% water by weight.

Drying: The wet granulation was placed in a Freund™ Flo-coater (FLF-15) fluid bed dryer. The inlet air temperature was adjusted to about 68° C. and the granulation was dried in the fluid bed dryer to reduce the moisture content to between 0.5% to 2.5%. Moisture content was monitored using a Computrac™ Moisture Analyzer.

Dry Screening: The dry granules were passed through a fitz mill with a 20# screen, knives forward, and 2400 rpm speed.

Blending and Lubrication: The dry granules were then placed in a PK 2 cubic foot V-blender. The talc and extragranular Avicel® 101 were placed on top of the granules and the mixture blended to homogeneity (about 10 minutes). The magnesium stearate was placed on top of the mixture and the mixture blended for an additional three minutes. A Croff™ Flow blender can be used for large scale preparations.

Compression: The granules were then compressed on a Killian™ table press to the desired weight and hardness using appropriate size tooling. The target weight, size and hardness for 25, 50 and 100 mg tablets was as set forth in Table 22A below:

TABLE 22A

| Dosage of eplerenone (mg) | Tablet weight (mg) | Tooling size (inch) (round, standard concave) | Target hardness range (kP) |
|---|---|---|---|
| 25 | 85 | 7/32 | 3-9 |
| 50 | 170 | 9/32 | 5-14 |
| 100 | 340 | 12/32 | 8-16 |

Film Coating: Sterile water for irrigation was placed in a stainless steel container equipped with an electric mixer with a stainless steel impeller (Lightnin™ TSM 2500). The mixer was turned on at an appropriate speed. Opadry®, white (YS-1-18027-A) was slowly added to the vortex while avoiding the formation of foam to provide a solution having an Opadry® to water weight ratio of 15:85. Mixing continued for an additional 30 minutes or until all the material was dispersed and a homogeneous suspension observed. Constant slow stirring was maintained during the coating process. Coating of the tablets was carried out in the conventional manner using a Vector™ Hi Coater VHC-1355 with 35 L coating pan with two spray guns.

EXAMPLE 23

Preparation of Controlled Release Tablet

An illustrative formulation process using the starting materials of Table 23 is set forth below. The process can be operated as a single batch reaction or as two or more parallel batch reactions.

TABLE 23

| INGREDIENT | WEIGHT % OF TABLET 100 mg Tablet | AMOUNT/BATCH (kg) |
|---|---|---|
| Eplerenone | 30.0 | 3.0 |
| Lactose Monohydrate | 34.0 | 3.4 |
| Microcrystalline Cellulose (Avicel ® PH 101) | 19.5 | 1.95 |
| Hydroxypropyl methylcellulose (Methocel ® K4M Premium) | 12.0 | 1.2 |
| Hydroxypropyl methylcellulose (Pharmacoat ™ 603) | 3.0 | 0.3 |
| Talc | 1.0 | 0.1 |
| Magnesium Stearate | 0.5 | 0.05 |
| Total | 100 | 10 |

Dry Mixing: A 60 L Baker Perkins™ blender was loaded with the lactose, micronized eplerenone, Avicel®, Methocel® K4M, and Pharmacoat™ 603 in this order. These materials were mixed for three minutes with the main blade on the slow main blade setting and the chopper blade on the slow chopper blade setting.

Wet granulation: The dry powder mixture was wet granulated using USP water. The main blade and chopper blade of the blender were placed on the fast speed setting. About 3.1 kg of water was added to the mixture over a period of about three minutes using an Aeromatic™ water pump. The rate of water addition was about 995 g/minute. The wet mixture was blended for an additional minute to ensure the uniform distribution of the water in the granulation. The wet granulated mixture was about 31% water by weight.

Drying: The wet granulation was placed in an Aeromatic™ fluid bed dryer. The inlet air temperature was set at about 60° C. and the granulation was dried in the fluid bed dryer to reduce the moisture content to between 1% to 3%. Moisture content of the granules was monitored using a Computrac™ Moisture Analyzer.

Dry Screening: The dry granules were passed through a fitz mill (D6A) with 20# screen, knives forward and medium speed (1500–2500 rpm). The milled granules were collected in a polyethylene bag.

Lubrication: The dry granules were placed in a PK 2 cubic foot V-blender. The talc was placed on top of the granulation and blended for 5 minutes. The magnesium stearate was then placed on top of the granulation and blended for 3 minutes. The granulation was discharged from the blender into a fiber drum lined with double polyethylene bags.

Compression: The granulation was compressed on a Korsch™ tablet press to the desired weight and hardness using 12/32" round standard concave tooling. Target weight was 333.3 mg and target hardness was 11–13 kP for 100 mg tablets.

Film Coating: USP water was added to a stainless steel container and stirred by an electric mixer with a stainless steel impeller at slow speed. Opadry® (white: YS-1-18027-A) was slowly added to the vortex. The stirring speed was increased as necessary to disperse the Opadry® in the water (10% opadry/90% water w/w) while avoiding the formation of foam. Mixing continued for 30 minutes or until all the material was dispersed and a homogeneous suspension was observed. The suspension was kept under constant slow stirring during coating.

Coating: A Compulab™ Coater with 36" coating pan and one spray gun was used. The atomization air was set at 45 psi. The tablets were weighed and the amount of the coating suspension required to be sprayed in order to give 3% weight gain for tablets was determined. The tablets were loaded in the pan and the air flow set to 700 cubic feet per minute. The tablets were allowed to warm up for approximately 10 minutes by jogging the pan every two minutes. The inlet air temperature was set at 65° C. The exhaust temperature obtained was about 45° C. Rotation of the pan at 10 rpm was initiated and spraying starting. The spray rate was set at 50 g/min. The process was monitoring by checking and recording the coating parameters at each time interval. The coating process continued until the required quantity of coating suspension was sprayed, at which time spraying was discontinued. Pan rotation continued for an additional two to five minutes. The air heater was turned off and the pan rotation stopped. The tablets were allowed to cool for 10 minutes and the pan was jogged every two minutes during cooling. The coated tablets were discharged from the coating pan into fiber drums lined with double polyethylene bags.

EXAMPLE 24

Single Dose Safety and Pharmacokinetic Study

The pharmacokinetics, safety and antialdosterone activity of single 10, 50, 100, 300 and 1000 mg oral doses of eplerenone were evaluated in a single-center, randomized, double-blind, placebo-controlled study.

It was determined that in plasma eplerenone exists in equilibrium with the inactive open lactone ring form of eplerenone. The pharmacokinetics of this inactive open lactone ring form of eplerenone was also evaluated. The study employed seven parallel dose groups of eight healthy male humans. Each subject received a single dose of one of the following: (i) a 10 mg dose of eplerenone (one 10 mg dose capsule), (ii) a 50 mg dose of eplerenone (two 25 mg dose capsules), (iii) a 100 mg dose of eplerenone (one 100 mg dose capsule), (iv) a 300 mg dose of eplerenone (three 100 mg dose capsules), (v) a 1000 mg dose of eplerenone (five 200 mg dose capsules), (vi) a 50 mg dose of spironolactone, or (vii) a placebo. The pharmacokinetic profiles were evaluated using the measured blood and urine levels of eplerenone, the open lactone ring form of eplerenone and spironolactone.

Antialdosterone activity was determined based on urine levels of sodium and potassium following repeated administration of fludrocortisone. Safety was determined on the basis of laboratory tests, vital signs, and the occurrence and types of adverse events.

The eplerenone capsules administered corresponded to the capsules (or combinations of the capsules) disclosed in Examples 4, 5, 7 and 8 above. The placebo was a conventional capsule containing lactose. The spironolactone used in the study was obtained from Searle Canada (Oakville, Ontario). The fludrocortisone used in the study consisted of commercially available fludrocortisone tablets (Florinef®, Squibb BV).

The subjects, who underwent a ten hour food fast prior to administration of the dose, received a single oral dose of one of the study medications together with about 180 mL of water at 0800 hours. All subjects received a 1.0 mg dose of fludrocortisone nine hours before administration of the study medication; a 0.5 mg dose of fludrocortisone at the time of administration of the study medication; a 0.1 mg dose of fludrocortisone at 2, 4, 6, 8, 10, 12 and 14 hours after administration of the study medication; and a 0.5 mg dose of fludrocortisone 16 hours after administration of the study medication. Each dose of fludrocortisone was administered with 150 mL of water except for the 1.0 mg dose which was administered with 200 mL of water.

A 12-lead ECG was obtained prior to dosing (within one hour) and at 2, 3, 4 and 24 hours after administration of the study medication. Body temperature (oral), respiratory rate, and pulse rate and blood pressure (after sitting for three minutes) were obtained prior to dosing (within one hour) and at 0.25, 0.5, 1, 2, 4, 8, 12, and 24 hours after administration of the study medication. Blood samples were collected at −0.25 (predose), 0.5, 1, 2, 3, 4, 6, 8, 12, 16, 24, 28, 32, 48, 72 and 96 hours post dose. Urine samples were collected for the following periods: −9 to 0; 0 to 2; 2 to 4; 4 to 6; 6 to 8; 8 to 10; 10 to 12; 12 to 14; 14 to 16; and 16 to 24 hours.

The plasma samples collected from subjects dosed with eplerenone were assayed for concentrations of eplerenone and the open lactone ring form of eplerenone. The plasma samples of the subjects dosed with spironolactone were assayed for concentration of spironolactone and its active metabolites canrenone, 7α-thiomethylspirolactone, and 6β-hydroxy-7α-thiomethylspirolactone. A subset of plasma samples was also assayed for testosterone levels. The urine collected was analyzed to determine concentrations and amounts of eplerenone and the open lactone ring form of eplerenone, the amount of sodium and potassium excreted, and the urinary $\log_{10}$ (sodium/potassium) ratio. The mean results obtained from the subjects tested are reported in Tables 24A through 24J below. There were no clinically significant changes in physical examinations, vital signs or clinical laboratory results. All adverse events were mild in severity.

TABLE 24A

| Time After Dosing (hours) | Plasma Concentration Of Eplerenone or Spironolactone (ng/mL) | | | | | |
|---|---|---|---|---|---|---|
| | 10 mg (Epl.*) | 50 mg (Epl.) | 100 mg (Epl.) | 300 mg (Epl.) | 1000 mg (Epl.) | 50 mg (Spi*) |
| −0.25 | 0 | 0 | 0 | 0 | 0 | 0 |
| 0.5 | 130.4 | 552.5 | 758.0 | 1619.6 | 3176.03 | 10.5 |
| 1.0 | 177.0 | 720.6 | 1224.6 | 2676.3 | 5258.8 | 23.6 |
| 2.0 | 158.6 | 692.9 | 1363.8 | 2775.0 | 5940.0 | 14.4 |
| 3.0 | 125.4 | 591.5 | 1113.5 | 2225.0 | 6810.0 | 14.3 |
| 4.0 | 105.7 | 456.6 | 900.1 | 1951.3 | 6128.8 | 4.8 |
| 6.0 | 65.3 | 269.8 | 558.5 | 1266.6 | 4150.0 | 0 |
| 8.0 | 34.4 | 146.4 | 275.3 | 842.9 | 2827.5 | 0 |
| 12.0 | 6.0 | 49.4 | 124.0 | 333.0 | 1335.1 | 0 |
| 16.0 | 6.0 | 18.3 | 41.9 | 141.9 | 646.8 | 0 |
| 24.0 | 1.7 | 3.0 | 13.1 | 38.3 | 208.0 | 0 |
| 28.0 | 0 | 1.8 | 6.1 | 21.1 | 107.1 | 0 |
| 32.0 | 0 | 0 | 3.0 | 11.3 | 61.7 | 0 |
| 48.0 | 0 | 0 | 0 | 1.7 | 22.3 | 0 |
| 72.0 | 0 | 0 | 0 | 0 | 1.4 | 0 |
| 96.0 | 0 | 0 | 0 | 0 | 0 | 0 |

*Epl. = eplerenone; Spi = spironolactone.

The data demonstrated a linear relationship between eplerenone dose and plasma concentration for the eplerenone dosages evaluated.

TABLE 24B

| Pharmaco-kinetic Parameter | Pharmacokinetic Parameter Value (Epl. = Eplerenone) | | | | |
|---|---|---|---|---|---|
| | 10 mg (Epl.) | 50 mg (Epl.) | 100 mg (Epl.) | 300 mg (Epl.) | 1000 mg (Epl.) |
| $AUC_{(0-96)}$ (ng/mL) hr | 941.5 | 4017.0 | 7943.4 | 18451.4 | 56435.3 |
| $C_{max}$ (ng/mL) | 191.3 | 797.0 | 1505.0 | 2967.5 | 7261.3 |
| $T_{max}$ (hours) | 1.3 | 1.4 | 1.5 | 1.5 | 2.5 |
| $T_{½}$ (hours) | 2.1 | 2.9 | 4.9 | 3.7 | 15.1 |
| Mean Residence Time (hours) | 3.9 | 4.2 | 4.9 | 5.5 | 7.0 |
| Oral Clearance (L/hr) | 13.3 | 13.7 | 13.1 | 17.6 | 18.4 |

TABLE 24C

| Time After Dosing (hours) | Plasma Concentration Of Open Ring Lactone (ng/mL) | | | | |
|---|---|---|---|---|---|
| | 10 mg (Epl.)[1] | 50 mg (Epl.) | 100 mg (Epl.) | 300 mg (Epl.) | 1000 mg (Epl.) |
| −0.25 | 0 | 0 | 0 | 0 | 0 |
| 0.5 | 1.2 | 24.3 | 33.9 | 123.0 | 191.3 |
| 1.0 | 1.0 | 34.5 | 50.3 | 203.2 | 359.9 |
| 2.0 | 0 | 27.1 | 48.8 | 177.9 | 405.8 |
| 3.0 | 0 | 22.5 | 40.3 | 141.4 | 453.3 |
| 4.0 | 0 | 17.5 | 30.6 | 116.7 | 392.3 |
| 6.0 | 0 | 9.5 | 19.0 | 74.0 | 285.3 |
| 8.0 | 0 | 3.3 | 6.5 | 45.1 | 167.9 |
| 12.0 | 0 | 0 | 0 | 15.3 | 73.7 |
| 16.0 | 0 | 0 | 0 | 2.1 | 36.9 |
| 24.0 | 0 | 0 | 0 | 0 | 8.3 |
| 28.0 | 0 | 0 | 0 | 0 | 3.2 |
| 32.0 | 0 | 0 | 0 | 0 | 1.8 |
| 48.0 | 0 | 0 | 0 | 0 | 0 |
| 72.0 | 0 | 0 | 0 | 0 | 0 |

[1]Most concentrations were below the assay detection limit; Epl. = eplerenone.

Plasma concentration of eplerenone was about 15 to 20 times greater than plasma concentrations of the open ring lactone form.

TABLE 24D

| Pharmaco-kinetic Parameter | Pharmacokinetic Parameter Value (Open Ring Lactone) | | | | |
|---|---|---|---|---|---|
| | 10 mg (Epl.*) | 50 mg (Epl.) | 100 mg (Epl.) | 300 mg (Epl.) | 1000 mg (Epl.) |
| $AUC_{(0-96)}$ (ng/mL) hr | — | 142.8 | 246.8 | 1065.1 | 3483.5 |
| $C_{max}$ (ng/mL) | — | 36.4 | 60.4 | 211.8 | 521.5 |
| $T_{max}$ (hours) | — | 1.0 | 1.1 | 1.3 | 2.5 |
| $T_{½}$ (hours) | — | 2.7 | 2.7 | 2.8 | 2.6 |
| Mean Residence Time (hours) | — | 2.8 | 3.3 | 4.2 | 5.7 |
| Oral Clearance (L/hr) | — | 491.3 | 445.2 | 299.8 | 330.7 |

*Epl. = eplerenone.

TABLE 24E

| Time Post Dosing (hours) | Plasma Concentration Of Testosterone (ng/mL) | | | | | | |
|---|---|---|---|---|---|---|---|
| | Placebo | 10 mg (Epl.*) | 50 mg (Epl.) | 100 mg (Epl.) | 300 mg (Epl.) | 1000 mg (Epl.) | 50 mg (Spi.*) |
| −0.25 | 5.6 | 5.2 | 6.5 | 6.4 | 5.7 | 6.5 | 5.5 |
| 0.5 | — | 5.5 | — | — | — | — | — |
| 1.0 | 5.0 | 4.6 | 6.0 | 5.6 | 5.5 | 5.7 | 5.6 |
| 2.0 | 5.1 | 4.6 | 6.1 | 5.8 | 5.3 | 5.4 | 5.1 |
| 3.0 | — | — | 7.1 | — | — | 6.9 | — |
| 4.0 | 4.4 | 4.3 | 5.1 | 4.8 | 5.2 | 5.1 | 4.3 |
| 6.0 | 3.5 | 3.6 | 4.4 | 3.8 | 4.1 | 4.5 | 3.3 |
| 8.0 | 3.8 | 3.8 | 4.3 | 3.8 | 4.5 | 4.7 | 3.5 |
| 12.0 | 3.4 | 3.2 | 4.5 | 4.0 | 4.3 | 4.0 | 3.6 |
| 24.0 | 6.1 | 5.3 | 7.4 | 6.0 | 6.3 | 7.2 | 6.0 |
| 48.0 | 5.1 | 4.7 | 6.1 | 6.0 | 5.7 | 6.5 | 5.2 |

*See notes to Table 24B.

TABLE 24F

Concentration (Amount) of Eplerenone Excreted in Urine [ng/mL; (mcg)]

| Collection Period | 10 mg (Epl.*) | 50 mg (Epl.) | 100 mg (Epl.) | 300 mg (Epl.) | 1000 mg (Epl.) |
|---|---|---|---|---|---|
| −9 to 0 hours | 0 (0) | 0 (0) | 0 (0) | 0 (0) | 0 (0) |
| 0 to 2 hours | 278.0 (21.6) | 1252.2 (99.2) | 2623.3 (360.2) | 9370.01 (677.7) | 17858.6 (1482.0) |
| 2 to 4 hours | 191.1 (35.8) | 1064.6 (175.3) | 2305.6 (407.6) | 6465.9 (873.7) | 24460.3 (5983.3) |
| 4 to 6 hours | 107.2 (16.5) | 518.3 (60.6) | 1157.3 (285.1) | 3865.2 (672.6) | 13899.7 (4041.5) |
| 6 to 8 hours | 63.8 (7.6) | 307.3 (30.7) | 627.6 (158.8) | 2237.8 (337.0) | 8782.1 (2083.0) |
| 8 to 10 hours | 0 (0) | 172.4 (27.6) | 362.9 (69.1) | 1208.6 (307.9) | 4491.0 (1853.9) |
| 10 to 12 hours | 0 (0) | 72.7 (16.5) | 146.6 (44.7) | 542.4 (162.4) | 2361.1 (1177.2) |
| 12 to 14 hours | 0 (0) | 23.1 (11.3) | 110.3 (26.6) | 419.6 (97.4) | 3183.7 (892.8) |
| 14 to 16 hours | 0 (0) | 21.6 (1.5) | 36.5 (6.6) | 292.6 (52.2) | 1405.2 (340.5) |
| 16 to 24 hours | 0 (0) | 13.1 (4.0) | 7.1 (2.7) | 126.4 (50.3) | 658.0 (366.0) |
| 0 to 24 hours | (78.8) | (410.6) | (1271.4) | (2872.3) | (17246.6) |

See notes to Table 24B.

TABLE 24G

Concentration (Amount) of Open Ring Lactone Excreted in Urine [ng/mL; (mcg)]

| Collection Period | 10 mg (Epl.*) | 50 mg (Epl.) | 100 mg (Epl.) | 300 mg (Epl.) | 1000 mg (Epl.) |
|---|---|---|---|---|---|
| −9 to 0 hours | 0 (0) | 0 (0) | 0 (0) | 0 (0) | 0 (0) |
| 0 to 2 hours | 1781.8 (130.9) | 9833.2 (689.1) | 12079.2 (1079.2) | 47865.1 (3357.2) | 60184.4 (4589.2) |
| 2 to 4 hours | 854.1 (144.5) | 6839.0 (801.3) | 9309.8 (1355.4) | 27970.5 (3923.5) | 56341.5 (12603.2) |
| 4 to 6 hours | 532.7 (77.3) | 3789.4 (404.3) | 3712.5 (796.7) | 16280.0 (2679.3) | 28771.3 (8481.4) |
| 6 to 8 hours | 513.3 (50.3) | 2776.2 (268.0) | 2688.1 (507.1) | 11626.0 (1718.3) | 27599.7 (5904.1) |
| 8 to 10 hours | 130.3 (25.1) | 1091.0 (156.3) | 1400.6 (246.7) | 4425.1 (1053.8) | 9952.4 (3566.2) |
| 10 to 12 hours | 44.8 (11.0) | 461.6 (91.3) | 536.5 (154.5) | 1965.5 (580.9) | 4822.7 (2212.1) |
| 12 to 14 hours | 38.8 (7.4) | 264.9 (64.0) | 431.6 (98.2) | 1841.2 (426.7) | 5549.0 (1932.3) |
| 14 to 16 hours | 26.4 (3.2) | 359.9 (33.7) | 241.4 (51.1) | 1448.3 (259.8) | 3877.4 (920.4) |
| 16 to 24 hours | 0 (0) | 131.1 (42.8) | 133.1 (58.8) | 721.8 (287.8) | 2835.8 (1381.6) |
| 0 to 24 hours | (433.3) | (2431.2) | (4077.9) | (12699.9) | (39017.9) |

*See notes to Table 24B.

Excretion of total eplerenone (that is, eplerenone and its open ring lactone form) in the urine represented approximately 5% of the dose for all doses administered. Urinary excretion of total eplerenone occurred almost entirely within the first 24 hours after dosing.

TABLE 24H

Urinary $\log_{10}$ (Sodium/Potassium) Ratio

| Collection Period | Placebo | 10 mg (Epl.*) | 50 mg (Epl.) | 100 mg (Epl.) | 300 mg (Epl.) | 1000 mg (Epl.) | 50 mg (Spi.*) |
|---|---|---|---|---|---|---|---|
| −9 to 0 hours | 0.920 | 0.918 | 0.960 | 0.874 | 1.026 | 0.985 | 1.006 |
| 0 to 2 hours | 0.675 | 0.313 | 0.703 | 0.463 | 0.761 | 0.956 | 0.657 |
| 2 to 4 hours | 0.643 | 0.435 | 0.901 | 0.795 | 1.140 | 1.313 | 0.860 |
| 4 to 6 hours | 0.448 | 0.401 | 0.900 | 0.901 | 1.231 | 1.398 | 0.904 |
| 6 to 8 hours | 0.590 | 0.618 | 0.906 | 0.970 | 1.451 | 1.594 | 1.023 |
| 8 to 10 hours | 0.583 | 0.578 | 0.769 | 0.735 | 1.265 | 1.451 | 0.865 |
| 10 to 12 hours | 0.625 | 0.614 | 0.797 | 0.564 | 1.123 | 1.389 | 0.821 |

*See notes to table 24B.

Administration of the aldosterone agonist fludrocortisone resulted in a decreased urinary $\log_{10}$ (sodium/potassium) ratio. Administration of a 50 mg or larger dose of eplerenone reversed the effect of the fludrocortisone over a 12 hour period with a corresponding increase in sodium excretion.

TABLE 24I

Urinary Sodium Excretion (mmol)

| Collection Period | Placebo | 10 mg (Epl.*) | 50 mg (Epl.) | 100 mg (Epl.) | 300 mg (Epl.) | 1000 mg (Epl.) | 50 mg (Spi.*) |
|---|---|---|---|---|---|---|---|
| −9 to 0 hours | 28.8 | 33.4 | 29.2 | 25.7 | 32.8 | 32.8 | 29.1 |
| 0 to 2 hours | 6.5 | 4.8 | 6.1 | 5.6 | 5.8 | 9.3 | 4.1 |
| 2 to 4 hours | 7.2 | 7.3 | 10.3 | 11.7 | 15.7 | 28.1 | 8.5 |
| 4 to 6 hours | 5.9 | 4.3 | 10.2 | 15.0 | 21.9 | 29.9 | 9.4 |
| 6 to 8 hours | 6.0 | 6.2 | 9.0 | 17.9 | 23.3 | 36.1 | 14.8 |
| 8 to 10 hours | 7.2 | 7.0 | 9.4 | 13.0 | 25.6 | 46.8 | 13.4 |
| 10 to 12 hours | 8.1 | 7.1 | 10.8 | 7.3 | 16.1 | 29.3 | 8.4 |
| 12 to 14 hours | 9.6 | 10.0 | 11.7 | 10.2 | 17.5 | 44.2 | 11.5 |
| 14 to 16 hours | 6.7 | 4.2 | 4.0 | 4.2 | 8.6 | 17.0 | 5.9 |
| 16 to 24 hours | 5.3 | 6.8 | 7.3 | 6.6 | 10.0 | 18.8 | 11.8 |

See notes to Table 24B.

TABLE 24J

Urinary Potassium Excretion (mmol)

| Collection Period | Placebo | 10 mg (Epl.*) | 50 mg (Epl.) | 100 mg (Epl.) | 300 mg (Epl.) | 1000 mg (Epl.) | 50 mg (Spi.*) |
|---|---|---|---|---|---|---|---|
| −9 to 0 hours | 34.2 | 36.8 | 29.9 | 33.8 | 29.9 | 34.1 | 26.9 |
| 0 to 2 hours | 10.3 | 12.8 | 10.0 | 13.7 | 8.4 | 9.8 | 7.5 |
| 2 to 4 hours | 14.9 | 17.4 | 13.8 | 15.1 | 10.9 | 13.9 | 11.8 |

TABLE 24J-continued

Urinary Potassium Excretion (mmol)

| Collection Period | Placebo | 10 mg (Epl.*) | 50 mg (Epl.) | 100 mg (Epl.) | 300 mg (Epl.) | 1000 mg (Epl.) | 50 mg (Spi.*) |
|---|---|---|---|---|---|---|---|
| 4 to 6 hours | 15.9 | 13.9 | 12.7 | 17.2 | 12.4 | 12.2 | 10.2 |
| 6 to 8 hours | 12.0 | 12.9 | 11.3 | 15.2 | 7.9 | 9.9 | 13.3 |
| 8 to 10 hours | 15.5 | 16.7 | 15.5 | 18.2 | 14.0 | 16.6 | 17.9 |
| 10 to 12 hours | 16.2 | 15.8 | 16.3 | 15.0 | 12.2 | 12.1 | 12.5 |
| 12 to 14 hours | 20.5 | 24.9 | 23.3 | 21.6 | 19.3 | 21.8 | 20.6 |
| 14 to 16 hours | 13.1 | 13.3 | 9.8 | 11.4 | 10.5 | 9.3 | 11.4 |
| 16 to 24 hours | 25.3 | 27.6 | 28.3 | 29.3 | 21.5 | 25.7 | 27.9 |

See notes to Table 24B.

The data demonstrate a linear relationship between eplerenone dose and antialdosterone activity. Urinary sodium excretion and urinary $\log_{10}$ (sodium/potassium) ratio increased with increasing eplerenone doses.

EXAMPLE 25

Absorption, Distribution, Metabolism and Elimination Study

An open-label, single dose study was employed to evaluate the absorption, distribution, metabolism and elimination profile of a single 100 mg dose of an oral solution of eplerenone. The pharmacokinetics of the inactive open lactone ring form of eplerenone was also evaluated.

The study employed eight healthy male humans. Each subject received a single 100 mg oral dose of a solution of [$^{14}$C]eplerenone (specific activity 0.75 µCi/mg). Plasma, saliva, breath, urine and fecal samples were collected at predetermined intervals and analyzed for sample radioactivity and the concentration of eplerenone and its open lactone ring form. Safety was determined on the basis of laboratory tests, vital signs, and the occurrence and types of adverse events.

The subjects, who underwent an overnight food fast prior to administration of the dose, received at 0800 hours a single 100 mg oral dose of an aqueous oral solution of radiolabeled eplerenone reconstituted in 80 mL of an apple juice/hydroxypropyl-β-cyclodextrin mixture. The subjects swallowed about 200 mL of water one, two and three hours post dosing.

A 12-lead ECG was obtained prior to dosing (within one hour) and at 2, 3, 4 and 24 hours after administration of the study medication. Body temperature (oral), respiratory rate, and pulse rate and blood pressure (after sitting three minutes) were obtained prior to dosing (within one-half hour) and at 0.5, 1, 4, and 24 hours after administration (dosing) of the study medication. Blood samples were collected at −0.5 (predose), 0.5, 1, 1.5, 2, 2.5, 3, 4, 6, 8, 12, 16, 24, 36, 48, 72 and 96 hours post dose. Urine samples were collected for the following periods: −12 to 0; 0 to 2; 2 to 4; 4 to 8; 8 to 12; 12 to 24; 24 to 48; 72 to 96; 96 to 120; 120 to 144; and 144 to 168 hours. Individual fecal samples were collected beginning immediately after dosing and continuing through 0800 hours on day 8. In addition, one predose fecal sample was provided. Saliva samples were taken at 0.5 hour predose and at 0.5, 1, 2, 4, 6, 12, and 24 hours postdose. Breath samples were taken at 0.5 hour predose and at 1, 2, 3, 4, 6, 8, 12, 24, 36, 48 and 72 hours postdose.

The data show that elimination of eplerenone is by metabolism and not excretion of unchanged eplerenone. The mean percentages of the dose excreted as total radioactivity in urine and feces were 66.6% and 32.0%, respectively. The majority of urinary and fecal radioactivity was due to metabolites and less than 15% was due to eplerenone. The mean percentages of the dose excreted in urine as eplerenone and its open lactone ring form were 1.65% and 4.98%, respectively. The mean percentages of the dose excreted in feces as eplerenone and its open lactone ring form were 0.807% and 2.46%, respectively. There were no clinically significant changes in physical examinations, vital signs or clinical laboratory test results. There were no serious adverse effects.

There were no detectable concentrations of total radioactivity in the breath collected at any of the time points from any of the subjects. The mean percentage of total radioactivity bound to plasma proteins in the 1.5 hour plasma samples was 49.4%. The mean concentration of total radioactivity in these samples was 2.39 µg/mL. When [$^{14}$C] eplerenone was spiked into the control plasma, which had been frozen, the percentage of eplerenone bound was 40.4% at a concentration of 14.5 µg/mL.

The mean results of selected tests are reported in Tables 25A, 25B, 25C and 25D below.

TABLE 25A

| Pharmacokinetic Parameter | Total Radioactivity | | |
|---|---|---|---|
| | Plasma (+ SEM) | Whole Blood (+ SEM) | Saliva (+ SEM) |
| $AUC_{0-inf}$ (ng equivalents) hr/mL) | 18400 ± 1200 | 12800 ± 800 | 7960 ± 500 |
| $C_{max}$ (ng equivalents/mL | 2490 ± 110 | 1770 ± 80 | 2170 ± 280 |
| $T_{max}$ (hour) | 1.3 ± 0.2 | 1.1 ± 0.2 | 0.6 ± 0.1 |

TABLE 25B

| | Plasma Concentration (ng/mL) | |
|---|---|---|
| Time After Dosing (hours) | Eplerenone | Open Lactone Ring Form |
| −0.5 | 0 | 0 |
| 0.5 | 1345.0 | 63.2 |
| 1.0 | 1617.5 | 78.0 |
| 1.5 | 1591.3 | 70.8 |
| 2.0 | 1418.8 | 59.9 |
| 2.5 | 1258.1 | 51.0 |
| 3.0 | 1176.3 | 46.9 |
| 4.0 | 1001.4 | 41.9 |
| 6.0 | 595.5 | 23.0 |
| 8.0 | 390.6 | 13.0 |
| 12.0 | 148.6 | 1.9 |
| 16.0 | 68.0 | 0 |
| 24.0 | 17.3 | 0 |
| 36.0 | 0 | 0 |
| 48.0 | 0 | 0 |

TABLE 25B-continued

| Time After Dosing (hours) | Plasma Concentration (ng/mL) | |
|---|---|---|
| | Eplerenone | Open Lactone Ring Form |
| 72.0 | 0 | 0 |
| 96.0 | 0 | 0 |

TABLE 25C

Plasma Pharmacokinetic Parameters

| | Eplerenone | Open Lactone Ring Form |
|---|---|---|
| $AUC_{(0-96)}$ (ng/mL) hr | 9537.2 | 352.2 |
| $C_{max}$ (ng/mL) | 1721.3 | 82.8 |
| $T_{max}$ (hours) | 1.3 | 1.1 |
| $T_{½}$ (hours) | 3.8 | 3.1 |
| Mean Residence Time (hours) | 4.8 | 3.4 |
| Oral Clearance (L/hr) | 11.4 | 306.3 |

TABLE 25D

| | Urinary Excretion | | | |
|---|---|---|---|---|
| | Eplereone | | Open Lactone Ring Form | |
| Collection Period | Concentration (ng/mL) | Amount (mcg) | Concentration (ng/mL) | Amount (mcg) |
| −12 to 0 hours | 0 | 0 | 0 | 0 |
| 0 to 2 hours | 2933.4 | 457.5 | 9004.8 | 1345.3 |

TABLE 25D-continued

| | Urinary Excretion | | | |
|---|---|---|---|---|
| | Eplereone | | Open Lactone Ring Form | |
| Collection Period | Concentration (ng/mL) | Amount (mcg) | Concentration (ng/mL) | Amount (mcg) |
| 2 to 4 hours | 1635.2 | 622.0 | 4235.1 | 1249.6 |
| 4 to 8 hours | 1067.0 | 314.0 | 4717.1 | 1349.8 |
| 8 to 12 hours | 388.9 | 158.0 | 1555.7 | 596.2 |
| 12 to 24 hours | 99.5 | 95.7 | 438.0 | 400.0 |
| 24 to 48 hours | 0 | 0 | 22.2 | 38.8 |
| 48 to 72 hours | 0 | 0 | 0 | 0 |

Over 90% of the urinary radioactivity was excreted within the first 24 hours, indicating rapid elimination of the eplerenone and its metabolites. The majority of urinary and fecal radioactivity was due to metabolites, indicating extensive metabolism by the liver.

EXAMPLE 26

Bioavailability Study

The bioavailability and safety of five different formulations (each containing a 100 mg dose of eplerenone) were evaluated in an open-label, randomized, single dose, five-way crossover study of a group of healthy adult humans. The subjects received five single doses of 100 mg of eplerenone administered as (i) one eplerenone 100 mg immediate release (IR) capsule, (ii) one eplerenone 100 mg immediate release (IR) tablet, (iii) one eplerenone 100 mg controlled release (CR) tablet with a 50% in vitro dissolution time of two hours, (iv) one eplerenone 100 mg controlled release (CR) tablet with a 50% in vitro dissolution time of four hours, and (iv) one eplerenone 100 mg controlled release (R) tablet with a 50% in vitro dissolution time of six hours. A total of 13 subjects began the study with nine subjects completing all five treatments. Treatments were separated by seven days. The specific pharmaceutical compositions of each formulation are reported in Table 26A.

TABLE 26A

| | WEIGHT % OF TABLET/CAPSULE | | | | |
|---|---|---|---|---|---|
| INGREDIENT | IR Capsule (T.* A.) | IR Tablet (T. B) | Two Hour CR Tablet[1] (T. C) | Four Hour CR Tablet[2] (T. D) | Six Hour CR Tablet[3] (T. E) |
| Eplerenone | 25 | 30 | 30 | 30 | 30 |
| Lactose Monohydrate | 57.86 (Fast-6 Flo ™ lactose) | 42 | 40 | 34 | 30.5 |
| Microcrystalline Cellulose (Avicel ® PH 101) | 11.34 (Avicel ® PH 102) | 17.5 (7.5% intra[4] plus 10% extra[4]) | 19.5 | 19.5 | 15 |
| Croscarmellose Sodium (Ac-Di-Sol ™) | 2 | 5 | — | — | — |
| Methocel ® K4M Premium | — | — | 6 | 12 | 20 |
| Hydroxypropyl Methylcellulose (Pharmacoat ™ 603) | — | 3 | 3 | 3 | 3 |
| Sodium Lauryl Sulfate | 0.5 | 1 | — | — | — |

TABLE 26A-continued

| | WEIGHT % OF TABLET/CAPSULE | | | | |
|---|---|---|---|---|---|
| INGREDIENT | IR Capsule (T.* A.) | IR Tablet (T. B) | Two Hour CR Tablet[1] (T. C) | Four Hour CR Tablet[2] (T. D) | Six Hour CR Tablet[3] (T. E) |
| Talc | 2.5 | 1 | 1 | 1 | 1 |
| Magnesium Stearate | 0.3 | 0.5 | 0.5 | 0.5 | 0.5 |
| Colloidal Silicon Dioxide | 0.5 | — | — | — | — |
| Total | 100 | 100 | 100 | 100 | 100 |

[1] 50% in vitro dissolution time of 2 hours.
[2] 50% in vitro dissolution time of 4 hours.
[3] 50% in vitro dissolution time of 6 hours.
*T. = treatment.
[4] intra = intragranular; extra = extragranular.

The subjects, who underwent an eight hour food fast and a one hour water fast prior to administration of each dose, received a single oral dose of one of the study medications on days 1, 8, 15, 22 and 29 in one of five randomized treatment sequences (ABDCE, BCAED, CDEAB, DECBA, and EABDC). The medication was administered together with about 180 mL of water at 0800 hours. Blood samples were collected at −0.5 (predose), 0.5, 1, 2, 3, 4, 6, 8, 10, 12, 16, 24, 36 and 48 hours post dose. Urine samples were collected and pooled between the hours of 0–24 and 24–48 hours postdose. Analyses of the separated plasma and urine for eplerenone and its inactive open lactone ring form were performed at Phoenix International Life Sciences, Quebec, Canada. Plasma and urinary concentrations of eplerenone and its inactive open lactone ring form were determined using a validated high performance liquid chromatography ("HPLC") procedure for the inactive open lactone ring form. The lower limits of detection in urine were approximately 50 ng/mL for both eplerenone and the inactive form. The mean results obtained are reported in Tables 26B, 26C, 26D and 26E below. Table 26F illustrates micronized eplerenone particle size distribution in microns for several of the preparations used in this Example.

TABLE 26B

| | Plasma Concentration Of Eplerenone (ng/mL) | | | | |
|---|---|---|---|---|---|
| Time After Dosing (hours) | IR Capsule | IR Tablet | Two Hour CR Tablet | Four Hour CR Tablet | Six Hour CR Tablet |
| −0.5 | 3.0 | 0 | 0 | 0 | 0 |
| 0.5 | 939.3 | 818.2 | 287.2 | 144.1 | 53.5 |
| 1.0 | 1335.8 | 1413.0 | 579.2 | 337.1 | 176.1 |
| 2.0 | 1560.7 | 1616.6 | 973.8 | 569.0 | 393.8 |
| 3.0 | 1426.8 | 1402.1 | 1111.5 | 718.3 | 555.1 |
| 4.0 | 1292.3 | 1130.2 | 1109.2 | 826.1 | 616.3 |
| 6.0 | 851.3 | 759.6 | 933.2 | 753.2 | 525.6 |
| 8.0 | 536.9 | 506.4 | 690.1 | 691.7 | 524.7 |
| 10.0 | 386.3 | 328.3 | 540.3 | 631.1 | 430.6 |
| 12.0 | 250.9 | 227.1 | 417.3 | 597.5 | 429.9 |
| 16.0 | 124.3 | 121.8 | 229.0 | 390.1 | 357.2 |
| 24.0 | 33.2 | 52.6 | 81.2 | 171.0 | 168.3 |
| 36.0 | 7.1 | 6.5 | 17.2 | 29.4 | 39.8 |
| 48.0 | 11.8 | 6.5 | 6.6 | 11.4 | 12.6 |

TABLE 26C

| | Eplerenone Plasma Pharmacokinetic Parameters | | | | |
|---|---|---|---|---|---|
| Pharmacokinetic Parameter | IR Capsule | IR Tablet | TWO Hour CR Tablet | Four Hour CR Tablet | Six Hour CR Tablet |
| $AUC_{(0-48)}$ (ng/mL) hr | 12042.69 | 12092.16 | 11949.27 | 13263.23 | 10663.00 |
| $AUC_{(0-LQC)}$ (ng/mL) hr | 11944.77 | 11981.35 | 11706.29 | 13061.75 | 10588.93 |
| $AUC_{(0-\infty)}$ (ng/mL) hr | 11224.29 | 12188.89 | 12045.98 | 13402.55 | 10815.43 |
| $C_{max}$ (ng/mL) | 1704.90 | 1668.76 | 1152.65 | 878.87 | 709.91 |
| $C_{max}/AUC_{(0-LQC)}$ ($hr^{-1}$) | 0.16 | 0.17 | 0.11 | 0.07 | 0.08 |
| $T_{max}$ (hours) | 1.84 | 1.34 | 3.34 | 4.56 | 7.55 |
| $T_{½}$ (hours) | 4.08 | 4.10 | 5.17 | 5.41 | 6.01 |
| $XU_{(0-24)}$ (mg) | 1.82 | 1.98 | 1.81 | 1.57 | 1.47 |

TABLE 26C-continued

Eplerenone Plasma Pharmacokinetic Parameters

| Pharmaco-kinetic Parameter | IR Capsule | IR Tablet | TWO Hour CR Tablet | Four Hour CR Tablet | Six Hour CR Tablet |
|---|---|---|---|---|---|
| $XU_{(24-48)}$ (mg) | 0.01 | 0.06 | 0.00 | 0.16 | 0.17 |
| $XU_{(0-48)}$ mg) | 1.83 | 2.04 | 1.81 | 1.73 | 1.64 |

TABLE 26D

| Time After Dosing (hours) | Plasma Concentration Of Open Ring Lactone (ng/mL) | | | | |
|---|---|---|---|---|---|
| | IR Capsule | IR Tablet | Two Hour CR Tablet | Four Hour CR Tablet | Six Hour CR Tablet |
| −0.5 | 0 | 0 | 0 | 0 | 0 |
| 0.5 | 46.5 | 39.2 | 9.7 | 2.9 | 0.0 |
| 1.0 | 65.4 | 68.1 | 24.5 | 13.3 | 3.9 |
| 2.0 | 71.1 | 78.7 | 43.8 | 22.9 | 14.3 |
| 3.0 | 65.0 | 66.1 | 47.1 | 29.5 | 21.4 |
| 4.0 | 57.5 | 54.2 | 47.2 | 39.3 | 22.4 |
| 6.0 | 42.3 | 39.7 | 46.8 | 35.5 | 21.8 |
| 8.0 | 23.8 | 25.8 | 33.3 | 33.4 | 25.4 |
| 10.0 | 19.5 | 14.4 | 26.5 | 30.2 | 18.2 |
| 12.0 | 10.6 | 7.8 | 20.5 | 29.0 | 18.7 |
| 16.0 | 3.9 | 3.2 | 10.2 | 16.4 | 14.6 |
| 24.0 | 0.0 | 1.2 | 1.7 | 4.9 | 4.3 |
| 36.0 | 0 | 0 | 0 | 0 | 1.0 |
| 48.0 | 0 | 0 | 0 | 0 | 0 |

TABLE 26E

| Pharmaco-kinetic Parameter | Open Ring Lactone Plasma Pharmacokinetic Parameters | | | | |
|---|---|---|---|---|---|
| | IR Capsule | IR Tablet | Two Hour CR Tablet | Four Hour CR Tablet | Six Hour CR Tablet |
| $AUC_{(0-48)}$ (ng/mL) hr | 533.56 | 502.88 | 527.62 | 554.71 | 402.03 |
| $AUC_{(0-LQC)}$ (ng/mL) hr | 504.91 | 475.75 | 489.86 | 495.61 | 356.94 |
| $C_{max}$ (ng/mL) | 86.73 | 81.81 | 51.16 | 44.26 | 32.59 |
| $T_{max}$ (hours) | 1.89 | 1.67 | 4.34 | 4.79 | 7.67 |
| $XU_{(0-24)}$ (mg) | 5.94 | 6.43 | 6.81 | 6.42 | 4.83 |
| $XU_{(24-48)}$ (mg) | 0.16 | 0.32 | 0.25 | 0.70 | 0.74 |
| $XU_{(0-48)}$ (mg) | 6.10 | 6.75 | 7.06 | 7.12 | 5.56 |

TABLE 26F

| $D_{value}$ | Micronized Eplerenone Particle Size Distribution in Microns | |
|---|---|---|
| | IR Capsule | IR Tablet, Two Hour, Four Hour and Six Hour CR Tablets |
| $D_5$ | 2 | 3 |
| $D_{10}$ | 3 | 5 |
| $D_{50}$ | 18 | 33 |
| $D_{75}$ | 39 | 63 |
| $D_{90}$ | 82 | 96 |
| $D_{95}$ | 114 | 119 |

EXAMPLE 27

Effect of Food Study

An open-label randomized, cross-over study was employed to evaluate the pharmacokinetic profiles of eplerenone under fasted and fed conditions, and the safety and tolerability of eplerenone. Safety was assessed based on adverse events, vital signs and clinical laboratory tests. Twelve healthy male subjects were randomized to receive a single 100 mg dose of eplerenone on days 1 and 8 under (i) fasted conditions, or (ii) immediately following a high-fat breakfast. The subjects were orally administered (dosed) a single 100 mg dose of eplerenone in the form of the capsule described in Example 7, together with approximately 200 to 240 mL of water at 0800 hours on days 1 and 8. Subjects randomized to receive a high-fat breakfast were to completely ingest the meal within 20 minutes prior to dosing. The high-fat meal contained approximately 33 g protein, 75 g fat, 58 g carbohydrates and 1000 calories. Blood samples were collected at −0.5 (predose), 0.5, 1, 2, 3, 4, 6, 8, 12, 16, 24, 28, 32, 48 and 72 hours post dose and analyzed to determine the concentration of eplerenone and its open lactone ring form. There were no clinically significant changes in vital signs or physical examinations. All adverse events were mild in severity. The mean results are reported in Tables 27A and 27B below.

TABLE 27A

| Time After Dosing (hours) | Plasma Concentration (ng/mL) | | | |
|---|---|---|---|---|
| | Fasted Conditions | | High Fat Breakfast | |
| | Eplerenone | Open Ring Lactone Form | Eplerenone | Open Ring Lactone Form |
| −0.5 | 0 | 0 | 0 | 0 |
| 0.5 | 1010.500 | 69.163 | 71.225 | 2.300 |
| 1.0 | 1562.667 | 91.208 | 366.192 | 17.392 |
| 2.0 | 1393.333 | 70.600 | 712.250 | 36.964 |
| 3.0 | 1174.417 | 58.833 | 1038.167 | 56.742 |
| 4.0 | 955.167 | 45.042 | 1239.750 | 66.817 |
| 6.0 | 586.583 | 31.773 | 946.000 | 51.675 |
| 8.0 | 387.583 | 18.708 | 672.833 | 30.950 |
| 12.0 | 150.850 | 5.519 | 282.250 | 12.708 |
| 16.0 | 68.783 | 0 | 130.467 | 2.540 |
| 24.0 | 17.667 | 0 | 39.008 | 0 |
| 28.0 | 7.617 | 0 | 21.733 | 0 |
| 32.0 | 3.283 | 0 | 7.508 | 0 |
| 48.0 | 0 | 0 | 1.908 | 0 |
| 72.0 | 0 | 0 | 0 | 0 |

TABLE 27B

| Pharmaco-kinetic Parameter | Fasted Conditions | | High Fat Breakfast | |
|---|---|---|---|---|
| | Eplerenone | Open Ring Lactone Form | Eplerenone | Open Ring Lactone Form |
| $AUC_{(0-96)}$ (ng/mL) hr | 9202.063 | 430.624 | 10171.631 | 470.137 |
| $C_{max}$ (ng/mL) | 1634.167 | 100.158 | 1334.333 | 73.858 |
| $T_{max}$ (hours) | 1.292 | 3.076 | 3.750 | 3.198 |
| $T_{1/2}$ (hours) | 3.369 | 3.750 | 3.71 | 1.125 |

For both eplerenone and its open ring lactone form, the high-fat meal led to a reduction in $C_{max}$ and an increase in $T_{max}$ but had minimal or no measurable effect upon $AUC_{0-96}$ and $T_{1/2}$. The results indicate that the high fat meal had minimal effect on the extent of eplerenone absorption, but it did decrease the rate of absorption. Accordingly, dosing of eplerenone can be made without regard for meal time, as the effect of food appears to have minimal clinical significance.

EXAMPLE 28

Multiple Dose Study

Multiple oral dose tolerability and the pharmacokinetics of several dosages of eplerenone were evaluated in a double-blind, randomized, placebo-controlled, rising oral dose, sequential panel study of 40 healthy male subjects (five groups of eight subjects). The study medication was administered in three sequential dose panels, with each panel including eplerenone, spironolactone and placebo. A single dose of 100 mg (one 100 mg dose), 300 mg (three 100 mg dose capsules) or 1000 mg dose eplerenone (five 200 mg dose capsules), 1000 mg dose of spironolactone, or placebo was administered on Day 1. The 100 mg and 200 mg dose capsules corresponded to those described in Examples 7 and 8, respectively. Following a 48-hour interval, the study drug was administered once a day for 11 days. Antialdosterone activity was determined following a fludrocortisone challenge on Days 12–13. Plasma pharmacokinetic results are reported in Table 28 below:

TABLE 28

| EPLERENONE DOSE: | Eplerenone | | Open Ring Form | |
|---|---|---|---|---|
| PHARMACOKINETIC PARAMETER | Single Dose | Multiple Dose | Single Dose | Multiple Dose |
| 100 mg Dose: | | | | |
| AUC (ng/mL) hr | 11349 | 11772 | 613 | 663 |
| $C_{max}$ (ng/mL) | 1747 | 1904 | 108 | 129 |
| $T_{max}$ (hours) | 1.8 | 1.1 | 1.7 | 0.7 |
| $T_{1/2}$ (hours) | 3.9 | 4.0 | 3.5 | 3.3 |
| 300 mg Dose: | | | | |
| AUC (ng/mL) hr | 23890 | 26514 | 1844 | 2200 |
| $C_{max}$ (ng/mL) | 3227 | 3582 | 292 | 364 |
| $T_{max}$ (hours) | 2.4 | 1.8 | 1.8 | 1.3 |
| $T_{1/2}$ (hours) | 4.6 | 4.6 | 3.0 | 3.5 |
| 1000 mg Dose: | | | | |
| AUC (ng/mL) hr | 62053 | 63249 | 5912 | 6310 |
| $C_{max}$ (ng/mL) | 6885 | 7394 | 782 | 830 |
| $T_{max}$ (hours) | 2.0 | 1.4 | 1.7 | 1.3 |
| $T_{1/2}$ (hours) | 8.7 | 6.2 | 3.7 | 4.8 |

Eplerenone plasma concentrations were detectable at 24 hours postdose for all dosing groups. Plasma concentrations of eplerenone and mean dose-adjusted AUC values following either single or multiple doses indicate a lack of dose proportionality within the 100 mg to 1000 mg dosage range. Results for the open ring lactone form were consistent with dose proportionality following single or multiple doses. Overall, there was no significant or dose-related accumulation of either eplerenone or its open ring lactone form.

Excretion of total eplerenone (that is, eplerenone and its open ring lactone form) in the urine represented approximately 5% of the dose for all doses administered. Urinary excretion of total eplerenone occurred almost entirely within the first 24 hours after dosing. Eplerenone significantly increased the urinary $log_{10}$ (sodium/potassium) at doses of 100 mg to 1000 mg following single dose administration. There was, however, no sustained increase in urinary $log_{10}$ (sodium/potassium) values following multiple dose administration of either eplerenone or spironolactone. Serum sodium and potassium concentrations were not significantly changed following single doses of eplerenone, but transient reductions in sodium concentrations and increases in potassium concentrations were noted following multiple dose administration. Eplerenone produced dose-related increases in mean plasma renin (active and total) levels and serum aldosterone levels, but did not show any consistent, sustained or dose-related effects on most serum sex hormone and thyroid profiles.

EXAMPLE 29

Treatment of Hypertension Study

The safety and efficacy of a range of doses of eplerenone in the treatment of hypertension relative to placebo were evaluated in a multi-center, randomized, double-blind, placebo-lead-in, parallel group study. Spironolactone 50 mg BID was included as the active reference drug. Four hundred and seventeen patients were randomized to one of eight treatments: (i) placebo BID; (ii) eplerenone 50 mg QD; (iii) eplerenone 100 mg QD; (iv) eplerenone 400 mg QD; (v)

eplerenone 25 mg BID; (vi) eplerenone 50 mg BID; (vii) eplerenone 200 mg BID; and (viii) spironolactone 50 mg BID. The primary efficacy variable was the change in cuff diastolic blood pressure (ΔDBP; sitting) measured at trough plasma levels after eight weeks of double blind treatment. The secondary variables measured were the change in trough cuff systolic blood pressure (ΔSBP; sitting), change in 24 hour mean diastolic blood pressure (ΔDBP), and change in 24 hour mean systolic blood pressure (ΔSBP). The primary and secondary efficacy variables were analyzed to compare BID versus QD dosing regimens for each eplerenone dose group, and both eplerenone and spironolactone versus placebo. Changes in plasma renin and serum aldosterone after eight weeks of dosing were also analyzed as secondary measures of efficacy.

All eplerenone doses lowered cuff diastolic and systolic pressures from baseline after eight weeks of treatment compared to placebo. Greater reductions in diastolic and systolic blood pressure were observed with increasing doses of eplerenone. In general, equivalent reductions in blood pressure values were associated with the QD and BID dosing regimens. There was, however, a trend toward greater reduction with the BID dosing regimen. Similar changes were observed in the 24 hour trough ambulatory blood pressures. Over the course of the study, the mean change in heart rate from baseline was minimal in all treatment groups, with the largest mean increase and decrease in heart rate being +2 beats/minute and −1.8 beats/minute, respectively. Consistent with aldosterone receptor antagonism, there were increases in aldosterone in both the eplerenone and spironolactone treatment groups compared to placebo as well as increases in both total and active renin levels. Safety was assessed by comparing the incidence of adverse events, withdrawals, and the results of urinalysis, hematology and biochemistry laboratory tests across the treatment group to the placebo group.

There were small but consistent increases in potassium and decreases in sodium in all of the eplerenone treatment groups. There were increases in BUN, uric acid levels and decreases in urine pH compared to placebo in the eplerenone treatment groups. Each eplerenone dosing regimen was well tolerated by the subjects. No adverse side effects were observed at 1000 mg, the highest dose administered.

The specific pharmaceutical compositions of each eplerenone capsule are reported in Examples 5, 6, 7 and 8. The placebo was a conventional capsule containing lactose. The spironolactone used in the study was obtained from Searle Canada (Oakville, Ontario).

The mean results obtained from the subjects tested are reported in Tables 29A and 29B below.

TABLE 29A

| Treatment Regimen | Primary Efficacy Variable: ΔDBP at trough (mmHg, sitting) | Secondary Efficacy Variables: ΔSBP at trough (mmHg, sitting) | 24 hour mean ΔDBP (mmHg) | 24 hour mean ΔSBP (mmHg) |
| --- | --- | --- | --- | --- |
| Placebo | −1.0 | 2.0 | 0.6 | 0.0 |
| Eplerenone 50 mg QD | −4.4 | −4.6 | −4.8 | −7.1 |
| Eplerenone 100 mg QD | −4.5 | −8.0 | −6.1 | −9.7 |
| Eplerenone 400 mg QD | −8.9 | −14.1 | −7.6 | −13.0 |
| Eplerenone 25 mg BID | −4.5 | −8.9 | −3.9 | −7.4 |
| Eplerenone 50 mg BID | −7.8 | −11.8 | −7.2 | −12.6 |
| Eplerenone 200 mg BID | −9.4 | −15.8 | −9.3 | −15.9 |
| Spironolactone 50 mg BID | −9.5 | −17.6 | −8.9 | −15.7 |

An average decrease in diastolic blood pressure of about 5% or greater was observed over an interval of about 12 to 24 hours after administration of the study medication.

TABLE 29B

| Treatment Regimen | Plasma Renin Active: Mean Change From Baseline (mU/L) | Serum Aldosterone: Mean Change From Baseline (ng/dL) |
| --- | --- | --- |
| Placebo | 2.2 | 1.0 |
| Eplerenone 50 mg QD | 2.9 | 6.0 |
| Eplerenone 100 mg QD | 13.9 | 10.5 |
| Eplerenone 400 mg QD | 21.2 | 19.2 |
| Eplerenone 25 mg BID | 1.2 | 7.3 |
| Eplerenone 50 mg BID | 15.0 | 10.0 |
| Eplerenone 200 mg BID | 32.0 | 32.8 |
| Spironolactone 50 mg BID | 13.3 | 19.2 |

An average increase in plasma renin concentration of about 10% or greater was observed over an interval of about 12 to 24 hours after administration of the study medication. An average increase in plasma aldosterone concentration of about 50% or greater was observed over an interval of about 12 to 24 hours after administration of the study medication.

EXAMPLE 30

Effect of Eplerenone Particle Size

The effect of the particle size of the eplerenone starting material used in the pharmaceutical composition on eplerenone plasma concentrations and relative bioavailability was studied in a dog model. Four healthy female beagle dogs weighing between 8 to 12 kg were intragastrically administered one immediate release (IR) capsule containing the formulation described in Table 30A below followed by about 10 mL of water.

TABLE 30A

| INGREDIENT | WEIGHT % OF TABLET | Amount (mg) |
|---|---|---|
| Eplerenone | 50.00 | 200.00 |
| Lactose, Fast-Flo ™, Hydrous | 36.95 | 147.80 |
| Microcrystalline Cellulose (Avicel ® PH102) | 7.25 | 29.00 |
| Sodium Lauryl Sulfate | 0.50 | 2.00 |
| Croscarmellose Sodium | 2.00 | 8.00 |
| Talc | 2.50 | 10.00 |
| Colloidal Silicon Dioxide | 0.50 | 2.00 |
| Magnesium Stearate | 0.30 | 1.20 |
| Total | 100.00 | 400.00 |
| Capsules, Size #0, White Opaque | 1 Capsule | |

The dogs were fasted for 15 to 20 hours prior to administration of the capsule and were not fed again until at least 4 hours after dose administration. Blood samples (approximately 3 mL) were collected by venipuncture in chilled tubes containing heparin at 0, 0.5, 1, 2, 3, 4, 6, 8 and 24 hours after dose administration. The blood samples were immediately placed on ice. Separation of plasma from the blood samples was complete after about 15 minutes of centrifugation. The resulting plasma samples were frozen at about −20° C. and stored until analyzed. Analysis was performed using an LC/MS/MS procedure.

This study was conducted using the same four dogs for three formulations that were identical except for the particle size of the eplerenone starting material. The three formulations assayed used eplerenone starting materials having a $D_{90}$ particle size (that is, at least 90% of the particles were) less than about 212 microns, less than about 86 microns, and less than about 36 microns, respectively. A minimum of a five day wash-out period was permitted between administration of each of the formulations. Reducing the $D_{90}$ particle size of the eplerenone starting material from about 212 microns to less than about 86 microns increased relative bioavailability by almost 100%. The mean results are reported in Tables 30B and 30C below.

TABLE 30B

| | Blood Serum Eplerenone Concentration (µg/mL) | | |
|---|---|---|---|
| Time (hours) | $D_{90}$ = 212 microns | $D_{90}$ = 86 microns | $D_{90}$ = 36 microns |
| 0 | 0 | 0 | 0 |
| 0.5 | 1.83 | 3.65 | 1.99 |
| 1.0 | 2.40 | 6.18 | 5.86 |
| 2.0 | 3.77 | 6.89 | 6.77 |
| 3.0 | 2.85 | 5.70 | 6.60 |
| 4.0 | 2.61 | 4.39 | 5.56 |
| 6.0 | 1.63 | 3.11 | 3.31 |
| 8.0 | 1.10 | 1.90 | 2.09 |
| 24.0 | 0.0252 | 0.032 | 0.0706 |

TABLE 30C

| | Pharmacokinetic Parameter Value | | |
|---|---|---|---|
| Pharmaco-kinetic Parameter | $D_{90}$ = 212 microns | $D_{90}$ = 86 microns | $D_{90}$ = 36 microns |
| $C_{max}$ (µg/mL) | 3.98 | 7.02 | 7.39 |
| $T_{max}$ (hours) | 1.50 | 1.75 | 2.25 |
| AUC [(µg/mL)hr] | 26.6 | 49.2 | 53.1 |
| Relative Bioavailability (%) | 53.25 | 100 | 107.9 |

DEFINITIONS

The term "carrier material" means material included in a pharmaceutical composition to impart certain desirable properties. For example, in the case of a tablet, carrier material can be added to moderate dissolution rate, mask a bad taste, or improve appearance of the tablet.

The term "matrix" or "matrix system" means the combination of all carrier materials of a given formulation in which the active drug is incorporated.

The term "$AUC_{(0-48)}$" means the area under the plasma concentration-time curve from t=0 to t=48 in units of [(ng/mL)hr] determined using the linear trapezoidal rule.

The term "$AUC_{(0-LQC)}$" means the area under the plasma concentration-time curve from t=0 to the last quantifiable concentration ("LQC") in units of [(ng/mL)hr] determined using the trapezoidal rule.

The term "$C_{max}$" means the maximum observed concentration.

The term "$T_{max}$" means the time at which $C_{max}$ occurred.

The term "$T_{1/2}$" means the terminal half-life, in units of hours, determined via simple linear regression of natural log (ln) concentration vs. time for data points in the 'terminal phase' of the concentration-time curve. $T_{1/2}$ was computed as $-\ln(2)/(-\beta)$.

The term "$AUC_{(0-\infty)}$ is calculated as $AUC_{(0-LQC)}$+LQC/ $(-\beta)$, where LQC was the last quantifiable plasma concentration and $\beta$ is the slope from the calculation of $T_{1/2}$.

The term "$C_{max}/AUC_{(0-LQC)}$" means the rate of absorption.

The term "$XU_{(0-\tau)}$" means the total amount of eplerenone (or inactive open lactone ring form of eplerenone) in the urine during each collection period (0–24, 24–48 and 0–48 hours) calculated as the urine drug concentration multiplied by the urine volume.

The term "MRT" is the mean resident time calculated as the area under the moment curve ($AUMC_{(0-96)}$ divided by $AUC_{(0-96)}$.

The term "CL/F" means the apparent (oral) clearance calculated as (1000×dose in mg)/$AUC_{(0-96)}$.

As various changes could be made in the above formulations and methods without departing from the scope of the invention, it is intended that all matter contained in the above description be interpreted as illustrative and not in a limiting sense. All patent documents listed herein are incorporated by reference.

What is claimed is:

1. A pharmaceutical composition comprising (a) particulate eplerenone having a $D_{90}$ particle size of about 25 to about 400 microns, in an amount of about 10 mg to about 1000 mg, and (b) one or more pharmaceutically acceptable carrier materials; said composition being in a form of a unit dosage tablet having a hardness of about 3.5 to about 22 kP, and being an immediate release composition wherein at least about 50% of said eplerenone is dissolved in vitro within about 15 minutes in a 1% sodium dodecyl sulfate solution at 37° C.

2. The composition of claim 1 wherein the eplerenone is in an amount of about 20 mg to about 400 mg.

3. The composition of claim 1 wherein the eplerenone is in an amount of about 25 mg to about 150 mg.

4. The composition of claim 1 wherein the eplerenone is in an amount of about 25 mg to about 100 mg.

5. The composition of claim 1 wherein the carrier materials comprise one or more materials selected from the group consisting of purified cellulose, microcrystalline cellulose, and alkylcelluloses and their derivatives and salts.

6. The composition of claim 1 wherein the carrier materials comprise one or more pharmaceutically acceptable binding agents in a total amount of about 0.5% to about 25% by weight of the composition.

7. The composition of claim 6 wherein the binding agents are selected from the group consisting of acacia, tragacanth, sucrose, gelatin, glucose, starch, celluloses, alginic acid and salts thereof, magnesium aluminum silicate, polyethylene glycol, gums, polysaccharide acids, bentonites, polyvinylpyrrolidone, polymethacrylates, hydroxypropylmethylcellulose, hydroxypropylcellulose, ethylcellulose, and pregelatinized starch.

8. The composition of claim 1 wherein the carrier materials comprise one or more pharmaceutically acceptable diluents in a total amount of about 5% to about 99% by weight of the composition.

9. The composition of claim 8 wherein the diluents are selected from the group consisting of lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, and bentonite.

10. The composition of claim 1 wherein the carrier materials comprise one or more pharmaceutically acceptable disintegrants in a total amount of about 0.5% to about 30% by weight of the composition.

11. The composition of claim 10 wherein the disintegrants are selected from the group consisting of starches, sodium starch glycolate, clays, celluloses, alginates, pregelatinized corn starches, crospovidone, and gums.

12. The composition of claim 1 wherein the carrier materials comprise one or more pharmaceutically acceptable wetting agents in a total amount of about 0.1% to about 15% by weight of the composition.

13. The composition of claim 12 wherein the wetting agents are selected from the group consisting of oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, and sodium lauryl sulfate.

14. The composition of claim 1 wherein the carrier materials comprise one or more pharmaceutically acceptable lubricants in a total amount of about 0.1% to about 10% by weight of the composition.

15. The composition of claim 14 wherein the lubricants are selected from the group consisting of glyceryl behapate, magnesium, calcium and sodium stearates, stearic acid, hydrogenated vegetable oils, talc, waxes, Stearowet, boric acid, sodium benzoate, sodium acetate, sodium chloride, DL-leucine, polyethylene glycols, sodium oleate, sodium lauryl sulfate, and magnesium lauryl sulfate.

16. The composition of claim 1 wherein the carrier materials comprise one or more pharmaceutically acceptable anti-adherents or glidants in a total amount of about 0.25% to about 10% by weight of the composition.

17. The composition of claim 16 wherein the anti-adherents or glidants are selected from the group consisting of talc, corn starch, DL-leucine, sodium lauryl sulfate, and magnesium, calcium and sodium stearates.

18. The composition of claim 1 wherein the eplerenone is present in an amount of about 1% to about 90% by weight of the composition.

19. The composition of claim 1 wherein the carrier materials comprise one or more materials selected from the group consisting of diluents, binding agents, disintegrants, wetting agents, lubricants, anti-adherents and glidants.

20. The composition of claim 1 wherein the carrier materials comprise hydroxypropylmethylcellulose.

21. The composition of claim 1 wherein the carrier materials comprise lactose.

22. The composition of claim 1 wherein the carrier materials comprise microcrystalline cellulose.

23. The composition of claim 1 wherein the carrier materials comprise croscarmellose sodium.

24. The composition of claim 1 wherein the carrier materials comprise (a) lactose in an amount of about 5% to about 90%; (b) microcrystalline cellulose in an amount of about 5% to about 90%; and (c) hydroxypropylmethylcellulose in an amount of about 0.5% to about 10%; all by weight of the composition.

25. The composition of claim 24 wherein the eplerenone is in an amount of about 1% to about 90% by weight of the composition.

26. The composition of claim 25 that comprises:
 (a) about 19% to about 40% by weight of eplerenone;
 (b) about 32% to about 52% by weight of lactose;
 (c) about 8% to about 28% by weight of microcrystalline cellulose; and
 (d) about 1% to about 8% by weight of hydroxypropylmethylcellulose.

27. The composition of claim 25 that comprises:
 (a) about 24% to about 35% by weight of eplerenone;
 (b) about 37% to about 47% by weight of lactose;
 (c) about 13% to about 23% by weight of microcrystalline cellulose; and
 (d) about 2% to about 4% by weight of hydroxypropylmethylcellulose;
and that further comprises:
 (e) about 2% to about 6% by weight of croscarmellose sodium.

28. The composition of claim 27 that comprises:
 (a) about 28% to about 31% by weight of eplerenone;
 (b) about 41% to about 43% by weight of lactose monohydrate;
 (c) about 17% to about 19% by weight of microcrystalline cellulose;
 (d) about 2.5% to about 3.5% by weight of hydroxypropylmethylcellulose; and
 (e) about 4.5% to about 5.5% by weight of croscarmellose sodium.

29. The composition of claim 28 that is a coated or uncoated unit dosage tablet, and that prior to coating comprises:
 (a) about 29.4% by weight of eplerenone;
 (b) about 42% by weight of lactose;

(c) about 18.1% by weight of microcrystalline cellulose;

(d) about 3% by weight of hydroxypropylmethylcellulose;

(e) about 5% by weight of croscarmellose sodium;

(f) about 1% by weight of talc; and (g) about 0.5% by weight of magnesium stearate.

30. The composition of claim 1 wherein the eplerenone is in an amount of about 23 mg to about 27 mg, and wherein the carrier materials comprise:

(a) about 34 mg to about 38 mg lactose;

(b) about 14 mg to about 17 mg microcrystalline cellulose;

(c) about 1 mg to about 4 mg hydroxypropylmethylcellulose;

(d) about 3 mg to about 6 mg croscarmellose sodium;

(e) about 0.25 mg to about 1.5 mg sodium lauryl sulfate;

(f) about 0.25 mg to about 1.5 mg talc; and (g) about 0.1 mg to about 1 mg magnesium stearate.

31. The composition of claim 1 wherein the eplerenone is in an amount of about 48 mg to about 52 mg, and wherein the carrier materials comprise:

(a) about 70 mg to about 73 mg lactose;

(b) about 29 mg to about 33 mg microcrystalline cellulose;

(c) about 4 mg to about 6 mg hydroxypropylmethylcellulose;

(d) about 6 mg to about 10 mg croscarmellose sodium;

(e) about 1 mg to about 2.5 mg sodium lauryl sulfate;

(f) about 1 mg to about 2.5 mg talc; and (g) about 1 mg to about 1.5 mg magnesium stearate.

32. The composition of claim 1 wherein the eplerenone is in an amount of about 98 mg to about 102 mg, and wherein the carrier materials comprise:

(a) about 141 mg to about 145 mg lactose;

(b) about 60 mg to about 64 mg microcrystalline cellulose;

(c) about 9 mg to about 11 mg hydroxypropylmethylcellulose;

(d) about 16 mg to about 18 mg croscarmellose sodium;

(e) about 3 mg to about 4 mg sodium lauryl sulfate;

(f) about 3 mg to about 4 mg talc; and (g) about 1 mg to about 2 mg magnesium stearate.

33. The composition of claim 1 wherein the tablet is coated.

34. The composition of claim 1 wherein the amount of said eplerenone in the tablet is about 25 mg.

35. The composition of claim 1 that is suitable for once or twice a day oral administration as an aldosterone receptor blocker.

36. The composition of claim 1 that provides a therapeutic effect as an aldosterone receptor blocker in a human subject over an interval of about 12 to about 24 hours after ingestion of the composition.

37. The composition of claim 1 that provides a therapeutic effect as an aldosterone receptor blocker in a human subject over an interval of about 24 hours after ingestion.

38. The composition of claim 1 that releases at least 50% of said eplerenone in vitro within 20 minutes in 0.1N HCl.

39. The composition of claim 38 that is suitable for once or twice a day oral administration.

40. The composition of claim 1 that is suitable for once a day oral administration, and that releases at least 50% of said eplerenone in vitro within 15 minutes in 0.1N HCl.

41. The composition of claim 1 wherein said tablet is prepared by direct compression.

42. The composition of claim 1 wherein said tablet is prepared by wet granulation followed by compression.

43. The composition of claim 1 wherein said tablet is prepared by dry granulation followed by compression.

44. The composition of claim 1 wherein the eplerenone has a $D_{90}$ particle size of about 25 to about 200 microns.

45. The composition of claim 1 wherein the eplerenone has a $D_{90}$ particle size of about 25 to about 150 microns.

46. The composition of claim 1 wherein the eplerenone has a $D_{90}$ particle size of about 30 to about 110 microns.

47. The composition of claim 1 wherein the eplerenone has a $D_{90}$ particle size of about 30 to about 50 microns.

48. The composition of claim 1 wherein the eplerenone has a $D_{90}$ particle size of about 50 to about 150 microns.

49. The composition of claim 1 wherein the eplerenone has a $D_{90}$ particle size of about 75 to about 125 microns.

50. The composition of claim 1 wherein ingestion of the composition by a human subject causes an average increase of at least about 10% in blood serum renin concentration in the subject over an interval of about 12 to about 24 hours after said ingestion.

51. The composition of claim 1 wherein ingestion of the composition by a human subject causes an average increase of at least about 50% in blood serum aldosterone concentration in the subject over an interval of about 12 to about 24 hours after said ingestion.

52. The composition of claim 1 wherein ingestion of the composition by a human subject causes an average decrease of at least about 5% in diastolic blood pressure in the subject over an interval of about 12 to about 24 hours after said ingestion.

53. A method of treating a condition or disorder where treatment with an aldosterone receptor blocker is indicated, the method comprising orally administering the composition of claim 1 to a patient in need of such treatment.

54. The method of claim 53 wherein the condition or disorder is heart failure.

55. The method of claim 53 wherein the condition or disorder is hypertension.

56. The method of claim 53 wherein the condition or disorder is edema associated with liver insufficiency.

57. The method of claim 53 wherein the condition or disorder is post-myocardial infarction.

58. The composition of claim 34 wherein the tablet has a hardness of about 3.5 to about 9 kP.

59. The composition of claim 1 wherein the amount of said eplerenone in the tablet is about 50 mg.

60. The composition of claim 59 wherein the tablet has a hardness of about 5 to about 13 kP.

61. The composition of claim 1 wherein the amount of said eplerenone in the tablet is about 100 mg.

62. The composition of claim 61 wherein the tablet has a hardness of about 8 to about 22 kP.

* * * * *